(12) United States Patent
Van Snick et al.

(10) Patent No.: US 11,485,780 B2
(45) Date of Patent: Nov. 1, 2022

(54) TGF-β3 SPECIFIC ANTIBODIES AND METHODS AND USES THEREOF

(71) Applicant: LUDWIG INSTITUTE FOR CANCER RESEARCH, LTD., New York, NY (US)

(72) Inventors: Jacques Van Snick, Brussels (BE); Catherine Uyttenhove, Brussels (BE)

(73) Assignee: Ludwig Institute for Cancer Research, Ltd., New York, NY (US)

( * ) Notice: Subject to any disclaimer, the term of this patent is extended or adjusted under 35 U.S.C. 154(b) by 181 days.

(21) Appl. No.: 16/913,067

(22) Filed: Jun. 26, 2020

(65) Prior Publication Data

US 2020/0392221 A1  Dec. 17, 2020

Related U.S. Application Data

(62) Division of application No. 15/580,746, filed as application No. PCT/US2016/036965 on Jun. 10, 2016, now Pat. No. 10,723,793.

(60) Provisional application No. 62/174,896, filed on Jun. 12, 2015.

(51) Int. Cl.
| | | |
|---|---|---|
| *C07K 16/22* | (2006.01) | |
| *A61K 47/68* | (2017.01) | |
| *A61P 35/00* | (2006.01) | |
| *A61K 39/395* | (2006.01) | |
| *A61P 35/04* | (2006.01) | |
| *C07K 16/30* | (2006.01) | |
| *G01N 33/574* | (2006.01) | |
| *A61K 45/06* | (2006.01) | |
| *A61K 39/00* | (2006.01) | |

(52) U.S. Cl.
CPC .......... *C07K 16/22* (2013.01); *A61K 39/3955* (2013.01); *A61K 47/6845* (2017.08); *A61P 35/00* (2018.01); *A61P 35/04* (2018.01); *C07K 16/30* (2013.01); *G01N 33/57488* (2013.01); *A61K 45/06* (2013.01); *A61K 2039/505* (2013.01); *A61K 2039/54* (2013.01); *C07K 2317/33* (2013.01); *C07K 2317/54* (2013.01); *C07K 2317/56* (2013.01); *C07K 2317/565* (2013.01); *C07K 2317/622* (2013.01); *C07K 2317/626* (2013.01); *C07K 2317/73* (2013.01); *C07K 2317/76* (2013.01); *G01N 2333/495* (2013.01)

(58) Field of Classification Search
None
See application file for complete search history.

(56) References Cited

U.S. PATENT DOCUMENTS

| | | | | |
|---|---|---|---|---|
| 5,262,319 | A * | 11/1993 | Iwata | ......................... A61P 9/12 435/378 |
| 5,571,714 | A | 11/1996 | Dasch et al. | |
| 2005/0176933 | A1 | 8/2005 | Chen et al. | |
| 2006/0039913 | A1 | 2/2006 | Das et al. | |
| 2006/0222643 | A1 | 10/2006 | Tsunoda et al. | |
| 2010/0285034 | A1 | 11/2010 | Gregory | |
| 2014/0127230 | A1* | 5/2014 | Ledbetter | ................ C07K 16/22 435/69.6 |

FOREIGN PATENT DOCUMENTS

| | | |
|---|---|---|
| WO | 92/00330 A1 | 1/1992 |
| WO | 2005/097832 A2 | 10/2005 |
| WO | 2006/086469 A2 | 8/2006 |
| WO | 2007/076391 A1 | 7/2007 |
| WO | 2012/167143 A1 | 12/2012 |
| WO | 2013/134365 A1 | 9/2013 |

OTHER PUBLICATIONS

Terabe, M. et al., "Synergistic Enhancement of CD8+ T Cell-Mediated Tumor Vaccine Efficacy by an Anti-Transforming Growth Factor-β Monoclonal Antibody", 2009, Clin Cancer Res, 15, pp. 6560-6569.

Takaku S. et al., Blockade of TGF-β enhances tumor vaccine efficacy mediated by CD8+ T cells, 2010, Int. J. Cancer, vol. 126(7): 1666, pp. 1-19.

(Continued)

*Primary Examiner* — Brian Gangle
*Assistant Examiner* — Andrea K McCollum
(74) *Attorney, Agent, or Firm* — Hoffmann & Baron, LLP

(57) ABSTRACT

Specific binding members, particularly antibodies and fragments thereof, which bind to transforming growth factor beta 3 (TGF-β3) are provided, particularly recognizing human and mouse TGF-β3, particularly antibodies and fragments that do not recognize or bind TGF-β1 or TGF-β2. Particular antibodies are provided which specifically recognize and neutralize TGF-β3. These antibodies are useful in the diagnosis and treatment of conditions associated with activated or elevated TGF-β3, including cancer, and for modulating immune cells and immune response, including immune response to cancer or cancer antigens. The anti-TGF-β3 antibodies, variable regions or CDR domain sequences thereof, and fragments thereof may also be used in therapy in combination with chemotherapeutics, immune modulators, or anti-cancer agents and/or with other antibodies or fragments thereof. Antibodies of this type are exemplified by the novel antibodies hereof, including antibody MTGF-β3-9, MTGF-β3-12, MTGF-β3-16, MTGF-β3-17 and MTGF-β3-19, whose sequences are provided herein.

16 Claims, 21 Drawing Sheets

Specification includes a Sequence Listing.

(56) References Cited

OTHER PUBLICATIONS

Van Belle, P. et al., "Melanoma-Associated Expression of Transforming Growth Factor-β Isoforms", 1996, American J. of Pathology, vol. 148, No. 6, pp. 1887-1894.
Li, C. et al., "Role of Transforming Growth Factor β in Lymphatic Metastasis in Breast Cancer", 1998, Int. J. Cancer, vol. 79, pp. 455-459.
Terabe, M. et al., "Transforming Growth Factor-β Production and Myeloid Cells Are an Effector Mechanism through Which CD1d-restricted T Cells Block Cytotoxic T Lymphocyte-mediated tumor Immunosurveillance: Abrogation Prevents Tumor Recurrence", 2003, Journal of Experimental Medicine, vol. 198, No. 11, pp. 1741-1752.
Nam, J-S., et al., "An Anti-Transforming Growth Factor β Antibody Suppresses Metastasis via Cooperative Effects on Multiple Cell Compartments", 2008, Cancer Res, vol. 68, 10, pp. 3835-3843.
Biswas, S. et al., "Inhibition of TGF-β with neutralizing antibodies prevents radiation-induced acceleration of metastatic cancer progression", 2007, vol. 117, No. 5, pp. 1305-1313.
Vanpoille-Box, C., "TGFβ is a Master Regulator of Radiation Therapy-Induced Antitumor Immunity", 2015, Cancer Res, vol. 75, 11, pp. 2232-2242.
Vajdos, F. et al., "Comprehensive Functional Maps of the Antigen-binding Site of an Anti-ErbB2 Antibody Obtained with Shotgun Scanning Mutagenesis", 2002, J Mol Biol., Jul. 5; 320(2), pp. 415-428.
Brown, M. et al., "Tolerance of single, but not multiple, amino acid replacements in antibody VH CDR 2: a means of minimizing B cell wastage from somatic hypermutation?" J Immunol. May 1, 1996; 156(9) pp. 3285-3291.

\* cited by examiner

FIGURE 4C

| Mab | VL | CDR1 | CDR2 | CDR3 | VH | CDR1 | CDR2 | CDR3 |
|---|---|---|---|---|---|---|---|---|
| TGFb3-9/8 | 127aa | KASQSVINDVA | YASNRYT | QQDYSSPYT | 139aa | SSWMH | RIEPGDGDTIYNGNFKG | RMITTQAAMDY |
| TGFb-3-1901/16 | 127aa | KASQSVINAVA | YASNRYT | QQDYSSPYT | 139aa | SSWIH | RIYPGDGDTNYTGKFKG | RMITTQAAMDY |
| TGFb-3-1679/2 | 127aa | KASQSVINAVA | YASNRYT | QQDYSSPYT | 139aa | SSWIH | RIYPGDGDTNYTGKFKG | RMITTQAAMDY |
| TGFb-3-1203/11 | 133aa | KSSQSLLNSGNQKNYLA | GASTRES | QNDHGFPLT | 138aa | DVYIN | KIGPGTGRTYYNEKFKG | YYGWGYAMDY |
| TGFb-3-1719/13 | 131aa | RSSQSLIHSHGNTYLH | KLSNRFS | SQSTHVPFT | 138aa | SYWIT | DIFPGTGSTNYNEKFKT | KLGPNYAVDY |

| | Coating 1719 4µg/ml | |
|---|---|---|
| hTGF-ß3(pg/ml) | MTGF-ß3-9 biotin | MTGF-ß3-16 biotin |
| 10000 | 2.618 | 2.79 |
| 3333 | 1.684 | 2.25 |
| 1111 | 0.827 | 1.176 |
| 370 | 0.458 | 0.604 |
| 123 | 0.234 | 0.288 |
| 41 | 0.181 | 0.196 |
| 14 | 0.128 | 0.169 |
| 5 | 0.138 | 0.116 |
| 1 | 0.146 | 0.099 |
| 0 | 0.105 | 0.089 |

Effect of MTGFß3-19 mAb on the growth of 4T1-P1A tumor cells in n

Area under the curve calculated for tumor size from day 13 to 39

Effect of MTGFß3-19 on the survival of immune Balb/c mice injected with 4T1-P1A cells

FIGURE 15

Antibody MTGF-β3-9

Heavy Chain:
DNA sequence (417 bp)
Leader sequence-FR1-CDR1-FR2-CDR2-FR3-CDR3-FR4
ATGGAATGGCCTTGTATCTTTCTCTTCCTCCTGTCAGTAACTGAAGGTGTCCACTCCCAGGTTCTGC
TGCAGCAGTCTGGACCTGAGCTGGTGAAGCCTGGGGCCTCAGTGAAGATTTCCTGCAAGGCTTCTGG
CTATGCATTCAGTAGCTCCTGGATGCACTGGGTGAAGCAGAGGCCTGGAAAGGGTCTTGAGTGGATT
GGACGGATTTTTCCTGGAGATGGAGATACTATCTACAATGGGAATTTCAAGGGCAAGGCCACACTTA
CTGCAGACAAATCCTCCAGCACAGCCTACATGCAACTCAGCAGCCTGACATCTGAGGACTCTGCGGT
CTACTTCTGTGCAAGAAGGATGATTACGACTCAGGCGGCTATGGACTACTGGGGTCAAGGAACCTCA
GTCACCGTCTCCTCA

Amino acid sequence (139 AA)
Leader sequence-FR1-CDR1-FR2-CDR2-FR3-CDR3-FR4
MEWPCIFLFLLSVTEGVHSQVLLQQSGPELVKPGASVKISCKASGYAFSSSWMHWVKQRPGKGLEWI
GRIFPGDGDTIYNGNFKGKATLTADKSSSTAYMQLSSLTSEDSAVYFCARRMITTQAAMDYWGQGTS
VTVSS

Light Chain:
DNA sequence (381 bp)
Leader sequence-FR1-CDR1-FR2-CDR2-FR3-CDR3-FR4
ATGAAGTCACAGACCCAGGTCTTCGTATTTCTACTGCTCTGTGTGTCTGGTGCTCATGGGAGTATTG
TGATGACCCAGACTCCCAAATTCCTGCTTGTATCAGCAGGAGACAGGGTTACCATAACCTGCAAGGC
CAGTCAGAGTGTGATTAATGATGTAGCTTGGTATCAACAGAAGCCAGGGCAGTCTCCTAAACTGCTG
ATATACTATGCATCCAATCGGTACACTGGAGTCCCTGATCGCTTCACTGGCAATGGATATGGACGG
ATTTCACTTTCACCATCAGCACTGTGCAGGCTGAAGACCTGGCAGTTTATTTCTGTCAGCAGGATTA
TAGCTCTCCGTACACGTTCGGAGGGGGGACCAAGCTGGAAATAAAA

Amino acid sequence (127 AA)
Leader sequence-FR1-CDR1-FR2-CDR2-FR3-CDR3-FR4
MKSQTQVFVFLLLCVSGAHGSIVMTQTPKFLLVSAGDRVTITCKASQSVINDVAWYQQKPGQSPKLL
IYYASNRYTGVPDRFTGNGYGDFTFTISTVQAEDLAVYFCQQDYSSPYTFGGGTKLEIK

FIGURE 16

Antibody MTGF-β3-12

Heavy Chain:
DNA sequence (414 bp)
Leader sequence-FR1-CDR1-FR2-CDR2-FR3-CDR3-FR4
ATGGAATGGAGCTGGGTCTTTCTCTTCCTCCTGTCAGTAACTGCAGGTGTCCACTGCCAGGTCCAGC
TGAAGCAGTCTGGAGCTGAGCTGGTGAAGCCTGGGGCTTCAGTGAAGATATCCTGCAAGGCTTCTGG
CTACACCTTCACTGACTACTATATAAACTGGGTGAAGCAGAGGCCTGGACAGGGCCTTGAGTGGATT
GGGAAGATTGGTCCTGGAACTGGTCGTACTTACTACAATGAGAAGTTCAAGGGCAAGGCCACACTGA
CTGCAGACAAATCCTCCAGCACAGCCTACATGCAGCTCAGCAGCCTGACATCTGAGGACTCTGCAGT
CTATTTCTGTGCAATCTACTATGGTTGGGGCTATGCTATGGACTACTGGGGTCAAGGAACCTCAGTC
ACCGTCTCCTCA

Amino acid sequence (138 AA)
Leader sequence-FR1-CDR1-FR2-CDR2-FR3-CDR3-FR4
MEWSWVFLFLLSVTAGVHCQVQLKQSGAELVKPGASVKISCKASGYTFTDYYINWVKQRPGQGLEWI
GKIGPGTGRTYYNEKFKGKATLTADKSSSTAYMQLSSLTSEDSAVYFCAIYYGWGYAMDYWGQGTSV
TVSS

Light Chain:
DNA sequence (399 bp)
Leader sequence-FR1-CDR1-FR2-CDR2-FR3-CDR3-FR4
ATGGAATCACAGACTCAGGTCCTCATCTCCTTGCTGTTCTGGGTATCTGGTACCTGTGGGGACATTG
TGATGACACAGTCTCCATCCTCCCTGAGTGTGTCAGCAGGAGAGAAGGTCACTATGAGCTGCAAGTC
CAGTCAGAGTCTGTTAAACAGTGGAAATCAAAAGAACTACTTGGCCTGGTACCAGCAGAAATCAGGG
CAGCCTCCTAAACTGTTGATCTATGGGGCATCCACTAGGGAATCTGGGGTCCCTGATCGCTTCACAG
GCAGTGGATCTGGAACCGATTTCACTCTTACCATCAGCAGTGTGCAGGCTGAAGACCTGGCAGTTTA
TTACTGTCAGAATGATCATGGTTTTCCGCTCACGTTCGGTGCTGGGACCAAGCTGGAGCTGAAA

Amino acid sequence (133 AA)
Leader sequence-FR1-CDR1-FR2-CDR2-FR3-CDR3-FR4
MESQTQVLISLLFWVSGTCGDIVMTQSPSSLSVSAGEKVTMSCKSSQSLLNSGNQKNYLAWYQQKSG
QPPKLLIYGASTRESGVPDRFTGSGSGTDFTLTISSVQAEDLAVYYCQNDHGFPLTFGAGTKLELK

FIGURE 17

Antibody MTGF-β3-16

Heavy Chain:
DNA sequence (417 bp)
Leader sequence-FR1-CDR1-FR2-CDR2-FR3-CDR3-FR4
ATGGAATGGCCTTGTATCTTTCTCTTCCTCCTGTCAGTAACTGAAGGTGTCCACTCCCAGGTTCTCC
TGCAGCAGTCTGGACCTGAGCTGGTGAAGCCTGGGGCCTCAGTGAAGATTTCCTGCAAGGCTTCTGG
CTACGCATTCAGTAGCTCCTGGATACACTGGGTGAAGCAGAGGCCTGGAAAGGGTCTTGAGTGGATT
GGACGGATTTATCCGGGAGATGGAGATACTAACTATACTGGGAAGTTCAAGGGCAAGGCCACACTTA
CTGCAGACAAATCCTCCAGCACAGCCTACATGCAACTCAGCAGCTTGACATCTGAGGACTCTGCGGT
CTACTTCTGTGCAAGAAGGATGATTACGACTCAGGCGGCTATGGACTACTGGGGTCAAGGAACCTCA
GTCACCGTCTCCTCA

Amino acid sequence (139 AA)
Leader sequence-FR1-CDR1-FR2-CDR2-FR3-CDR3-FR4
MEWPCIFLFLLSVTEGVHSQVLLQQSGPELVKPGASVKISCKASGYAFSSSWIHWVKQRPGKGLEWI
GRIYPGDGDTNYTGKFKGKATLTADKSSSTAYMQLSSLTSEDSAVYFCAREMITTQAAMDYWGQGTS
VTVSS

Light Chain:
DNA sequence (381 bp)
Leader sequence-FR1-CDR1-FR2-CDR2-FR3-CDR3-FR4
ATGAAGTCACAGACCCAGGTCTTCGTATTTCTACTGCTCTGTGTGTCTGGTGCTCATGGGAGTTTTG
TGATGACCCAGACTCCCAAATTCCTGCTTGTATCAGCAGGAGACAGGGTTACCATAACCTGCAAGGC
CAGTCAGAGTGTGATTAATGCTGTAGCTTGGTACCAACAGAAGCCAGGGCAGTCTCCTAAACTGCTG
ATATACTATGCATCCAATCGCTACACTGGAGTCCCTGATCGCTTCACTGGCAATGGATATGGGACGG
ATTTCACTTTCACCATCAGCACTGTGCAGGCTGAAGACCTGGCAGTTTATTTCTGTCAGCAGGATTA
TAGCTCTCCGTACACGTTCGGAGGGGGGACCAAGCTGGAAATAAAA

Amino acid sequence (127 AA)
Leader sequence-FR1-CDR1-FR2-CDR2-FR3-CDR3-FR4
MKSQTQVFVFLLLCVSGAHGSFVMTQTPKFLLVSAGDRVTITCKASQSVINAVAWYQQKPGQSPKLL
IYYASNRYTGVPDRFTGNGYGTDFTFTISTVQAEDLAVYFCQQDYSSPYTFGGGTKLEIK

FIGURE 18

Antibody MTGF-β3-17

Heavy Chain:
DNA sequence (414 bp)
Leader sequence-FR1-CDR1-FR2-CDR2-FR3-CDR3-FR4
ATGGGATGGAGCTGTATCATCCTCATTTTGGTAGCAGCAGCTACAGGTGTCCACTCCCAGGTCCAAC
TGCAGCAGCCTGGGGCTGAGCTTGTGAAGCCTGGGGCTTCAGTGAAGATGTCCTGCAAGGCTTCTGG
CTACATTTTCACCAGCTACTGGATAACCTGGGTGAAGCAGAGGCCTGGACAAGGCCTTGAGTGGATT
GGAGATATTTTTCCTGGGACTGGTAGTACTAACTACAATGAGAAGTTCAAGACCAAGGTCTCACTGA
CTGTAGACACATCCTCCAGCACAGCCAACATGCAGCTCAGCAGCCTGACATCTGAGGACTCAGCGGT
CTATTCCTGTGCAAGAAAACTGGGCCCTAACTATGCTGTGGACTACTGGGGTCAAGGAACCTCAGTC
ACCGTCTCCTCA

Amino acid sequence (138 AA)
Leader sequence-FR1-CDR1-FR2-CDR2-FR3-CDR3-FR4
MGWSCIILILVAAATGVHSQVQLQQPGAELVKPGASVKMSCKASGYIFTSYWITWVKQRPGQGLEWI
GDIFPGTGSTNYNEKFKTKASLTVDTSSSTANMQLSSLTSEDSAVYSCARKLGPNYAVDYWGQGTSV
TVSS

Light Chain:
DNA sequence (393 bp)
Leader sequence-FR1-CDR1-FR2-CDR2-FR3-CDR3-FR4
ATGAAGTTGCCTGTTAGGCTGTTGGTGCTGATGTTCTGGATTCCTGCTTCCAGCAGTGATGTTGTGA
TGACCCAAACTCCACTCTCCCTGCCTGTCAGTCTTGGAGATCAAGCCTCCATCTCTTGCAGATCTAG
TCAGAGCCTTATACACAGTCATGGAAACACCTATTTACATTGGTACCTGCAGAAGCCAGGCCAGTCT
CCAAAGCTCCTGATCTACAAACTTTCCAACCGATTTTCTGGGGTCCCAGACAGGTTCAGTGGCAGTG
GATCAGGGACAGATTTCACACTCAAGATCAGCAGAGTGGAGGCTGAGGATCTGGGAGTTTATTTCTG
CTCTCAAAGTACACATGTTCCATTCACGTTCGGCTCGGGACAAAGTTGGAAATAAAA

Amino acid sequence (131 AA)
Leader sequence-FR1-CDR1-FR2-CDR2-FR3-CDR3-FR4
MKLPVRLLVLMFWIPASSSDVVMTQTPLSLPVSLGDQASISCRSSQSLIHSHGNTYLHWYLQKPGQS
PKLLIYKLSNRFSGVPDRFSGSGSGTDFTLKISRVEAEDLGVYFCSQSTHVPFTFGSGTKLEIK

FIGURE 19

Antibody MTGF-β3-19

Heavy Chain:
DNA sequence (417 bp)
Leader sequence-FR1-CDR1-FR2-CDR2-FR3-CDR3-FR4
ATGGAATGGCCTTGTATCTTTCTCTTCCTCCTGTCAGTAACTGAAGGTGTCCACTCCCAGGTTCTCC
TGCAGCAGTCTGGACCTGAGCTGGTGAAGCCTGGGGCCTCAGTGAAGATTTCCTGCAAGGCTTCTGG
CTACGCATTCAGTAGCTCCTGGATACACTGGGTGAAGCAGAGGCCTGGAAAGGGTCTTGAGTGGATT
GGACGGATTTATCCGGGAGATGGAGATACTAACTATACTGGGAAGTTCAAGGGCAAGGCCACACTTA
CTGCAGACAAATCCTCCAGCACAGCCTACATGCAACTCAGCAGCCTGACATCTGAGGACTCTGCGGT
CTACTTCTGTGCAAGAAGGATGATTACGACTCAGGCGGCTATGGACTACTGGGGTCAAGGAACCTCA
GTCACCGTCTCCTCA

Amino acid sequence (139 AA)
Leader sequence-FR1-CDR1-FR2-CDR2-FR3-CDR3-FR4
MEWPCIFLFLLSVTEGVHSQVLLQQSGPELVKPGASVKISCKASGYAFSSSWIHWVKQRPGKGLEWI
GRIYPGDGDTNYTGKFKGKATLTADKSSSTAYMQLSSLTSEDSAVYFCAREMITTQAAMDYWGQGTS
VTVSS

Light Chain:
DNA sequence (381 bp)
Leader sequence-FR1-CDR1-FR2-CDR2-FR3-CDR3-FR4
ATGAAGTCACAGACCCAGGTCTTCGTATTTCTACTGCTCTGTGTGTCTGGTGCTCATGGGAGTTTTG
TGATGACCCAGACTCCCAAATTCCTGCTTGTATCAGCAGGAGACAGGGTTACCATAACCTGCAAGGC
CAGTCAGAGTGTGATTAATGCTGTAGCTTGGTACCAACAGAAGCCAGGGCAGTCTCCTAAACTGCTG
ATATACTATGCATCCAATCGCTACACTGGAGTCCCTGATCGCTTCACTGGCAATGGATATGGGACGG
ATTTCACTTTCACCATCAGCACTGTGCAGGCTGAAGACCTGGCAGTTTATTTCTGTCAGCAGGATTA
TAGCTCTCCGTACACGTTCGGAGGGGGGACCAAGCTGGAAATAAAA

Amino acid sequence (127 AA)
Leader sequence-FR1-CDR1-FR2-CDR2-FR3-CDR3-FR4
MKSQTQVFVFLLLCVSGAHGSFVMTQTPKFLLVSAGDRVTITCKASQSVINAVAWYQQKPGQSPKLL
IYYASNRYTGVPDRFTGNGYGTDFTFTISTVQAEDLAVYFCQQDYSSPYTFGGGTKLEIK

# TGF-β3 SPECIFIC ANTIBODIES AND METHODS AND USES THEREOF

CROSS REFERENCE TO RELATED APPLICATIONS

The present application is divisional of U.S. application Ser. No. 15/580,746 filed Dec. 8, 2017, which is a National Stage Application claiming the priority of co-pending PCT Application No. PCT/US2016/036965 filed Jun. 10, 2016, which in turn claims priority under from 35 U.S.C. § 119(e) from U.S. Provisional Application Ser. No. 62/174,896, filed Jun. 12, 2015. The applications are herein specifically incorporated by reference in their entireties.

FIELD OF THE INVENTION

The present invention relates to specific binding members, particularly antibodies and fragments thereof, which bind to transforming growth factor beta 3 (TGF-β3), particularly recognizing human and mouse TGF-β3 and not recognizing or binding TGF-β1 or TGF-β2. The antibodies are useful in the diagnosis and treatment of conditions associated with activated or elevated TGF-β3, including cancer, and for modulating immune cells and immune response, including immune response to cancer or cancer antigens. The antibodies, variable regions or CDR domain sequences thereof, and fragments thereof may also be used in therapy in combination with chemotherapeutics, radiation therapy, immune modulators, cancer vaccines, cancer antigens, or anti-cancer agents and/or with other antibodies or fragments.

BACKGROUND OF THE INVENTION

The transforming growth factor beta (TGF-β) family forms a group of three isoforms, TGF-β1, TGF-β2, and TGF-β3, with their structure formed by interrelated dimeric polypeptide chains. Pleiotropic and redundant functions of the TGF-β family relate to control of numerous aspects and effects of cell functions in all tissues of the human body, including aspects of proliferation, differentiation, and migration (Poniatowski L A, et al, 2015, Mediators Inflamm, 2015; 137823). Although the isoforms are similar in sequence (TGF-β3 active domain shares 86% similarity with TGF-β1 and 91% with TGF-β2), protein crystal structure and NMR studies have shown that TGF-l33 active domain structure is different from TGF-β1. Comparison of the TGF-β3 with the structure of TGF-β2 (Schlunegger M P, Grüter M G, 1992, Nature 358:430-434; Daopin S, Piez K A, Ogawa Y, Davies D R, 1992, Science 257:369-373) reveals a virtually identical central core. Differences exist in the conformations of the N-terminal alpha-helix and in the beta-sheet loops (Mittl P R1, Priestle J P, Cox D A, McMaster G, Cerletti N, Grüter M G, 1996, Protein Science July 5 (7): 1261-1271).

In most cells, three types of cell surface proteins mediate TGF-β signaling: TGF-β receptor I (TβRI), II (TβRII) and III (TβRIII) (Cheifetz S, Like B, Massagué J, J Biol Chem. 1986 Jul. 25; 261(21):9972-8). Bioactive forms of TGF-βs are dimers held together by hydrophobic interactions and, in most cases, by an intersubunit disulfide bond as well. The dimeric structure of these ligands suggests that they function by bringing together pairs of type I and II receptors, forming heterotetrameric receptor complexes (Sun P D, Davies D R, Annu Rev Biophys Biomol Struct. 1995; 24:269-91). Binding of TGF-β to extracellular domains of both receptors also induces proper conformation of the intracellular kinase domains. These receptors are subject to reversible post-translational modifications (phosphorylation, ubiquitylation and sumoylation) that regulate stability and availability of receptors as well as SMAD and non-SMAD pathway activation.

Receptor phosphorylation activates the TGF-β signaling pathway the ligand binds to TβRII first, followed by subsequent phosphorylation of a Gly-Ser regulatory region (GS-domain) within TβRI. This leads to incorporation of TβRI and formation of a large ligand-receptor complex that consists of dimeric TGF-β ligand and two pairs of TβRI and TβRII (Shi Y, Massague J, Cell. 2003 Jun. 13; 113(6):685-700). TGF-β1 and TGF-β3 bind to TβRII without participation of type I receptor, whereas TGF-β2 interacts only with combination of both receptors (Derynck R, Feng X H, Biochim Biophys Acta. 1997 Oct. 24; 1333(2):F105-50). It has been observed that different ligand/receptor engagements of the TGF-β family may contribute to qualitative and quantitative differences in signaling events and biological outcomes (Hart P J et al Nat Struct Biol 2002 9(3):203-208). Furthermore, temporal-spatial expression of some of the TGF-β isoforms in embryogenesis is very different, indicating uncompensated, non-overlapping functions throughout development (Akhurst R J et al Development 1990 110(2): 445-460).

Overexpression of transforming growth factor β (TGF-β) is frequently associated with tumor metastasis and poor prognosis in animal models of cancer and cancer patients (Donkor M K et al., 2012, Oncolmmunology, 1(2):162-171). Members of the TGF-β family are potent regulatory cytokines that affect multiple cell types of the immune system mediating pro-inflammatory or anti-inflammatory responses. The effect of TGF-β on T-cells is highly versatile. In concert with other soluble factors, it controls the maturation, differentiation and activity of various T cell subsets that either prevent or actuate infections, graft-versus-host reactions, immune diseases, and cancer formation (Schon H T et al., 2014, Hepatobiliary Surg Nutr, 2014, Dec. 3(6): 386-406).

Studies have demonstrated that blockade of TGF-β, using mouse TGF-β generic antibody 1D11 (which recognizes TGF-β1, TGF-β2 and TGF-β3), synergistically enhances tumor vaccines in animal models via CD8$^+$ T cells (Terabe M et al (2009) Clin Cancer Res 15:6560-6569; Takaku S et al (2010) Int J Cancer 126(7):1666). Also, TGFβ production by tumor cells and by myeloid-derived suppressor cells (MDSC) present at tumor sites along with TGFβ immune suppressive activity at the tumor site implicates blocking TGFβ to enhance antigen uptake, presentation, and activation of antitumor immune response mediated by therapeutic vaccines.

Several publications show differences in melanoma-associated expression of TGF-β isoforms. Van Belle et al showed that TGF-β1 is expressed by some melanocytes and almost uniformly by nevi and melanomas while TGF-β2 and TGF-β3 were not detected in normal melanocytes but were found in nevi and in all forms of melanomas (early and advanced primary and metastatic melanomas) in a tumor progression related manner. They state that "TGF-β2 was heterogeneously expressed in advanced primary and metastatic melanomas whereas TGF-β3 was uniformly and highly expressed in these lesions" (P. Van Belle 1996 American J. of Pathology 148(6):1887-1894).

Also, TGF-β3 but not TGF-β1 immunostaining was reported to correlate in breast carcinomas with poor survival prognosis, and when combined with lymph node involvement, TGF-β3 was a highly significant prognostic factor for survival (Ghellal A1 2000 Anticancer Res 20: 4413). Moreover, plasma levels of TGF-β3 and complexes of TGF-β3 and its receptor CD105 (TGF-β3-CD105) were significantly elevated in breast cancer patients with positive lymph nodes compared to those without node metastasis, and their levels correlated with lymph node status (Li C1 1998 Int. J. Cancer 79:455).

Particularly, studies have demonstrated TGF-β3's involvement in the following: contributing to epithelial mesenchymal transition (EMT); elevated TGF-β3 levels in breast cancer and prostate metastasis; and elevated levels of TGF-β3 detected in late stage tumors and aggressive tumors such as breast, prostate, and lung.

Thus, it is apparent that, by targeting specific isoforms of TGF-β, one could avoid damaging inflammatory consequences of blocking all isoforms of TGF-β. Moreover, the differential expression patterns of TGF-β isoforms in different cancer types gives researchers a unique opportunity to target cancer cells more specifically and with greater efficacy. There is an unmet need in the field to generate therapeutic TGF-β antibodies against its isoforms, including particularly against TGF-β3. In addition, the tools developed for recognizing different TGF-β isoforms are powerful diagnostic and prognostic sources. The present invention addresses such unmet needs in the field and particularly with regard to TGF-β3.

The citation of references herein shall not be construed as an admission that such is prior art to the present invention.

SUMMARY OF THE INVENTION

In a general aspect, the present invention provides novel transforming growth factor beta TGF-β antibodies directed against human TGF-β3. In an aspect, the TGF-β3 antibodies of the invention are more specific for TGF-β3 binding than their binding to TGF-β1 or to TGF-β2. In an aspect, the TGF-β3 antibodies of the invention do not cross react or bind to other members of the TGF-beta family, and particularly do not cross react or bind to TGF-β1 or to TGF-β2. In an aspect, the invention provides an isolated specific binding member, particularly an antibody or fragment thereof, including an Fab fragment and a single chain or domain antibody, which specifically recognizes TGF-β3. In a particular aspect, the antibody or active fragment thereof neutralizes TGF-β3 activity.

The invention provides antibodies specifically directed against TGFβ3 for diagnostic and therapeutic purposes. In particular, antibodies specific for TGFβ3 are provided, wherein said antibodies recognize and are capable of binding human and mouse TGFβ3, and do not recognize other forms of TGF-beta, TGF-β1 or TGF-β2.

The antibodies of the present invention have diagnostic and therapeutic use in cancer and in immune modulation, including modulating the immune response to cancer and in cancer vaccines. The antibodies of the invention are applicable in characterizing and in modulating the activity of TGF-β3, particularly in neutralizing TGF-β3 activity.

In a further aspect, the present invention provides an antibody or fragment thereof, which recognizes TGF-β3 and is selected from antibodies MTGF-β3-9/8 (MTGF-β3-9), MTGF-β3-1203/11 (MTGF-β3-12), MTGF-β3-1679/2 (MTGF-β3-16), MTGF-β3-1719/13 (MTGF-β3-17) and MTGF-β3-1901/16 (MTGF-β3-19). In a particular aspect the invention provides an antibody or active fragment thereof that specifically recognizes and neutralizes TGF-β3 and is selected from antibodies MTGF-β3-9/8 (MTGF-β3-9), MTGF-β3-1203/11 (MTGF-β3-12), MTGF-β3-1679/2 (MTGF-β3-16) and MTGF-β3-1901/16 (MTGF-β3-19).

The binding of an antibody to its target antigen is mediated through the complementarity-determining regions (CDRs) of its heavy and light chains. Accordingly, specific binding members based on the CDR regions of the heavy or light chain, or of both the heavy and light chain, of the antibodies of the invention, particularly of any of antibodies MTGF-β3-9/8 (MTGF-β3-9), MTGF-β3-1203/11 (MTGF-β3-12), MTGF-β3-1679/2 (MTGF-β3-16), MTGF-β3-1719/13 (MTGF-β3-17), and MTGF-β3-1901/16 (MTGF-β3-19), will be useful specific binding members for therapy and/or diagnostics. In an aspect, the invention provides TGF-β3 antibody capable of binding and neutralizing TGF-β3 comprising the light chain and heavy chain variable region CDR1, CDR2 and CDR3 sequences as provided herein and set out in FIG. 4C. In a particular aspect the invention provides TGF-β3 specific antibody capable of specifically binding and neutralizing TGF-β3, wherein the antibody does not bind or neutralize TGF-β1 or TGF-β2, comprising the light chain and heavy chain variable region CDR1, CDR2 and CDR3 sequences as provided herein and set out in FIG. 4C (SEQ ID NOs:1-21).

The invention provides an antibody directed against TGF-β3 comprising:

(a) a light chain variable region comprising a CDR1 sequence KASQSVINDVA (SEQ ID NO:1) or KASQSVINAVA (SEQ ID NO:7), a CDR2 sequence YASNRYT (SEQ ID NO:2), and a CDR3 sequence QQDYSSPT (SEQ ID NO:3), and a heavy chain variable region sequence comprising a CDR1 sequence SSWMH (SEQ ID NO:4) or SSWIH (SEQ ID NO:8), a CDR2 sequence RIFPGDGDTIYNGNFKG (SEQ ID NO:5) or RIYPGDGDTNYTGKFKG (SEQ ID NO:9), and a CDR3 sequence RMITTQAAMDY (SEQ ID NO:6);

(b) a light chain variable region comprising a CDR1 sequence KSSQSLLNSGNQKNYLA (SEQ ID NO:10), a CDR2 sequence GASTRES (SEQ ID NO:11), and a CDR3 sequence QNDHGFPLT (SEQ ID NO:12), and a heavy chain variable region sequence comprising a CDR1 sequence DYYIN (SEQ ID NO:13), a CDR2 sequence KIGPGTGRTYYNEKFKG (SEQ ID NO:14), and a CDR3 sequence YYGWGYAMDY (SEQ ID NO:15); or (c) a light chain variable region comprising a CDR1 sequence RSSQSLIHSHGNTYLH (SEQ ID NO:16), a CDR2 sequence KLSNRFS (SEQ ID NO:17), and a CDR3 sequence SQSTHVPFT (SEQ ID NO:18), and a heavy chain variable region sequence comprising a CDR1 sequence SYWIT (SEQ ID NO:19), a CDR2 sequence DIFPGTGSTNYNEKFKT (SEQ ID NO:20), and a CDR3 sequence KLGPNYAVDY (SEQ ID NO:21).

In one aspect, the invention provides an antibody specifically directed against and neutralizing TGF-β3, wherein the antibody does not bind or neutralize TGF-β1 or TGF-β2, comprising:

(a) a light chain variable region comprising a CDR1 sequence KASQSVINDVA (SEQ ID NO:1) or KASQSVINAVA (SEQ ID NO:7), a CDR2 sequence YASNRYT (SEQ ID NO:2), and a CDR3 sequence QQDYSSPT (SEQ ID NO:3), and a heavy chain variable region sequence comprising a CDR1 sequence SSWMH (SEQ ID NO:4) or SSWIH (SEQ ID NO:8), a CDR2 sequence RIFPGDGDTIYNGNFKG (SEQ ID NO:5) or RIYPGDGDTNYTGKFKG (SEQ ID NO:9), and a CDR3 sequence RMITTQAAMDY (SEQ ID NO:6); or (b) a light chain variable region comprising a CDR1 sequence KSSQSLLNSGNQKNYLA (SEQ ID NO:10), a CDR2 sequence GASTRES (SEQ ID NO:11), and a CDR3 sequence QNDHGFPLT (SEQ ID NO:12), and a heavy chain variable region sequence comprising a CDR1 sequence DYYIN (SEQ ID NO:13), a CDR2 sequence KIGPGTGRTYYNEKFKG (SEQ ID NO:14), and a CDR3 sequence YYGWGYAMDY (SEQ ID NO:15). In an aspect, the antibodies specifically directed against and neutralizing TGF-β3 compete with one another for TGF-β3 binding.

The invention provides TGF-β3 specific antibody comprising heavy chain variable region CDRs wherein the CDR1 domain comprises a sequence SSWXH wherein X is either M or I (SEQ ID NO:42), the CDR2 domain comprises a sequence RIX$_1$PGDGDTX$_2$YX$_3$GX$_4$FKG wherein X$_1$ is F or Y, X$_2$ is I or N, X$_3$ is N or T and X$_4$ is N or K (SEQ ID NO:43), and the CDR3 domain comprises a sequence RMITTQAAMDY (SEQ ID NO:6). In an aspect, the invention provides TGF-β3 specific antibody further comprising light chain variable region CDRs wherein the CDR1 domain comprises a sequence KASQSVINXVA wherein X is either D or A (SEQ ID NO:44), the CDR2 domain comprises a sequence YASNRT (SEQ ID NO:2), and the CDR3 domain comprises a sequence QQDYSSPYT (SEQ ID NO:3). In an aspect, the antibodies specifically directed against and neutralizing TGF-β3 compete with one another for TGF-β3 binding.

In one aspect, the invention provides a TGF-β3 antibody comprising the heavy chain variable region CDR sequences set out in FIG. 4C. In an aspect thereof, TGF-β3 specific antibody is provided having a heavy chain variable region comprising the CDR 1, CDR2 and CDR3 domain amino acid sequences of SSWMH (SEQ ID NO:4) or SSWIH (SEQ ID NO:8), RIFPGDGDTIYNGNFKG (SEQ ID NO:5) or RIYPGDGDTNYTGKFKG (SEQ ID NO:9), and RMITTQAAMDY (SEQ ID NO:6), respectively. In an aspect thereof, TGF-β3 specific antibody is provided having a heavy chain variable region comprising the CDR 1, CDR2 and CDR3 domain amino acid sequences of DYYIN (SEQ ID NO:13), KIGPGTGRTYYNEKFKG (SEQ ID NO:14), and YYGWGYAMDY (SEQ ID NO:15), respectively. In an aspect, TGF-β3 antibody is provided having a heavy chain variable region comprising the CDR 1, CDR2 and CDR3 domain amino acid sequences SYWIT (SEQ ID NO:19), DIFPGTGSTNYNEKFKT (SEQ ID NO:20), and KLGPNYAVDY (SEQ ID NO:21) respectively.

The antibody of the invention may comprise the heavy chain CDR domain region CDR1, CDR2 and CDR3 sequences of FIG. 4C (SEQ ID NOs: 4, 5, 6, 8, 9, 13, 14, 15, 19, 20, 21), and a light chain variable region. In an aspect, the TGF-β3 antibody further comprises the light chain variable region CDR sequences set out in FIG. 4C (SEQ ID NOs: 1, 2, 3, 7, 10, 11, 12, 16, 17, 18). In an aspect thereof, TGF-β3 specific antibody is provided having a light chain variable region comprising the CDR 1, CDR2 and CDR3 domain amino acid sequences of KASQSVINDVA (SEQ ID NO:1) or KASQSVINAVA (SEQ ID NO:7), YASNRYT (SEQ ID NO:2), and QQDYSSPT (SEQ ID NO:3), respectively, or of KSSQSLLNSGNQKNYLA (SEQ ID NO:10), GASTRES (SEQ ID NO:11), and QNDHGFPLT (SEQ ID NO:12), respectively. In an aspect, the invention provides TGF-β3 specific neutralizing antibodies with alternative heavy and light chain CDR sequences. In an aspect of the invention, the TGF-β3 specific neutralizing antibodies with alternative heavy and light chain CDR sequences compete with one another for TGF-β3 binding.

In a particular aspect, a TGF-β3 antibody of the invention comprises the heavy chain and light chain variable region amino acid sequence as set out in any of FIG. 15 (SEQ ID NOs: 23 and 25), 16 (SEQ ID NOs: 27 and 29), 17 (SEQ ID NOs: 31 and 33), 18 (SEQ ID NOs: 35 and 37) or 19 (SEQ ID NOs: 39 and 41). In an aspect, the TGF-β3 specific antibody of the invention comprises the heavy chain and light chain variable region amino acid sequence as set out in any of FIG. 15, 16, 17 or 19 (SEQ ID NOs: 23, 25, 27, 29, 31, 33, 35, 37, 39 and 41). A TGF-β3 antibody of the invention may comprise an amino acid sequence having at least 80%, at least 90%, at least 95% amino acid identity to the heavy chain variable region amino acid sequence and the light chain variable region amino acid sequence as set out in FIG. 15, 16, 17, 18 or 19 (SEQ ID NOs: 23 and 25, 27 and 29, 31 and 33, 35 and 37, 39 and 41). A TGF-β3 specific antibody of the invention, capable of specifically binding TGF-β3 and which does not bind TGF-β1 or TGF-β2, may comprise an amino acid sequence having at least 80%, at least 90%, at least 95% amino acid identity to the heavy chain variable region amino acid sequence and the light chain variable region amino acid sequence as set out in FIG. 15 (SEQ ID NO: 23 and 25), 16 (SEQ ID NO: 27 and 29), 17 (SEQ ID NO: 31 and 33) or 19 (SEQ ID NO: 39 and 41).

In a particular aspect, the antibody or active fragment thereof of the present invention neutralizes human and mouse TGF-β3. In an aspect, antibody of the invention neutralizes and blocks TGF-β3-mediated signaling in vivo in a mammal, particularly in a human or in a mouse. In an aspect, the antibody or active fragment thereof of the present invention neutralizes and blocks TGF-β3-mediated signaling in vivo in a mammal, without neutralizing or blocking TGF-β1 or TGF-β2 signaling in vivo in a mammal.

Accordingly, specific binding proteins such as antibodies which are based on the CDRs of the antibody(ies), particularly including the heavy chain CDRs identified herein, will be useful for targeting TGF-β3, particularly TGF-β3 expressing cells, or TGF-β3 activity in immune response, in diseases or in cancers. As the target of antibodies of the invention is specifically TGF-β3 and not TGF-β1 and/or TGF-β2, in an aspect of the invention the antibodies of the invention do no significantly bind to TGF-β forms or family members other than TGF-β3 and it is anticipated that there will be less toxicity and inflammatory response or untoward immune response or reaction in cell targets or in animals with the present TGF-β3 specific antibodies, particularly as compared to a pan-TGF-β antibody which recognizes more than one or all forms of TGF-β.

In another aspect of the invention, provided herein is an antibody(ies) or fragment(s) thereof that binds to the same epitope of TGF-β3 (such as particularly, human TGF-β3) as the antibody(ies) described herein. In another embodiment, provided herein is an antibody(ies) or antigen-binding fragment(s) thereof that competes with an antibody or antigen-binding fragment thereof described herein for binding to TGF-β3 (e.g., human TGF-β3). In a specific embodiment, provided herein is an antibody(ies) or antigen-binding fragment(s) thereof that competes with antibody or antigen-binding fragment thereof described herein for binding to TGF-β3 (e.g., human TGF-β3) to the extent that the antibody or antigen-binding fragment thereof described herein self-competes for binding to TGF-β3 (e.g., human TGF-β3).

In another specific embodiment, provided herein is a first antibody or antigen-binding fragment thereof that competes with an antibody or antigen-binding fragment thereof described herein for binding to TGF-β3 (e.g., human TGF-β3), wherein the first antibody or antigen-binding fragment thereof competes for binding in an assay comprising the following steps: (a) incubating TGF-β3 coated ELISA plates with the first antibody or antigen-binding fragment thereof in unlabeled form; (b) adding labeled antibody or antigen-binding fragment thereof described herein to the TGF-β3 coated ELISA plates and incubating TGF-β3 coated ELISA plates; and (c) detecting the binding of the antibody or antigen-binding fragment thereof described herein to TGF-β3. In an aspect, binding of an antibody TGFβ3-9 or antigen binding fragment thereof, antibody TGFβ3-19 or antigen binding fragment thereof, antibody TGFβ3-16 or antigen binding fragment thereof, or antibody TGFβ3-12 or antigen binding fragment thereof is detected after incubation with the first antibody or antigen binding fragment thereof. In an aspect, provided herein is a first antibody or antigen-binding fragment thereof that competes with an antibody or antigen-binding fragment thereof described herein for binding to TGF-β3 (e.g., human TGF-β3), wherein the first antibody or antigen-binding fragment thereof competes for binding in an assay comprising the following steps: (a) incubating TGF-β3 coated ELISA plates with the first antibody or antigen-binding fragment thereof in unlabeled form; (b) adding the biotinylated antibody or antigen-binding fragment thereof described herein to the TGF-β3 coated ELISA plates and incubating TGF-β3 coated ELISA plates; and (c) detecting the binding of the antibody or antigen-binding fragment thereof described herein to TGF-β3. In an aspect hereof, the labeled or biotinylated antibody or antigen binding fragment thereof is selected from antibody TGFβ3-9 or antigen binding fragment thereof, antibody TGFβ3-19 or antigen binding fragment thereof, antibody TGFβ3-16 or antigen binding fragment thereof, or antibody TGFβ3-12 or antigen binding fragment thereof. In an aspect, binding of antibody or antigen binding fragment of one or more of TGFβ3-9, TGFβ3-19, TGFβ3-16 or TGFβ3-12 is reduced, in particular is significantly reduced, in the presence of first antibody or antigen-binding fragment thereof in unlabeled form.

In another specific embodiment, provided herein is a first antibody or antigen-binding fragment thereof that competes with an antibody or antigen-binding fragment thereof described herein for binding to TGF-β3 (e.g., human TGF-β3), wherein the competition is exhibited as reduced binding of first antibody or antigen-binding fragment thereof to TGF-β3 (e.g., human TGF-β3) by more than 60% (e.g., 65%, 70%, 75%, 85%, 90%, 95%, or 98%, or between 60% to 65%, 65% to 70%, 70% to 75%, 75% to 80%, 80% to 85%, 85% to 95%, or 95% to 100%). In another specific embodiment, provided herein is a first antibody or antigen-binding fragment thereof that competes with an antibody or antigen-binding fragment thereof described herein for binding to TGF-β3 (e.g., human TGF-β3), wherein the competition is exhibited as reduced binding of antibody or antigen binding fragment of one or more of TGFβ3-9, TGFβ3-19, TGFβ3-16 or TGFβ3-12 by more than 60% (e.g., 65%, 70%, 75%, 85%, 90%, 95%, or 98%, or between 60% to 65%, 65% to 70%, 70% to 75%, 75% to 80%, 80% to 85%, 85% to 95%, or 95% to 100%) in the presence and/or after binding of the first antibody or antigen-binding fragment thereof.

In specific aspects, provided herein is an antibody which competes (e.g., in a dose dependent manner) for specific binding to TGF-β3 (e.g., human TGF-β3), with an antibody comprising (i) a VL domain comprising a VL CDR1, VL CDR2, and VL CDR3 having the amino acid sequences of the VL CDRs of an antibody listed in FIG. 4C; and (ii) a VH domain comprising a VH CDR1, VH CDR2, and VH CDR3 having the amino acid sequences of the CDRs of an antibody listed in FIG. 4C.

In a particular embodiment, provided herein is an antibody that competes (e.g., in a dose-dependent manner), for specific binding to TGF-β3 (e.g., human TGF-β3), with an antibody comprising the VH and VL CDRs of TGF-β3-9 (SEQ ID NO: 4, 5, 6 and 1, 2, 3).

In a particular embodiment, provided herein is an antibody that competes, for specific binding to TGF-β3 (e.g., human TGF-β3), with an antibody comprising the VH and VL CDRs of TGF-β3-19 (SEQ ID NO: 8, 9, 6 and 7, 2, 3).

In a particular embodiment, provided herein is an antibody that competes, for specific binding to TGF-β3 (e.g., human TGF-β3), with an antibody comprising the VH and VL CDRs of TGF-β3-16 (SEQ ID NO: 8, 9, 6 and 7, 2, 3).

In a particular embodiment, provided herein is an antibody that competes, for specific binding to TGF-β3 (e.g., human TGF-β3), with an antibody comprising the VH and VL CDRs of TGF-β3-12 (SEQ ID NO: 13, 14, 15 and 10, 11, 12).

In a specific embodiment, an antibody described herein is one that is competitively blocked (e.g., in a dose dependent manner) by an antibody comprising a VL domain having the amino acid sequence selected from the group consisting of SEQ ID NO: 1, 2, 3, 7, 10, 11 12 and a VH domain having the amino acid sequence selected from the group consisting of SEQ ID NO: 4, 5, 6, 8, 9, 13, 14 and 15, for specific binding to TGF-β3 (e.g., human TGF-β3).

In further aspects, the invention provides an isolated nucleic acid which comprises a sequence encoding a specific binding member or antibody as defined above, and methods of preparing specific binding members or antibodies of the invention which comprise expressing said nucleic acids under conditions to bring about expression of said binding member or antibody, and recovering the binding member or antibody. In one such aspect, a nucleic acid encoding antibody variable region sequence having the heavy chain amino acid sequences as set out in FIG. 15, 16, 17, 18 or 19 is provided or an antibody having heavy chain CDR domain sequences as set out in FIG. 4C, in SEQ ID NOs:4-6, 8, 9, 6, 13-15 or 19-21, or in FIG. 15, 16, 17, 18 or 19 is provided. In an aspect, nucleic acid encoding an antibody light chain variable region having the light chain amino acid sequences as set out in FIG. 15, 16, 17, 18 or 19 is provided or an antibody having light chain CDR domain sequences as set out in FIG. 4C, in SEQ ID NOs: 1-3, 7, 2, 3, 10-12 or 16-18, or in FIG. 15, 16, 17, 18 or 19 is provided. Exemplary encoding nucleic acid for TGF-β3 antibody heavy and light chain variable regions are provided in FIGS. 15 (SEQ ID NOs:22 and 24) 16 (SEQ ID NOs:26 and 28), 17 (SEQ ID NOs:30 and 32), 18 (SEQ ID Nos: 34 and 36), and 19 (SEQ ID NOs: 38 and 40). The present invention also relates to a recombinant DNA molecule or cloned gene, or a degenerate variant thereof, which encodes an antibody of the present invention; preferably a nucleic acid molecule, in particular a recombinant DNA molecule or cloned gene, encoding the antibody VH, particularly the CDR region sequences, and optionally additionally encoding the VL, particularly the CFR region sequences, which is capable of encoding a sequence selected from that of FIGS. 4C, 15, 16, 17, 18 and/or 19.

The unique specificity and affinity of the antibodies and fragments of the invention provides diagnostic and therapeutic uses to identify, characterize and target conditions associated with TGF-β3 expression, activity or activation. In particular, antibodies of the invention targeting TGF-β3 are useful in modulating immune response. In an aspect thereof, antibodies of the invention targeting TGF-β3 are useful in modulating immune response against cancer, cancer or tumor cells, and cancer or tumor antigens. The antibodies have applicability in therapeutic treatment or management of cancer. The antibodies have applicability in enhancing the anti-cancer immune response and in enhancing cancer vaccines. The antibodies have applicability in enhancing the therapeutic effect including the anti-cancer and/or anti-cellular effect of radiation therapy(ies). In a particular aspect the antibodies of the invention are applicable in treatment, management and/or prevention of cancers, including in cancer recurrence and metastasis. Applicable conditions include infectious disease, cancers, host immune response including in transplantation and immune diseases or disorders, such as autoimmune diseases or inflammatory conditions. Applicable cancers include adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In an aspect applicable cancers include or are selected from breast, melanoma, prostate and lung cancer. In an aspect, the TGF-β3 antibodies of the invention have applicability in treatment or modulation of breast, melanoma, prostate or lung cancer.

Evidence of TGFβ production by tumor cells and by myeloid-derived suppressor cells along with TGFβ immune suppressive activity at the tumor site supports that blocking TGFβ, particularly specifically blocking TGF-β3, can enhance antigen uptake, presentation, and activation of antitumor immune response mediated by therapeutic vaccines. Thus, in an aspect of the invention TGF-β3 antibody(ies), particularly TGF-β3 neutralizing antibody(ies), may be administered in conjunction with or in a composition of cancer antigen(s) and adjuvant(s), including to patients to promote a more robust priming and activation of the adaptive anti-tumor response to enhance immune therapies directed at cancers. Additional inhibitors to TGFβ activity, such as small molecules, antisense or aptamers can also be used to inhibit TGFβ activity, including or specifically TGF-β3.

Potent anti-tumor immunity requires modulating multiple arms of host immune response and targeting pathways that contributes to tumor cell growth and survival. Combining agents that modulate immune response and arrest tumor growth and progression can generate anticancer immunity and arrest tumor growth to improve clinical outcomes (Vanneman, M (2012) Nature Reviews Cancer (12):237-251). Thus, in an aspect of the invention the anti-TGF-β3 antibody(ies) may be administered alone or in combination with other treatments, therapeutics or agents, either simultaneously or sequentially dependent upon the condition to be treated. Immune modulators may be included in a composition with or administered with TGF-β3 antibody(ies) and/or administered at a different time to enhance immune modulation and/or cancer therapy, including immune therapies directed against cancer. An immune modulator may be an adjuvant. Applicable immune modulators include IDO, TDO (Platten M (2012) Cancer Research 72(21):5435-40), α-galactosyl ceramide and analogs thereof such as threitolceramide (ThrCer) and ThrCer 6, TLR ligands such as poly I:C (TLR3), MPL (TLR4), imiquimod (TLR7), R848 (TLR8) or CpG (TLR9), iCOS, CTLA-4, PD1, PD1 ligand, OX40 and OX40 ligand, Lag3, GITR, GITR ligand interleukins, tumor necrosis factor (TNF) or other growth factors, colony stimulating factors, T cell modulators including modulators of $CD8^+$ T cells, cytokines or hormones which stimulate the immune response or reduction or elimination of cancer cells or tumors (Mellman I (2011) Nature (480): 480-489). Additional immunmodulators are small molecules, antagonist antibodies or agonist antibodies targeting the applicable immune modulators including IDO, TDO, Toll like receptor family or iCOS, CTLA-4, PD1, PD1 ligand, OX40 and OX40 ligand, interleukins, tumor necrosis factor (TNF) or other growth factors, colony stimulating factors, T cell modulators including modulators of $CD8^+$ T cells, cytokines which stimulate the immune response or reduction or elimination of cancer cells or tumors.

Additional immune modulators, including TLR ligands such as poly I:C (TLR3), MPL (TLR4), imiquimod (TLR7), R848 (TLR8) or CpG (TLR9) can be used in combination with TGF-β1 specific neutralizing antibody to produce an enhanced immune stimulation and resulting protection from conditions in which it is desirable for the immune system to respond effectively such as infectious disease or cancer.

TGF-β3 specific antibody(ies) can also be used as immunostimulant(s) or adjuvant(s) in combined use with antigenic materials such as, without limitation, proteins, peptides, or nucleic acids and so forth in order to produce a protective immune response, such as a B-cell and IgG antibody response to the administered antigen. TGF-β3 specific antibody(ies) can also be used as immunostimulant(s) or adjuvant(s) in combined use with antigenic materials such as, without limitation, proteins, peptides, or nucleic acids and so forth in order to produce a protective immune response, such as a T-cell or CTL response to the administered antigen.

Such antigenic materials could be and may include any materials suitable for prevention or therapy of a/the particular disease. Specifically, with regards to cancer, examples of tumor associated peptide and protein antigens that can be administered to induce or enhance an immune response are derived from tumor associated genes and encoded proteins including MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1 and CT-7. For example, antigenic peptides characteristic of tumors include those listed in published PCT application WO00/20581 (PCT/US99/21230).

TGF-β3 antibodies, including TGF-β3 specific antibodies, are efficacious both in vitro and in vivo as has been shown. Hence, one aspect of the invention relates to stimulating an immune response in a subject, by administering TGF-β3 antibody or TGF-β3 specific antibody with or without an antigenic molecule, in an amount sufficient to stimulate a favorable immunologic response in such subject.

The invention includes compositions and or kits, comprising one or more TGF-β3 antibody or TGF-β3 specific antibody together with one or more immunogenic proteins or peptides. The compositions include pharmaceutical compositions and immunological compositions. The antibodies or compositions of the invention may be administered systemically or in a targeted fashion, including administration to an affected organ or organ of interest to a tumor, at the region or location of a tumor, or directly to a tumor, such as in intratumoral injection.

The antibodies, fragments thereof and recombinant antibodies comprising the CDR domains according to the invention may be used in a method of treatment or diagnosis of the human or animal body, such as a method of treatment of a tumor in a human patient which comprises administering to said patient an effective amount of the antibodies, fragments thereof and recombinant antibodies of the invention. The antibodies, fragments thereof and recombinant antibodies comprising the CDR domains according to the invention may be used in a method of stimulating or enhancing an immune response to cancer, tumor cells or cancer or tumor antigen(s) in a mammal, particularly in a human, comprises administering to said mammal an effective amount of the antibodies, fragments thereof and recombinant antibodies of the invention. The antibodies, fragments thereof and recombinant antibodies comprising the CDR domains according to the invention may be used in a method of inhibiting or reducing recurrence or metastasis of cancer in a mammal, particularly in a human, comprises administering to said mammal an effective amount of the antibodies, fragments thereof and recombinant antibodies of the invention. The antibodies, fragments thereof and recombinant antibodies comprising the CDR domains according to the invention may be used in a method of inhibiting or blocking stimulation of TGFβ, particularly TGFβ3, in response to radiation or cancer therapy in a mammal, particularly in a human, comprising administering to said mammal an effective amount of the antibodies, fragments thereof and recombinant antibodies of the invention. In an aspect of the method, the TGF-β3 specific antibodies, fragments thereof and recombinant antibodies comprising the CDR domains according to the invention are administered in combination or subsequent to radiation therapy and/or cancer therapy in a mammal.

A therapeutic method of the invention is associated with the prevention or treatment of cancer, or the stimulation or enhancement of immune response to cancer, including melanoma, breast, prostate and lung cancer. In an aspect of the method, the specific TGF-β3 neutralizing antibodies of the invention, including active fragments thereof, serve to stimulate or enhance an immune response to cancer, including melanoma, breast, prostate and lung cancer. In an aspect, immune responses via a cancer vaccine or cancer immunotherapy, including radiation therapy, are stimulated or enhanced by one or more specifically neutralizing TGF-β3 antibody or active fragment thereof of the invention.

The binding members and antibodies of the present invention, and in a particular embodiment the antibody having sequence represented in FIG. 4C, 15, 16, 17, 18 or 19, or active fragments thereof, and single chain, recombinant or synthetic antibodies derived therefrom, particularly comprising the heavy chain CDR region sequences and the light chain CDR region sequences depicted in FIG. 4C, can be prepared in pharmaceutical compositions, including a suitable vehicle, carrier or diluent, or including an adjuvant and/or immune modulator, for administration in instances wherein therapy is appropriate, such as to treat cancer or stimulate or enhance immune response, including immune response against cancer. Such pharmaceutical compositions may also include means for modulating the half-life of the binding members, antibodies or fragments by methods known in the art such as pegylation. Such pharmaceutical compositions may further comprise additional antibodies or therapeutic agents.

A composition of the present invention may be administered alone or in combination with other treatments, therapeutics or agents, either simultaneously or sequentially dependent upon the condition to be treated. In addition, the present invention contemplates and includes compositions comprising the binding member, particularly antibody or fragment thereof, herein described and other agents or therapeutics such as anti-cancer agents or therapeutics, anti-mitotic agents, apoptotic agents or antibodies, or immune modulators, or small molecule inhibitors to immune modulators. More generally these anti-cancer agents may be tyrosine kinase inhibitors or phosphorylation cascade inhibitors, post-translational modulators, cell growth or division inhibitors (e.g. anti-mitotics), inhibitors or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. In addition, the composition may be administered with immune modulators, such as α-galactosyl ceramide, interleukins, tumor necrosis factor (TNF) or other growth factors, colony stimulating factors, cytokines or hormones which stimulate the immune response and reduction or elimination of cancer cells or tumors. The composition may be administered with an immune modulator such as an adjuvant. The composition may also be administered with, or may include combinations along with other anti-TGFβ antibodies, other immunomodulatory antibodies or other anti-tumor antigen antibodies. In an aspect, the composition is administered in combination with another antibody, particularly an anti-tumor antigen antibody.

The present invention also includes antibodies and fragments thereof, which are covalently attached to or otherwise associated with other molecules or agents. These other molecules or agents include, but are not limited to, molecules (including antibodies or antibody fragments) with distinct recognition characteristics, toxins, ligands, and chemotherapeutic agents. In an additional aspect, the antibodies or fragments of the invention may be used to target or direct therapeutic molecules or other agents, for example to target molecules or agents to TGFβ expressing cells, or TGFβ responsive cells, particularly TGF-β3 expressing or responsive cells, for example cells at wound sites, tumor sites, inflammatory areas or cancerous lesions.

The diagnostic utility of the present invention extends to the use of the antibodies of the present invention in assays to characterize tumors or cellular samples or to screen for tumors or cancer, including in vitro and in vivo diagnostic assays. In an immunoassay, a control quantity of the antibodies, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

Specific binding members of the invention may carry a detectable or functional label. The specific binding members may carry a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{121}I$, $^{124}I$, $^{125}I$, $^{131}I$, $^{111}In$, $^{117}Lu$, $^{211}At$, $^{198}Au$, $^{67}Cu$, $^{225}Ac$, $^{213}Bi$, $^{99}Tc$ and $^{186}Re$. When radioactive labels are used, known currently available counting procedures may be utilized to identify and quantitate the specific binding members. In the instance where the label is an enzyme, detection may be accomplished by any of the presently utilized colorimetric, spectrophotometric, fluorospectrophotometric, amperometric or gasometric techniques known in the art.

The radiolabelled specific binding members, particularly antibodies and fragments thereof, are useful in in vitro diagnostics techniques and in in vivo radioimaging techniques. In a further aspect of the invention, radiolabelled specific binding members, particularly antibodies and fragments thereof, particularly radioimmunoconjugates, are useful in radioimmunotherapy, particularly as radiolabelled antibodies for cancer therapy. In a still further aspect, the radiolabelled specific binding members, particularly antibodies and fragments thereof, are useful in radioimmuno-guided surgery techniques, wherein they can identify and indicate the presence and/or location of cancer cells, pre-cancerous cells, tumor cells, and hyperproliferative cells, prior to, during or following surgery to remove such cells.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

The present invention includes an assay system which may be prepared in the form of a test kit for the quantitative analysis of the extent of the presence of, for instance, TGFβ3. The system or test kit may comprise a labeled component prepared by one of the radioactive and/or enzymatic techniques discussed herein, coupling a label to the antibody, and one or more additional immunochemical reagents, at least one of which is a free or immobilized components to be determined or their binding partner(s).

Other objects and advantages will become apparent to those skilled in the art from a review of the ensuing detailed description, which proceeds with reference to the following illustrative drawings, and the attendant claims.

BRIEF DESCRIPTION OF THE DRAWINGS

FIG. 4C provides the CDR1, CDR2 and CDR3 amino acid sequences for the light chain and heavy chain variable regions of each of the TGF-β3 antibodies. AntibodiesTGFβ-3-9/8 (MTGF-β3-9) (CDR SEQ ID NOs:1-3 and 4-6), TGFβ-3-1901/16 (MTGF-β3-19) (CDR SEQ ID NOs:7, 2, 3 and 8, 9, 6) and TGFβ-3-1679/2 (MTGF-β3-16) (CDR SEQ ID NOs:7, 2, 3 and 8, 9, 6) are grouped together and demonstrate very similar CDR1, CDR2 and CDR3 domain sequences. CDR region amino acids that differ are underlined in the TGFβ-3-9/8 (MTGF-β3-9) sequence. The CDR sequences of antibodies TGFβ-3-1203/11 (MTGF-β3-12) (SEQ ID NOs:10-12 and 13-15) and TGFβ-3-1719/13 (MTGF-β3-17) (SEQ ID NOs:16-18 and 19-21) are also depicted, and fall into distinct independent sequence groups.

FIG. 15 depicts the amino acid (SEQ ID NO:23) and nucleic acid (SEQ ID NO:22) sequence of the heavy chain variable region and the amino acid (SEQ ID NO:25) and nucleic acid (SEQ ID NO:24) sequence of the light chain variable region of TGF-β3 antibody MTGF-β3-9.

FIG. 16 depicts the amino acid (SEQ ID NO:27) and nucleic acid (SEQ ID NO:26) sequence of the heavy chain variable region and the amino acid (SEQ ID NO: 29) and nucleic acid (SEQ ID NO:28) sequence of the light chain variable region of TGF-β3 antibody MTGF-β3-12.

FIG. 17 depicts the amino acid (SEQ ID NO:31) and nucleic acid (SEQ ID NO:30) sequence of the heavy chain variable region and the amino acid (SEQ ID NO:33) and nucleic acid (SEQ ID NO:32) sequence of the light chain variable region of TGF-β3 antibody MTGF-β3-16.

FIG. 18 depicts the amino acid (SEQ ID NO:35) and nucleic acid (SEQ ID NO:34) sequence of the heavy chain variable region and the amino acid (SEQ ID NO:37) and nucleic acid (SEQ ID NO:36) sequence of the light chain variable region of TGF-β3 antibody MTGF-β3-17.

FIG. 19 depicts the amino acid (SEQ ID NO:39) and nucleic acid (SEQ ID NO:38) sequence of the heavy chain variable region and the amino acid (SEQ ID NO:41) and nucleic acid (SEQ ID NO:40) sequence of the light chain variable region of TGF-β3 antibody MTGF-β3-19.

DETAILED DESCRIPTION

Figure 1:
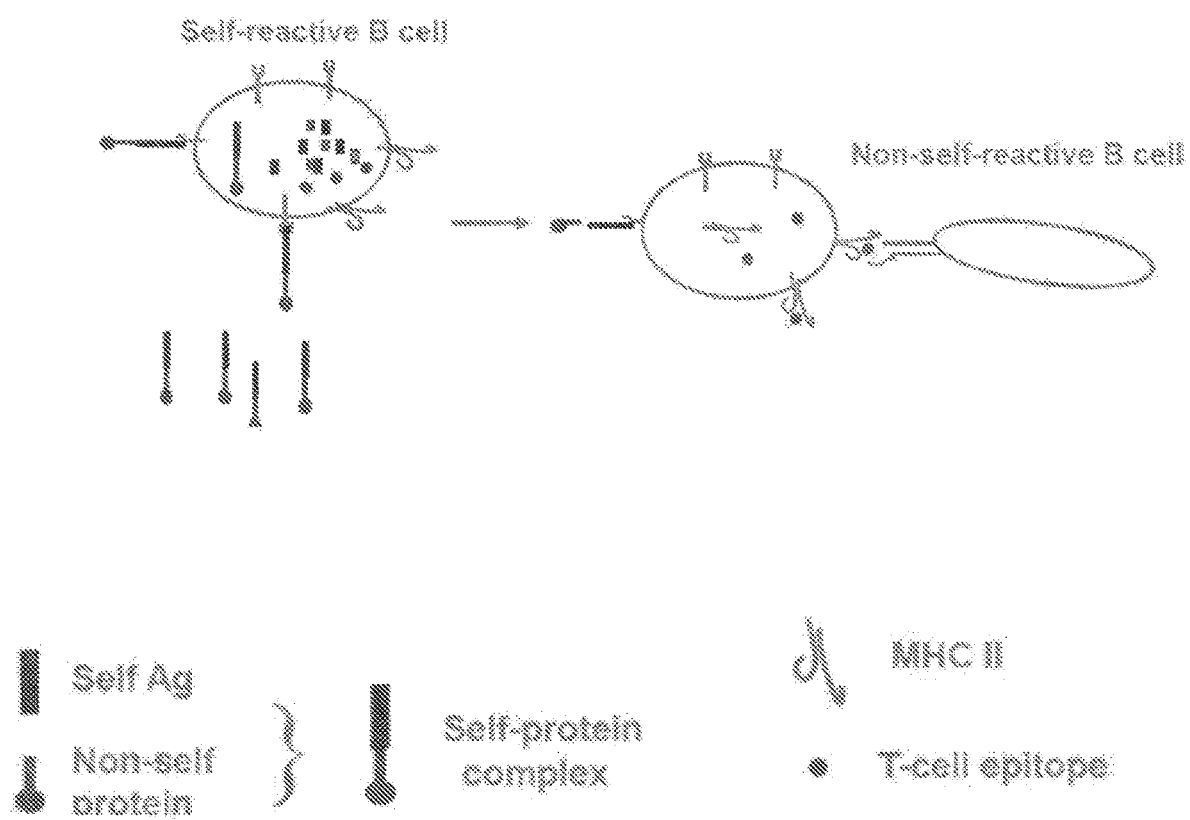
FIG. 1 depicts the approach and rationale for the auto-vaccination procedure to generate antibodies.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. Terminology

The term "TGF-β3" and "TGF-Beta3" refers to and includes both the human and the mouse protein, transforming growth factor beta isoform 3. Exemplary full length amino acid sequences of human and mouse TGF-β3 are provided herein.

The antibody "MTGF-β3-9/8" is also denoted as TGF-β3-9/8 and MTGF-β3-9 TGF-β3-9/8.

The antibody "MTGF-β3-1203/11" is also denoted as TGF-β3-1203/11 and MTGF-β3-12.

The antibody "MTGF-β3-1679/2" is also denoted as TGF-β3-1679/2 and MTGF-β3-16.

The antibody "MTGF-β3-1719/13" is also denoted as TGF-β3-1719/13 and MTGF-β3-17.

The antibody "MTGF-β3-1901/16" is also denoted as TGF-β3-1901/16 and MTGF-β3-19.

The term "specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" are any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv), which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J Immunol. Methods 242: 193-204 9 (2000)); (xii) a minibody, which is a bivalent molecule comprised of scFv fused to constant immunoglobulin domains, CH3 or CH4, wherein the constant CH3 or CH4 domains serve as dimerization domains (Olafsen T et al (2004) Prot Eng Des Sel 17(4):315-323; Hollinger P and Hudson P J (2005) Nature Biotech 23(9): 1126-1136); and (xiii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-cancer or anti-tumor specific antibody. The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine or a toxin (e.g., ricin) or anti-mitotic or apoptotic agent or factor. Thus, the TGFbeta-3 antibodies of the invention may be utilized to direct or target agents, labels, other molecules or compounds or antibodies in indications such as wound healing, inflammation, cancer or tumors.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

Immunoconjugates or antibody fusion proteins of the present invention, wherein the antibodies, antibody molecules, or fragments thereof of use in the present invention are conjugated or attached to other molecules or agents further include, but are not limited to such antibodies, molecules, or fragments conjugated to a chemical ablation agent, toxin, immunomodulator, cytokine, cytotoxic agent, chemotherapeutic agent, antimicrobial agent or peptide, cell wall and/or cell membrane disrupter, or drug.

The term "adjuvant(s)" describes a substance, compound, agent or material useful for improving an immune response or immune cell or component stimulation, and may in some instances be combined with any particular antigen in an immunological, pharmaceutical or vaccine composition. Adjuvants can be used to increase the amount of antibody and effector T cells produced and to reduce the quantity of antigen or immune stimulant or modulator and the frequency of injection. Although some antigens are administered without an adjuvant, there are many antigens that lack sufficient immunogenicity to stimulate a useful immune response in the absence of an effective adjuvant. Adjuvants also improve the immune response from "self-sufficient" antigens, in that the immune response obtained may be increased or the amount of antigen administered may be reduced. An adjuvant can serve as a tissue depot that slowly releases the antigen and also as a lymphoid system activator that non-specifically enhances the immune response (Hood et al., *Immunology, Second Ed.,* 1984, Benjamin/Cummings: Menlo Park, Calif., p. 384). In a preferred aspect an adjuvant is physiologically and/or pharmaceutically acceptable in a mammal, particularly a human. The standard adjuvant for use in laboratory animals is Freund's adjuvant. Freund's Complete adjuvant (FCA) is an emulsion containing mineral oil and killed mycobacteria in saline. Freund's incomplete adjuvant (FIA) omits the mycobacteria. Both FIA and FCA induce good humoral (antibody) immunity, and FCA additionally induces high levels of cell-mediated immunity. However, neither FCA nor FIA are acceptable for clinical use due to the side effects. In particular, mineral oil is known to cause granulomas and abscesses, and *Mycobacterium tuberculosis* is the agent responsible for tuberculosis. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight). There have been many substances that have been tried to be used as adjuvants, such as the lipid-A portion of gram negative bacterial endotoxin, and trehalose dimycolate of mycobacteria. The phospholipid lysolecithin exhibited adjuvant activity (Arnold et al., Eur. J Immunol. 9:363-366, 1979). Some synthetic surfactants exhibited adjuvant activity, including dimethyldioctadecyl ammonium bromide (DDA) and certain linear polyoxypropylenepolyoxyethylene (POP-POE) block polymers (Snippe et al., Int. Arch. Allergy Appl. Immunol. 65:390-398, 1981; and Hunter et al., J. Immunol. 127:1244-1250, 1981).

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "comprise" generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy.

As used herein, "pg" means picogram, "ng" means nanogram, "ug" or "µg" mean microgram, "mg" means milligram, "ul" or "µl" mean microliter, "ml" means milliliter, "l" means liter.

The terms "antibody", "anti-TGFβ3 antibody", "TGF-beta3 antibody", "TGF-β3 antibody", "human/mouse TGFβ3 antibody", and any variants not specifically listed, may be used herein interchangeably, and as used throughout the present application and claims refer to proteinaceous material including single or multiple proteins, and extends to those proteins having the amino acid sequence data described herein and presented in FIGS. 4C, 15, 16, 17, 18 and 19 and the profile of activities set forth herein and in the Claims. Exemplary such TGFβ3 antibodies provided herein include antibodies MTGF-β3-9, MTGF-β3-12, MTGF-β3-16, MTGF-β3-17 and MTGF-β3-19 as provided and characterized herein. Antibodies provided herein extend to antibodies or proteins, including antibody fragments, having the amino acid sequence data described herein and presented in FIGS. 4C, 15, 16, 17, 18 and 19, including CDR sequences SEQ ID NOs:1-21 and variable region sequences SEQ ID NOs:23, 25, 27, 29, 31, 33, 35, 37, 39 and 41, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "antibody", "anti-TGFβ3 antibody", "TGFbeta3 antibody", "TGF-β3 antibody", "human/mouse TGFβ3 antibody", and the exemplary antibodies MTGF-β3-9, MTGF-β3-12, MTGF-β3-16, MTGF-β3-17 and MTGF-β3-19, are intended to include within their scope proteins specifically recited herein as well as all substantially homologous analogs and allelic variations.

In an aspect of the invention and particularly provided herein are antibodies which are specific to the TGF-beta isoform TGF-β3. Such specific TGF-β3 antibodies bind and recognize TGF-β3 isoform, and do not, or do not significantly, bind or recognize alternative TGF-β isoforms, particularly TGF-β1 and TGF-β2. TGF-β3 specific antibodies of the invention are exemplified by antibodies MTGF-β3-9, MTGF-β3-12, MTGF-β3-16 and MTGF-β3-19.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art.

It should be appreciated that also within the scope of the present invention are DNA sequences encoding specific binding members (antibodies) of the invention which code for e.g. an antibody having amino acid sequence as provided in FIG. 15, 16, 17, 18 or 19, or comprising the CDR domain region sequences set out herein or in FIG. 4C, 15, 16, 17, 18 or 19, but which are degenerate thereto. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in the sequences encoding the amino acids, antibody fragments, CDR region sequences set out in FIGS. 4C, 15, 16, 17, 18 and 19, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (for example, by changing the codon from an amino acid belonging to a grouping of amino acids having a particular size or characteristic to an amino acid belonging to another grouping) or in a conservative manner (for example, by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention includes sequences containing amino acid changes and substitutions, including conservative changes, which do not significantly alter the activity or binding characteristics of the resulting protein.

The following is one example of various groupings of amino acids:
Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at pH 6.0)
Aspartic acid, Glutamic acid
Basic Amino Acids (Positively Charged at pH 6.0)
Lysine, Arginine, Histidine (at pH 6.0)

Another grouping may be those amino acids with phenyl groups: Phenylalanine, Tryptophan, Tyrosine Another grouping may be according to molecular weight (i.e., size of R groups):

| | | | |
|---|---|---|---|
| Glycine | 75 | Alanine | 89 |
| Serine | 105 | Proline | 115 |
| Valine | 117 | Threonine | 119 |
| Cysteine | 121 | Leucine | 131 |
| Isoleucine | 131 | Asparagine | 132 |
| Aspartic acid | 133 | Glutamine | 146 |
| Lysine | 146 | Glutamic acid | 147 |
| Methionine | 149 | Histidine (at pH 6.0) | 155 |
| Phenylalanine | 165 | Arginine | 174 |
| Tyrosine | 181 | Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "highly homologous" or "substantially homologous" when at least about 70% of the amino acid residues (preferably at least about 80%, and most preferably at least about 90 or 95%) are identical, or represent conservative substitutions. The CDR regions of two antibodies are substantially homologous when one or more amino acids, or one or a few, or one to three, or one or two are substituted with a similar or conservative amino acid substitution, and wherein the antibody/antibodies have the profile of binding and activities of one or more of the antibodies, particularly one or more of antibody MTGF-β3-9, MTGF-β3-12, MTGF-β3-16, MTGF-β3-17 and/or MTGF-β3-19 disclosed herein. An antibody may be substantially homologous wherein one, two or three amino acids, or up to three amino acids, wherein one, two, three or four, or up to four amino acids, in the CDR domain regions are substituted with another amino acid and wherein the antibody retains the profile of antibody binding and activities.

Exemplary CDR domain region amino acid substitutions are provided herein. Thus, in accordance with the invention TGF-β3 antibodies, particularly TGF-β3 specific antibodies, are provided having heavy chain variable region CDRs wherein the CDR1 domain comprises a sequence SSWXH wherein X is either M or I (SEQ ID NO:42), the CDR2 domain comprises a sequence $RIX_1PGDGDTX_2YX_3GX_4FKG$ wherein $X_1$ is F or Y, $X_2$ is I or N, $X_3$ is N or T and $X_4$ is N or K (SEQ ID NO:43), and the CDR3 domain comprises a sequence RMITTQAAMDY (SEQ ID NO:6). In an aspect of the invention, TGF-β3 antibodies, particularly TGF-β3 specific antibodies, are provided having heavy chain variable region CDRs wherein the CDR1 domain comprises a sequence SSWXH (SEQ ID NO:42) wherein X is either M or I or another amino acid, the CDR2 domain comprises a sequence $RIX_1PGDGDTX_2YX_3GX_4FKG$ (SEQ ID NO:43) wherein $X_1$ is F or Y or another amino acid, $X_2$ is I or N or another amino acid, $X_3$ is N or T or another amino acid, and $X_4$ is N or K or another amino acid, and the CDR3 domain comprises a sequence RMITTQAAMDY (SEQ ID NO; 6). In another aspect, the invention provides TGF-β3 antibodies, particularly TGF-β3 specific antibodies, comprising light chain variable region CDRs wherein the CDR1 domain comprises a sequence KASQSVINXVA wherein X is either D or A (SEQ ID NO:44), the CDR2 domain comprises a sequence YASNRT (SEQ ID NO:2), and the CDR3 domain comprises a sequence QQDYSSPYT (SEQ ID NO:3). In a further aspect, TGF-β3 antibodies, particularly TGF-β3 specific antibodies, comprising light chain variable region CDRs wherein the CDR1 domain comprises a sequence KASQSVINXVA (SEQ ID NO:44) wherein X is either D or A or another amino acid, the CDR2 domain comprises a sequence YASNRT (SEQ ID NO:2), and the CDR3 domain comprises a sequence QQDYSSPYT (SEQ ID NO:3), are included in the invention.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "agent" means any molecule, including polypeptides, antibodies, polynucleotides, chemical compounds and small molecules. In particular the term agent includes compounds such as test compounds or drug candidate compounds.

The term "agonist" refers to a ligand that stimulates the receptor the ligand binds to in the broadest sense.

The term "assay" means any process used to measure a specific property of a compound. A "screening assay" means a process used to characterize or select compounds based upon their activity from a collection of compounds.

The term "preventing" or "prevention" refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term "prophylaxis" is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Therapeutically effective amount" means that amount of a drug, compound, antimicrobial, antibody, or pharmaceutical agent that will elicit the biological or medical response of a subject that is being sought by a medical doctor or other clinician. In particular, with regard to gram-positive bacterial infections and growth of gram-positive bacteria, the term "effective amount" is intended to include an effective amount of a compound or agent that will bring about a biologically meaningful decrease in the amount of or extent of tumor regression and or increase in length of a subject's survival or period disease-free or in remission. The phrase "therapeutically effective amount" is used herein to mean an amount sufficient to prevent, and preferably reduce by at least about 30 percent, more preferably by at least 50 percent, most preferably by at least 90 percent, a clinically significant change in the growth or amount of tumor size, or enhanced survival or disease-free period by at least about 30 percent, more preferably by at least 50 percent, most preferably by at least 90 percent.

The term "treating" or "treatment" of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or infection, either physically, (e.g., stabilization of a discernible symptom), physiologically, (e.g., stabilization of a physical parameter), or both. In a further embodiment, "treating" or "treatment" relates to slowing the progression of a disease or reducing an infection.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, "pg" means picogram, "ng" means nanogram, "ug" or "µg" mean microgram, "mg" means milligram, "ul" or "µl" mean microliter, "ml" means milliliter, "l" means liter.

B. Detailed Disclosure

The invention provides antibodies directed against transforming growth factor beta 3 (TGF-β3) for diagnostic and therapeutic purposes. In particular, antibodies specific for TGF-β3 are provided, wherein said antibodies recognize and are capable of binding human and mouse TGF-β3, and do not recognize or bind other TGF beta forms, particularly the antibodies do not recognize or bind TGF-β1 or TGF-β2. Exemplary TGF-β3 antibodies are particularly provided herein. Exemplary antibodies include antibodies MTGF-β3-9, MTGF-β3-12, MTGF-β3-16, MTGF-β3-17 and MTGF-β3-19. The invention particularly provides an antibody or active fragment thereof that recognizes and neutralizes TGF-β3, particularly wherein said antibody or active fragment does not recognize or neutralize TGF-β1 or TGF-β2. Exemplary antibodies capable of specifically recognizing TGF-β3 and neutralizing TGF-β3 include antibodies MTGF-β3-9, MTGF-β3-12, MTGF-β3-16 and MTGF-β3-19.

The antibodies of the present invention have diagnostic and therapeutic use in immune modulation and cancer. In a particular aspect the antibodies of the invention are applicable in cancers, including but not limited to adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In particular, the antibodies are applicable in melanoma, breast, prostat or lung cancer.

In a general aspect, the present invention provides TGF-β3 antibodies directed against human and mouse TGF-β3, which neutralize TGF-β3 activity. In one such aspect, the invention provides TGF-β3 antibodies MTGF-β3-9, MTGF-β3-12, MTGF-β3-16, MTGF-β3-17 and MTGF-β3-19. The present invention provides TGF-β3 antibodies directed against human and mouse TGF-β3, which do not cross react with or bind to TGF-β1 and/or TGF-β3 and which specifically neutralize TGF-β3 activity. In a particular spect, antibody of the present invention blocks TGF-β3-mediated signaling and/or TGF-β3 mediated cell response or cell proliferation. In a particular aspect, the invention provides anti-TGF-β3 specific antibodies MTGF-β3-9, MTGF-β3-12, MTGF-β3-16 and MTGF-β3-19. In a further particular aspect the invention provides TGF-β3 specific antibody capable of specifically binding and neutralizing TGF-β3 comprising the heavy chain amino acid sequence as set out in FIG. 15, 16, 17, 18 or 19.

In one such aspect, the invention provides a TGF-β3 antibody comprising the heavy chain variable region CDR sequences set out in FIG. 4C. In an aspect thereof, TGF-β3 specific antibody is provided having a heavy chain variable region comprising the CDR 1, CDR2 and CDR3 domain amino acid sequences of SSWMH (SEQ ID NO:4) or SSWIH (SEQ ID NO:8), RIFPGDGDTIYNGNFKG (SEQ ID NO:5) or RIYPGDGDTNYTGKFKG (SEQ ID NO:9), and RMITTQAAMDY (SEQ ID NO:6), respectively. In an aspect thereof, TGF-β3 specific antibody is provided having a heavy chain variable region comprising the CDR 1, CDR2 and CDR3 domain amino acid sequences of DYYIN (SEQ ID NO:13), KIGPGTGRTYYNEKFKG (SEQ ID NO:14), and YYGWGYAMDY (SEQ ID NO:15), respectively. In an aspect, TGF-β3 antibody is provided having a heavy chain variable region comprising the CDR 1, CDR2 and CDR3 domain amino acid sequences SYWIT (SEQ ID NO:19), DIFPGTGSTNYNEKFKT (SEQ ID NO:20), and KLGPNYAVDY (SEQ ID NO:21) respectively.

The TGF-β3 antibody may comprise heavy chain variable region comprising the heavy chain CDR domain region CDR1, CDR2 and CDR3 sequences of FIG. 4C, and a light chain variable region. In an aspect, the TGF-β3 antibody comprises the light chain variable region CDR sequences set out in FIG. 4C. TGF-β3 specific antibody is provided having a light chain variable region comprising the CDR 1, CDR2 and CDR3 domain amino acid sequences of KASQSVINDVA (SEQ ID NO:1) or KASQSVINAVA (SEQ ID NO:7), YASNRYT (SEQ ID NO:2), and QQDYSSPT (SEQ ID NO:3), respectively, or of KSSQSLLNSGNQKNYLA (SEQ ID NO:10), GASTRES (SEQ ID NO:11), and QNDHGFPLT (SEQ ID NO:12), respectively.

In another aspect, the invention provides an antibody directed against TGF-β3 comprising:
(a) a light chain variable region comprising a CDR1 sequence KASQSVINDVA (SEQ ID NO:1) or KASQSVINAVA (SEQ ID NO:7), a CDR2 sequence YASNRYT (SEQ ID NO:2), and a CDR3 sequence QQDYSSPT (SEQ ID NO:3), and a heavy chain variable region sequence comprising a CDR1 sequence SSWMH (SEQ ID NO:4) or SSWIH (SEQ ID NO:8), a CDR2 sequence RIFPGDGDTIYNGNFKG (SEQ ID NO:5) or RIYPGDGDTNYTGKFKG (SEQ ID NO:9), and a CDR3 sequence RMITTQAAMDY (SEQ ID NO:6);
(b) a light chain variable region comprising a CDR1 sequence KSSQSLLNSGNQKNYLA (SEQ ID NO:10), a CDR2 sequence GASTRES (SEQ ID NO:11), and a CDR3 sequence QNDHGFPLT (SEQ ID NO:12), and a heavy chain variable region sequence comprising a CDR1 sequence DYYIN (SEQ ID NO:13), a CDR2 sequence KIGPGTGRTYYNEKFKG (SEQ ID NO:14), and a CDR3 sequence YYGWGYAMDY (SEQ ID NO:15); or
(c) a light chain variable region comprising a CDR1 sequence RSSQSLIHSHGNTYLH (SEQ ID NO:16), a CDR2 sequence KLSNRFS (SEQ ID NO:17), and a CDR3 sequence SQSTHVPFT (SEQ ID NO:18), and a heavy chain variable region sequence comprising a CDR1 sequence SYWIT (SEQ ID NO:19), a CDR2 sequence DIFPGTGSTNYNEKFKT (SEQ ID NO:20), and a CDR3 sequence KLGPNYAVDY (SEQ ID NO:21).

In another aspect of the invention, provided herein is an antibody(ies) or fragment(s) thereof that binds to the same epitope of TGF-β3 (such as particularly, human TGF-β3) as the antibody(ies) described herein. In another embodiment, provided herein is an antibody(ies) or antigen-binding fragment(s) thereof that competes with an antibody or antigen-binding fragment thereof described herein for binding to TGF-β3 (e.g., human TGF-β3). In a specific embodiment, provided herein is an antibody(ies) or antigen-binding fragment(s) thereof that competes with antibody or antigen-binding fragment thereof described herein for binding to TGF-β3 (e.g., human TGF-β3) to the extent that the antibody or antigen-binding fragment thereof described herein self-competes for binding to TGF-β3 (e.g., human TGF-β3).

In another specific embodiment, provided herein is a first antibody or antigen-binding fragment thereof that competes with an antibody or antigen-binding fragment thereof described herein for binding to TGF-β3 (e.g., human TGF-β3), wherein the first antibody or antigen-binding fragment thereof competes for binding in an assay comprising the following steps: (a) incubating TGF-β3 coated ELISA plates with the first antibody or antigen-binding fragment thereof in unlabeled form; (b) adding labeled antibody or antigen-binding fragment thereof described herein to the TGF-β3 coated ELISA plates and incubating TGF-β3 coated ELISA plates; and (c) detecting the binding of the antibody or antigen-binding fragment thereof described herein to TGF-β3. In an aspect, binding of an antibody TGFβ3-9 or antigen binding fragment thereof, antibody TGFβ3-19 or antigen binding fragment thereof, antibody TGFβ3-16 or antigen binding fragment thereof, or antibody TGFβ3-12 or antigen binding fragment thereof is detected after incubation with the first antibody or antigen binding fragment thereof. In an aspect, provided herein is a first antibody or antigen-binding fragment thereof that competes with an antibody or antigen-binding fragment thereof described herein for binding to TGF-β3 (e.g., human TGF-β3), wherein the first antibody or antigen-binding fragment thereof competes for binding in an assay comprising the following steps: (a) incubating TGF-β3 coated ELISA plates with the first antibody or antigen-binding fragment thereof in unlabeled form; (b) adding the biotinylated antibody or antigen-binding fragment thereof described herein to the TGF-β3 coated ELISA plates and incubating TGF-β3 coated ELISA plates; and (c) detecting the binding of the antibody or antigen-binding fragment thereof described herein to TGF-β3. In an aspect hereof, the labeled or biotinylated antibody or antigen binding fragment thereof is selected from antibody TGFβ3-9 or antigen binding fragment thereof, antibody TGFβ3-19 or antigen binding fragment thereof, antibody TGFβ3-16 or antigen binding fragment thereof, or antibody TGFβ3-12 or antigen binding fragment thereof. In an aspect, binding of antibody or antigen binding fragment of one or more of TGFβ3-9, TGFβ3-19, TGFβ3-16 or TGFβ3-12 is reduced, in particular is significantly reduced, in the presence of first antibody or antigen-binding fragment thereof in unlabeled form.

In another specific embodiment, provided herein is a first antibody or antigen-binding fragment thereof that competes with an antibody or antigen-binding fragment thereof described herein for binding to TGF-β3 (e.g., human TGF-β3), wherein the competition is exhibited as reduced binding of first antibody or antigen-binding fragment thereof to TGF-β3 (e.g., human TGF-β3) by more than 60% (e.g., 65%, 70%, 75%, 85%, 90%, 95%, or 98%, or between 60% to 65%, 65% to 70%, 70% to 75%, 75% to 80%, 80% to 85%, 85% to 95%, or 95% to 100%). In another specific embodiment, provided herein is a first antibody or antigen-binding fragment thereof that competes with an antibody or antigen-binding fragment thereof described herein for binding to TGF-β3 (e.g., human TGF-β3), wherein the competition is exhibited as reduced binding of antibody or antigen binding fragment of one or more of TGFβ3-9, TGFβ3-19, TGFβ3-16 or TGFβ3-12 by more than 60% (e.g., 65%, 70%, 75%, 85%, 90%, 95%, or 98%, or between 60% to 65%, 65% to 70%, 70% to 75%, 75% to 80%, 80% to 85%, 85% to 95%, or 95% to 100%) in the presence and/or after binding of the first antibody or antigen-binding fragment thereof.

In specific aspects, provided herein is an antibody which competes (e.g., in a dose dependent manner) for specific binding to TGF-β3 (e.g., human TGF-β3), with an antibody comprising (i) a VL domain comprising a VL CDR1, VL CDR2, and VL CDR3 having the amino acid sequences of the VL CDRs of an antibody listed in FIG. 4C; and (ii) a VH domain comprising a VH CDR1, VH CDR2, and VH CDR3 having the amino acid sequences of the CDRs of an antibody listed in FIG. 4C.

In a particular embodiment, provided herein is an antibody that competes (e.g., in a dose-dependent manner), for specific binding to TGF-β3 (e.g., human TGF-β3), with an antibody comprising the VH and VL CDRs of TGF-β3-9 (SEQ ID NO: 4, 5, 6 and 1, 2, 3). In a particular embodiment, provided herein is an antibody that competes, for specific binding to TGF-β3 (e.g., human TGF-β3), with an antibody comprising the VH and VL CDRs of TGF-β3-19 (SEQ ID NO: 8, 9, 6 and 7, 2, 3).

In a particular embodiment, provided herein is an antibody that competes, for specific binding to TGF-β3 (e.g., human TGF-β3), with an antibody comprising the VH and VL CDRs of TGF-β3-16 (SEQ ID NO: 8, 9, 6 and 7, 2, 3).

In a particular embodiment, provided herein is an antibody that competes, for specific binding to TGF-β3 (e.g., human TGF-β3), with an antibody comprising the VH and VL CDRs of TGF-β3-12 (SEQ ID NO: 13, 14, 15 and 10, 11, 12).

In a specific embodiment, an antibody described herein is one that is competitively blocked (e.g., in a dose dependent manner) by an antibody comprising a VL domain having the amino acid sequence selected from the group consisting of SEQ ID NO: 1, 2, 3, 7, 10, 11 12 and a VH domain having the amino acid sequence selected from the group consisting of SEQ ID NO: 4, 5, 6, 8, 9, 13, 14 and 15, for specific binding to TGF-β3 (e.g., human TGF-β3).

In specific aspects, provided herein is an antibody, or an antigen-binding fragment thereof, which immunospecifically binds to the same epitope as that of an antibody (e.g., TGF-β3-9, TGF-β3-19, TGF-β3-16, TGF-β3-12) comprising the amino acid sequences described herein (see, e.g., FIG. 4C) for specific binding to TGF-β3 (e.g., human TGF-β3). Assays known to one of skill in the art or described herein (e.g., X-ray crystallography, ELISA assays, etc.) can be used to determine if two antibodies bind to the same epitope.

In a specific embodiment, an antibody or an antigen-binding fragment thereof described herein immunospecifically binds to the same epitope as that of an antibody (e.g., TGF-β3-9, TGF-β3-19, TGF-β3-16, TGF-β3-12) comprising a VL domain having an amino acid sequence selected from the group consisting of SEQ ID NO: 1, 2, 3, 7, 10, 11 12, and a VH domain having an amino acid sequence selected from the group consisting of SEQ ID NO: 5, 6, 8, 9, 13, 14 and 15).

In a specific embodiment, an antibody or an antigen-binding fragment thereof described herein immunospecifically binds to the same epitope as that bound by an antibody comprising the VH domain and VL domain of antibody TGF-β3-9, TGF-β3-19, TGF-β3-16, TGF-β3-12 (SEQ ID NOs: 1, 2, 3 and 4, 5, 6 or SEQ ID Nos: 7, 2, 3 and 8, 9, 6 or SEQ ID Nos: 10, 11, 12 and 13, 14, 15 respectively), or an epitope that overlaps the epitope of antibody comprising the VH domain and VL domain of antibody TGF-β3-9, TGF-β3-19, TGF-β3-16, TGF-β3-12 (SEQ ID NOs: 1, 2, 3 and 4, 5, 6 or SEQ ID Nos: 7, 2, 3 and 8, 9, 6 or SEQ ID Nos: 10, 11, 12 and 13, 14, 15 respectively).

Panels of monoclonal antibodies recognizing human and murine TGF-β3 can be screened for various properties; i.e., isotype, epitope, affinity, etc. Of particular interest are antibodies that mimic the activity of exemplary antibodies MTGF-β3-9, MTGF-β3-16 and MTGF-β3-19, and have affinity for human and mouse TGF-β3, do not react with TGF-β1 or TGF-β2, and directly affect the activity of TGF-β3, in particular neutralize TGF-β3. Such antibodies can be readily identified and/or screened in specific binding member activity assays.

A monoclonal antibody of the present invention may comprise heavy chain variable region, such as exemplified in FIG. 15, 16, 17, 18 or 19, and optionally light chain variable region. In general, the CDR regions, comprising amino acid sequences substantially as set out as the CDR regions of FIG. 4C will be carried in a structure which allows for binding of the CDR regions to the TGF-β3, and particularly to human and mouse TGF-β3.

By "substantially as set out" it is meant that variable region sequences, and/or particularly the CDR sequences, of the invention will be either identical or highly homologous to the specified regions of FIGS. 4C, 15, 16, 17, 18 and/or 19. By "highly homologous" it is contemplated that only a few substitutions, preferably from 1 to 8, preferably from 1 to 5, preferably from 1 to 4, or from 1 to 3, or 1 or 2 substitutions may be made in the variable region sequence and/or in the CDR sequences. The term substantially set out as includes particularly conservative amino acid substitutions which do not materially or significantly affect the specificity and/or activity of the instant antibodies. Conservative and non-conservative amino acid substitutions are contemplated herein for the variable region sequences and also for the CDR region sequences.

Substitutions may be made in the variable region sequence outside of the CDRs so as to retain the CDR sequences. Thus, changes in the variable region sequence or alternative non-homologous or veneered variable region sequences may be introduced or utilized, such that the CDR sequences are maintained and the remainder of the variable region sequence may be substituted.

Alternatively, substitutions may be made particularly in the CDRs. Exemplary CDR sequences for antibody, particularly antibody MTGF-β3-9, MTGF-β3-12, MTGF-β3-16, MTGF-β3-17 and MTGF-β3-19, of the present invention are set out and described herein including in FIG. 4C and in SEQ ID NOs:1-21. The exemplary CDR sequences include substitutions in the CDR sequences. Antibodies of the invention having substitutions as above described and contemplated are selected to maintain the activities and specificity commensurate with the exemplary antibodies, including antibody MTGF-β3-9, MTGF-β3-12, MTGF-β3-16, MTGF-β3-17 and/or MTGF-β3-19 and having the characteristics as set out herein and in the claims.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as provided herein and/or known to those of skill in the art.

Although in a preferred aspect of the invention specific binding members comprising a pair of binding domains based on sequences substantially set out in FIG. 4C, 15, 16, 17, 18 or 19 are preferred, single binding domains based on these sequences, particularly based on the heavy chain and light chain CDRs, form further aspects of the invention. In the case of the binding domains based on the sequence substantially set out in FIG. 4C, 15, 16, 17, 18 or 19, such binding domains may be used as targeting agents for TGF- β3, since it is known that immunoglobulin VH domains are capable of binding target antigens in a specific manner.

Portions or domains of the antibodies of the invention are contemplated and incorporated, including any portion or domain, including those modified or fused to reagents, labels or other domains or fragments, wherein the portions or domains retain the characteristics of the antibodies hereof, including TGF-β3 specific binding, and optionally including TGF-β3 specific neutralization, as exemplified in antibody MTGF-β3-9, MTGF-β3-12, MTGF-β3-16 and MTGF-β3-19 hereof. Antibodies and antibody fragments of the invention include smaller recombinant antibody fragments (for example, classic monovalent antibody fragments (Fab, scFv) and engineered variants (diabodies, triabodies, minibodies and single-domain antibodies) that retain the targeting specificity of the whole antibodies (mAbs) (for review see Hollinger P and Hudson P J (2005) Nature Biotech 23(9):1126-1136). These include for example domain antibody (dAb) fragment, which comprises a single variable domain (Ward, E. S. et al., Nature 341, 544-546 (1989)); camelid antibody; isolated complementarity determining region (CDR); Single Chain Fv Fragments wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); a linear antibody, which comprises a pair of tandem Fv segments (VH-CH1-VH-CH1) which, together with complementarity light chain polypeptides, form a pair of antigen binding regions; multivalent antibody fragments (scFv dimers, trimers and/or tetramers (Power and Hudson, J Immunol. Methods 242: 193-204 9 (2000)); and minibody, which is a bivalent molecule comprised of scFv fused to constant immunoglobulin domains, CH3 or CH4 (for example IgG1 (CH3) and IgE (CH4)), wherein the constant CH3 or CH4 domains serve as dimerization domains (Olafsen T et al (2004) Prot Eng Des Sel 17(4): 315-323; Hollinger P and Hudson P J (2005) Nature Biotech 23(9):1126-1136). These smaller antibodies and engineered variants or fragments can be produced more economically and may possess other unique and superior properties for a range of diagnostic and therapeutic applications. For example, scFV2-Fc can accumulate in higher abundance in tumor or tissue, and a minibody is approximately 80 kD and may be ideal for therapy because of higher uptake in tissues, have faster clearance and have better tissue to blood ratios than intact immunoglobulin (150 kDa) or Fab'2 (110 kDa). The antibody fragments may be forged into multivalent and multispecific reagents, linked to therapeutic payloads (such as radionuclides, toxins, enzymes, liposomes and viruses) and engineered for enhanced therapeutic efficacy. Recently, single antibody domains have been engineered and selected as targeting reagents against hitherto immunosilent cavities in enzymes, receptors and infectious agents.

Specific binding members of the present invention may further comprise antibody constant regions or parts thereof. For example, specific binding members based on the sequences of FIGS. 4C, 15, 16, 17, 18 and/or 19 may be attached at their C-terminal end to antibody light chain constant domains including human Cκ or Cλ chains, preferably Cλ chains. Similarly, specific binding members based on the sequences of FIG. 1 may be attached at their C-terminal end to all or part of an immunoglobulin heavy chain derived from any antibody isotype, e.g. IgG, IgA, IgE, IgD and IgM and any of the isotype sub-classes, particularly IgG1, IgG2b, and IgG4. IgG1 is preferred.

The antibodies, or any fragments thereof, may be conjugated or recombinantly fused to any cellular toxin, bacterial or other, e.g. pseudomonas exotoxin, ricin, or diphtheria toxin. The part of the toxin used can be the whole toxin, or any particular domain of the toxin. Such antibody-toxin molecules have successfully been used for targeting and therapy of different kinds of cancers, see e.g. Pastan, Biochim Biophys Acta. 1997 Oct. 24; 1333(2):C1-6; Kreitman et al., N Engl J Med. 2001 Jul. 26; 345(4):241-7; Schnell et al., Leukemia. 2000 January; 14(1):129-35; Ghetie et al., Mol Biotechnol. 2001 July; 18(3):251-68.

Bi- and tri-specific multimers can be formed by association of different scFv molecules and have been designed as cross-linking reagents for T-cell recruitment into tumors (immunotherapy), viral retargeting (gene therapy) and as red blood cell agglutination reagents (immunodiagnostics), see e.g. Todorovska et al., J Immunol Methods. 2001 Feb. 1; 248(1-2):47-66; Tomlinson et al., Methods Enzymol. 2000; 326:461-79; McCall et al., J Immunol. 2001 May 15; 166(10):6112-7.

Fully human antibodies can be prepared by immunizing transgenic mice carrying large portions of the human immunoglobulin heavy and light chains. These mice, examples of such mice are the XenoMouse® (Abgenix, Inc.) (U.S. Pat. Nos. 6,075,181 and 6,150,584), the HuMAb-Mouse® (Medarex, Inc./GenPharm) (U.S. Pat. Nos. 5,545,806 and 5,569,825), the TRANSCHROMO MOUSE™ (Kirin) and the KM MOUSE™ (Medarex/Kirin), are well known within the art. Antibodies can then be prepared by, e.g. standard hybridoma technique or by phage display. These antibodies will then contain only fully human amino acid sequences. Fully human antibodies can also be generated using phage display from human libraries. Phage display may be performed using methods well known to the skilled artisan, and as provided herein as in Hoogenboom et al and Marks et al (Hoogenboom H R and Winter G. (1992) J Mol Biol. 227(2):381-8; Marks J D et al (1991) J Mol Biol. 222(3): 581-97; and also U.S. Pat. Nos. 5,885,793 and 5,969,108).

Antibodies of the invention may be labelled with a detectable or functional label. Detectable labels include, but are not limited to, radiolabels such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{121}$I, $^{124}$I, $^{125}$I, $^{131}$I, $^{111}$In, $^{117}$Lu, $^{211}$At, $^{198}$Au, $^{67}$Cu, $^{225}$Ac, $^{213}$Bi, $^{99}$Tc and $^{186}$Re, which may be attached to antibodies of the invention using conventional chemistry known in the art of antibody imaging. Labels also include fluorescent labels (for example fluorescein, rhodamine, Texas Red) and labels used conventionally in the art for MRI-CT imaging. They also include enzyme labels such as horseradish peroxidase, β-glucoronidase, β-galactosidase, urease. Labels further include chemical moieties such as biotin which may be detected via binding to a specific cognate detectable moiety, e.g. labelled avidin. Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., MALDI mass spectrometry), array-based oligo-peptide scanning assays, and/or mutagenesis mapping (e.g., site-directed mutagenesis mapping).

In certain aspects, competition binding assays can be used to determine whether an antibody is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with an antibody described herein (e.g. MTGF-β3-9, MTGF-β3-19, MTGF-β3-16, MTGF-β3-12)

In addition, antibodies that recognize and bind to the same or overlapping epitopes of TGF-β3 (e.g., human TGF-β3) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an antigen or an epitope, including a particular epitope on an antigen or protein target. Competitive binding can be determined in an assay in which the immunoglobulin under test inhibits specific binding of another antibody to a common antigen or target antigen. In an aspect, in competition binding, the binding of an antibody or antigen-binding fragment of the present invention, including a TGFβ3 antibody described herein, for example including MTGF-β3-9, MTGF-β3-19, MTGF-β3-16, or MTGF-β3-12, is reduced in the presence of the immunoglobulin under test, and thus competitive binding is assessed and determined and/or confirmed.

In certain aspects, competition binding assays can be used to determine whether an antibody is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with a TGF-β3 antibody described herein, for example including MTGF-β3-9, MTGF-β3-19, MTGF-β3-16, or MTGF-β3-12. Competition binding assays are well known in the art. Exemplary competitive binding assays are provided herein. For example, competition is demonstrated between antibodies herein, including as described in Example 3 and provided in FIG. 6.

In specific aspects, provided herein are antibodies, or an antigen-binding fragments thereof, which binds to the same epitope as that of an antibody (e.g., any one of antibodies MTGF-β3-9, MTGF-β3-19, MTGF-β3-16, MTGF-β3-12) comprising the amino acid sequences described herein (see, e.g., FIG. 4C) for specific binding to TGF-β3 (e.g., human TGF-β3). In specific aspects, provided herein are antibodies, or an antigen-binding fragments thereof, which bind to an overlapping epitope with that of an antibody (e.g., any one of antibodies MTGF-β3-9, MTGF-β3-19, MTGF-β3-16, MTGF-β3-12) comprising the amino acid sequences described herein (see, e.g., FIG. 4C) for specific binding to TGF-β3 (e.g., human TGF-β3). Assays known to one of skill in the art or described herein (e.g., X-ray crystallography, ELISA assays, etc.) can be used to determine if two antibodies bind to the same epitope. Biacore assays can be used to assess and determine competitive binding and also epitope binding. Biacore can be utilized to determine the extent to which different antibodies interact with a single antigen or epitope, to assess protein protein or antibody-protein interactions, and to determine binding affinity.

TGF-β3 plays an important role in controlling the immune system and is a tumor promoter and a tumor suppressor. Studies of TGF-β3 in cancer provide a rational for blocking TGF-β3 signaling in human cancers for therapeutic effect. Overexpression of TGF-β ligands have been reported in most cancers, including in tumors resistant to conventional chemotherapy, and high levels of these in tumor tissues and/or serum are associated with early metastatic recurrences and/or poor patient outcome (Teicher, B. A. et al (1997) In Vivo 11:463-472; Wojtowicz-Praga, S. (2003) Invest New Drugs 21:21-32; Ito, N., et al. (1995) Cancer Lett 89:45-48; Shariat, S. F., et al (2001) Cancer 92:2985-2992; Shariat, S. F., et al (2001) J Clin Oncol 19:2856-2864; Tsushima, H., et al (2001) Clin Cancer Res 7:1258-1262; Rich, J. N. (2003) Front Biosci 8:e245e260). Animal studies with pan-TGF-β antibody have shown inhibition of tumor recurrence or metastasis in fibrosarcoma, colon cancer, and breast cancer (Terabe M et al (2003) J Exp Med 198:1741-1752; Nam J-S et al (2008) Cancer Res 68(10):3835-3843), and reduced radiation-induced acceleration of metastatic breast cancer (Biswas S et al (2007) 117:1305-1313). Evidence to date strongly supports that blocking TGFβ can enhance antigen uptake, presentation, and activation of antitumor immune response mediated by therapeutic vaccines. Indeed, recent studies have demonstrated that blockade of TGF-β, using mouse TGF-β generic antibody 1D11 (which recognizes TGF-β1, TGF-β2 and TGF-β3), synergistically enhances tumor vaccines in animal models via CD8+ T cells (Terabe M et al (2009) Clin Cancer Res 15:6560-6569; Takaku S et al (2010) Int J Cancer 126(7):1666). Radiation therapy has the potential to convert the irradiated tumor into an in situ vaccine (Formanti S C et al (2012) Int J Radiat Oncol Biol Phys 84:870-880). In recent studies, nonspecific TGF-β neutralizing antibody (1D11) administered during radiation therapy increased the ability of the therapy to induce T-cell responses to endogenous tumor antigens in preclinical models of metastatic breast cancer (Vanpoille-Box C et al (2015) Cancer Res 75(11):2232-2242). Additional blockade of PD-1 enhanced the effectiveness of radiation therapy with TGF-β antibody.

TGF-β antibodies have been generated and a particular example denoted 1D11, and its humanized counterpart GC1008, have been evaluated in animal models and early human clinical trials and are provided and disclosed in patent applications including in WO2007076391, WO2005097832, WO2006086469 and U.S. Pat. No. 5,571, 714. Antibody 1D11 and its humanized counterpart, however, are generic TGF-beta antibodies, recognizing all TGF-β forms including TGF-β1, TGF-β2 and TGF-β3.

Antibody 1D11 and its humanized counterpart do not, therefore, provide specific and directed modulation of TGF-β3.

Monocolonal antibodies derived by hybridoma technique from another species than human, such as mouse, can be humanized, which means that a non-human antibody is genetically engineered to be more human in order to avoid HAMA when infused into humans. Methods for humanization of antibodies are well known within the art, among the more common methods are complementarity-determining region (CDR) grafting and veneering (also known as resurfacing). These methods have been extensively described in the literature and in patents, see e.g.; King "Applications and Engineering of Monoclonal Antibodies" Taylor & Francis, 1998; U.S. Pat. Nos. 5,225,539; 5,530,101; 5,585,089, 5,859,205 and 6,797,492, each incorporated herein by reference. Another common method is the veneering (v) technology (Daugherty et al. (1991). Nucleic Acids Res. 19(9), 2471-6; U.S. Pat. No. 6,797,492; Padlan, E. A. (1991) Mol. Immunol. 28(4-5), 489-98; European Patent No. 519596). Where a replacement of the surface-exposed residues in the framework regions, which differ from those usually found in human antibodies, is performed in order to minimize the immunogenicity of an antibody's variable domains, while preserving ligand-binding properties.

Antibodies including fragments thereof may possess certain diagnostic applications and may for example, be utilized for the purpose of detecting and/or measuring conditions such as cancer, precancerous lesions, conditions related to or resulting from hyperproliferative cell growth or the like.

The radiolabelled specific binding members, particularly antibodies and fragments thereof, are useful in in vitro diagnostics techniques and in in vivo radioimaging techniques and in radioimmunotherapy. In the instance of in vivo imaging, the specific binding members of the present invention may be conjugated to an imaging agent rather than a radioisotope(s), including but not limited to a magnetic resonance image enhancing agent, wherein for instance an antibody molecule is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanium, holmium and ferbium. In a further aspect of the invention, radiolabelled specific binding members, particularly antibodies and fragments thereof, particularly radioimmunoconjugates, are useful in radioimmunotherapy, particularly as radiolabelled antibodies for cancer therapy. In a still further aspect, the radiolabelled specific binding members, particularly antibodies and fragments thereof, are useful in radioimmuno-guided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

Radioimmunotherapy (RAIT) has entered the clinic and demonstrated efficacy using various antibody immunoconjugates. $^{131}$I labeled humanized anti-carcinoembryonic antigen (anti-CEA) antibody hMN-14 has been evaluated in colorectal cancer (Behr T M et al (2002) Cancer 94(4Suppl): 1373-81) and the same antibody with $^{90}$Y label has been assessed in medullary thyroid carcinoma (Stein R et al (2002) Cancer 94(1):51-61). Radioimmunotherapy using monoclonal antibodies has also been assessed and reported for non-Hodgkin's lymphoma and pancreatic cancer (Goldenberg D M (2001) Crit Rev Oncol Hematol 39(1-2):195-201; Gold D V et al (2001) Crit Rev Oncol Hematol 39 (1-2) 147-54). Radioimmunotherapy methods with particular antibodies are also described in U.S. Pat. Nos. 6,306,393 and 6,331,175. Radioimmunoguided surgery (RIGS) has also entered the clinic and demonstrated efficacy and usefulness, including using anti-CEA antibodies and antibodies directed against tumor-associated antigens (Kim J C et al (2002) Int J Cancer 97(4):542-7; Schneebaum S et al (2001) World J Surg 25(12):1495-8; Avital S et al (2000) Cancer 89(8): 1692-8; McIntosh D G et al (1997) Cancer Biother Radiopharm 12 (4):287-94).

In vivo animal models of cancer or animal xenograft studies may be utilized by the skilled artisan to further or additionally screen, assess, and/or verify the specific binding members and antibodies or fragments thereof of the present invention, including further assessing TGF-β3 modulation and inhibition in vivo and inhibiting tumor progression, recurrence, metastasis, or immune response against tumor cells or response to antigens or vaccines, including tumor or cancer antigens or vaccines. Such animal models include, but are not limited to models of immune response, immune modulation, vaccination, cancer, cancer metastasis. Models of cancers whose recurrence or metastasis are associated with elevated levels of TGF-β3 are particularly susceptible to and targeted by the antibodies of the present invention. Such cancers include melanomas, breast, lung and prostate cancer. Exemplary and suitable models are known and readily available to the skilled artisan and include those referenced and/or described herein and known in the art. For example, antibodies or active fragments thereof of the invention may be evaluated in breast cancer models, including tumorigenicity of human breast cancer cells in athymic mice (Arteaga C L et al (1993) Cell Growth Diff 4:193-201) or in Neu-induced mammary tumors (Muraoka-Cok R S et al (2004) Cancer Res 64:2002-2011), or in evaluating metastases of transgenic mammary tumors (Siegel P M et al (2003) Proc Natl Acad Sci USA 100:8430-8435). Also, as an example the anti-tumor effect of TGF-β3 antibody can be examined on a whole cell vaccine in prophylaxis against injected CT26 colon carcinoma tumors in syngeneic mice using a method similar to that reported by Takaku et al (Takaku S et al (2010) Int J Cancer 126(7):1666).

Antibodies of the present invention may be administered to a patient in need of treatment via any suitable route, including by injection, including intreperitoneally, intramuscularly, subcutaneous, intravenous, into the bloodstream or CSF, or directly into the site of the tumor or by intratumoral administration or intratumoral injection. The precise dose will depend upon a number of factors, including whether the antibody is for diagnosis or for treatment, the size and location of the tumor, the precise nature of the antibody (whether whole antibody, fragment, diabody, etc), and the nature of the detectable or functional label attached to the antibody. Where a radionuclide is used for therapy, a suitable single dose may be about 45 mCi/m$^2$, to a maximum of about 250 mCi/m$^2$. Preferable dosage is in the range of 15 to 40 mCi, with a further preferred dosage range of 20 to 30 mCi, or 10 to 30 mCi. Such therapy may require bone marrow or stem cell replacement. A typical antibody dose for either tumor imaging or tumor treatment will be in the range of from 0.5 to 40 mg, preferably from 1 to 4 mg of antibody in F(ab')2 form. Naked antibodies are preferably administered in doses of 20 to 1000 mg protein per dose, or 20 to 500 mg protein per dose, or 20 to 100 mg protein per dose. This is a dose for a single treatment of an adult patient, which may be proportionally adjusted for children and infants, and also adjusted for other antibody formats, in proportion for example to molecular weight. Treatments may be repeated at daily, twice-weekly, weekly or monthly intervals, at the discretion of the physician.

Pharmaceutical and Therapeutic Compositions

Antibodies and fragments of the present invention will usually be administered in the form of a pharmaceutical composition, which may comprise at least one component in addition to the specific binding member. Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous, or by deposition at a tumor site.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, therapeutics or agents, either simultaneously or sequentially dependent upon the condition to be treated. In addition, the present invention contemplates and includes compositions comprising the binding member, particularly antibody or fragment thereof, herein described and other agents or therapeutics such as anti-cancer agents or therapeutics, hormones, anti-mitotic agents, anti-apoptotic agents, antibodies, or immune modulators. More generally these anti-cancer agents may be but are not limited to tyrosine kinase inhibitors or phosphorylation cascade inhibitors, post-translational modulators, cell growth or division inhibitors (e.g. anti-mitotics), or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. The composition can be administered in combination (either sequentially i.e. before or after) or simultaneously) with tyrosine kinase inhibitors (including, but not limited to AG1478 and ZD1839, STI571, OSI-774, SU-6668), doxorubicin, temozolomide, cisplatin, carboplatin, nitrosoureas, procarbazine, vincristine, hydroxyurea, 5-fluoruracil, cytosine arabinoside, cyclophosphamide, epipodophyllotoxin, carmustine, lomustine, and/or other chemotherapeutic agents. Thus, these agents may be specific anti-cancer agents, or immune cell response modulators or may be more general anti-cancer and anti-neoplastic agents such as doxorubicin, cisplatin, temozolomide, nitrosoureas, procarbazine, vincristine, hydroxyurea, 5-fluoruracil, cytosine arabinoside, cyclophosphamide, epipodophyllotoxin, carmustine, or lomustine. In addition, the composition may be administered with hormones such as dexamethasone, immune modulators, such as interleukins, tumor necrosis factor (TNF) or other growth factors, colony stimulating factors, cytokines, agonist or antagonist antibodies to regulators of immune response which stimulate, enhance, or derepress the immune response and reduction or elimination of cancer cells or tumors. The composition may also be administered with, or may include combinations along with other anti-tumor antigen antibodies.

In addition, the present invention contemplates and includes therapeutic compositions for the use of the antibody(ies) or fragments in combination with conventional radiotherapy.

The present invention further contemplates therapeutic compositions useful in practicing the therapeutic methods of this invention. A subject therapeutic composition includes, in admixture, a pharmaceutically acceptable excipient (carrier) and one or more of a specific binding member or antibody, polypeptide analog thereof or fragment thereof, as described herein as an active ingredient. In an embodiment, the composition comprises an antigen capable of modulating the specific binding of the present binding member/antibody with a target cell. In an embodiment the composition comprises an antigen or vaccine formulation, particularly a tumor antigen or cancer vaccine.

The preparation of therapeutic compositions which contain polypeptides, analogs or active fragments as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

An alternative paradigm for cancer therapy utilizing intratumoral immunomodulation and intratumoral immunization has been described and reviewed (Marabelle A et al (2014) Clin Cancer Res 20(7):1747-1756). This paradigm may be particularly effective for drug therapies designed to interact with molecules playing a role in the activation of immune cells to reverse cancer-induced immunotolerance and facilitate antitumor immune response, including immunostimulator monoclonal antibodies (Marabelle A et al (2014) Clin Cancer Res 20(7):1747-1756; Mellman I et al (2011) Nature 480:480-489). Application of this paradigm to the antibodies and active fragments of the present invention is an aspect of this invention. Delivery of immunostimulatory monoclonal antibodies directly into the tumor to generate or facilitate a systemic antitumor immune response, including a more potent antitumor response causing less autoimmune toxicity or other side effects and the need for less drug than systemically administered drugs or antibodies, Antibody delivery in adjuvant around established tumor (anti-CTLA-4 Ab delivered in water-in-oil emulsion adjuvant (Montadine ISA51) around colon carcinoma tumor) eradicated the local tumor and prevented distinct tumor development (Fransen M F et al (2013) Cancer Res 19:5381-5389).

The compositions are administered in a manner compatible with the dosage formulation, and in a therapeutically effective amount. The quantity to be administered depends on the subject to be treated, capacity of the subject's immune system to utilize the active ingredient, and degree of peptide/MHC or tumor antigen binding capacity desired. Precise amounts of active ingredient required to be administered depend on the judgment of the practitioner and are peculiar to each individual. Suitable regimes for initial administration and follow on administration are also variable, and may include an initial administration followed by repeated doses at one or more hour intervals by a subsequent injection or other administration. Alternatively, continuous intravenous infusion sufficient to maintain appropriate and sufficient concentrations in the blood or at the site of desired therapy is contemplated.

Diagnostic Assays

The present invention also relates to a variety of diagnostic applications, including methods for detecting the expression of or elevated presence of TGF-β3, TGF-β3-mediated cancer, or cancer more generally, evaluating the presence or amount of TGF-β3-responsive cells, by reference to their ability to be recognized by the present specific binding member(s). Peptide complexes can be identified, targeted, labeled, and/or quantitated on cells, including immune cells and/or tumor cells.

Diagnostic applications of the specific binding members of the present invention, particularly antibodies and fragments thereof, include in vitro and in vivo applications well known and standard to the skilled artisan and based on the present description. Diagnostic assays and kits for in vitro assessment and evaluation of tumor and cancer status, and tumor response or immune response, may be utilized to diagnose, evaluate and monitor patient samples including those known to have or suspected of having cancer, a precancerous condition, a condition related to hyperproliferative cell growth or from a tumor sample. The assessment and evaluation of cancer, tumor and metastatic disease status is also useful in determining the suitability of a patient for a clinical trial of a drug or for the administration of a particular chemotherapeutic agent or specific binding member, particularly an antibody, of the present invention, including combinations thereof, versus a different agent or binding member. This type of diagnostic monitoring and assessment is already in practice utilizing antibodies against the HER2 protein in breast cancer (HERCEPTEST, Dako Corporation), where the assay is also used to evaluate patients for antibody therapy using Herceptin. In vivo applications include imaging of tumors or assessing cancer status of individuals, including radioimaging.

Preferably, the antibody used in the diagnostic methods of this invention is mouse, human, humanized or recombinant antibody. Preferably, the antibody is a single chain antibody or domain antibody. In addition, the antibody molecules used herein can be in the form of Fab, Fab', F(ab')2 or F(v) portions of whole antibody molecules, particularly Fab.

The presence of TGF-β3 in cells or TGF-β3 responsive cells or TGF-β3 responsive genes or proteins can be ascertained by the usual in vitro or in vivo immunological procedures applicable to such determinations. A number of useful procedures are known. The procedures and their application are all familiar to those skilled in the art and accordingly may be utilized within the scope of the present invention.

In a further embodiment of this invention, commercial test kits suitable for use by a medical specialist may be prepared to determine the presence or absence of aberrant expression of including but not limited to amplified TGF-β3, in suspected target cells. In accordance with the testing techniques discussed above, one class of such kits will contain at least the labeled or its binding partner, for instance an antibody specific thereto, and directions, of course, depending upon the method selected. The kits may also contain peripheral reagents such as buffers, stabilizers, etc.

Accordingly, a test kit may be prepared for the demonstration of the presence of or elevated levels of TGF-β3 or a TGF-β3-responsive element or protein, comprising:

(a) a predetermined amount of at least one labeled immunochemically reactive component obtained by the direct or indirect attachment of the present specific binding member or a specific binding partner thereto, to a detectable label;

(b) other reagents; and (c) directions for use of said kit.

A test kit may be prepared for the demonstration of the presence of TGF-β3-mediated cancer, particularly selected from breast, lung, liver, prostate, bladder cancer comprising:

(a) a predetermined amount of at least one labeled immunochemically reactive component obtained by the direct or indirect attachment of the present specific binding member or a specific binding partner thereto, to a detectable label;

(b) other reagents; and (c) directions for use of said kit.

In accordance with the above, an assay system for screening potential drugs effective to modulate the presence or activity of TGF-β3 and/or the activity or binding of the antibody of the present invention may be prepared. The antigen peptide or the binding member or antibody may be introduced into a test system, and the prospective drug may also be introduced into the resulting cell culture, and the culture thereafter examined to observe any changes in the activity of the cells, binding of the antibody, or amount and extent of TGF-β3 due either to the addition of the prospective drug alone, or due to the effect of added quantities of the known agent(s).

Nucleic Acids

The present invention further provides an isolated nucleic acid encoding a specific binding member of the present invention. Nucleic acid includes DNA and RNA. In a preferred aspect, the present invention provides a nucleic acid which codes for a polypeptide of the invention as defined above, including a polypeptide as set out in FIGS. 4C, 15, 16, 17, 18 and/or 19, or capable of encoding the CDR regions thereof.

The present invention also provides constructs in the form of plasmids, vectors, transcription or expression cassettes which comprise at least one polynucleotide as above. The present invention also provides a recombinant host cell which comprises one or more constructs as above. A nucleic acid encoding any specific binding member as provided itself forms an aspect of the present invention, as does a method of production of the specific binding member which method comprises expression from encoding nucleic acid therefor. Expression may conveniently be achieved by culturing under appropriate conditions recombinant host cells containing the nucleic acid. Following production by expression a specific binding member may be isolated and/or purified using any suitable technique, then used as appropriate.

Specific binding members and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic.

Systems for cloning and expression of a polypeptide in a variety of different host cells are well known. Suitable host cells include bacteria, mammalian cells, yeast and baculovirus systems. Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate.

Thus, a further aspect of the present invention provides a host cell containing nucleic acid as disclosed herein. A still further aspect provides a method comprising introducing such nucleic acid into a host cell. The introduction may employ any available technique. The introduction may be followed by causing or allowing expression from the nucleic acid, e.g. by culturing host cells under conditions for expression of the gene. The present invention also provides a method which comprises using a construct as stated above in an expression system in order to express a specific binding member or polypeptide as above.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host. A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col El, pCR1, pBR322, pMB9 and their derivatives, plasmids such as RP4; phage DNAs, e.g., the numerous derivatives of phage k, e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention.

As mentioned above, a DNA sequence encoding a specific binding member can be prepared synthetically rather than cloned. The DNA sequence can be designed with the appropriate codons for the specific binding member amino acid sequence. In general, one will select preferred codons for the intended host if the sequence will be used for expression. The complete sequence is assembled from overlapping oligonucleotides prepared by standard methods and assembled into a complete coding sequence. Synthetic DNA sequences allow convenient construction of genes which will express specific binding member analogs or "muteins". Alternatively, DNA encoding muteins can be made by site-directed mutagenesis of native specific binding member genes or cDNAs, and muteins can be made directly using conventional polypeptide synthesis.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Production of TGFbeta-3 Antibodies

Mature mouse and human TGF-β3 share 100% homology at the protein level which makes it extremely difficult to generate mouse antibodies against both the human and the mouse protein due to immune tolerance. The mouse and human TGF-β3 amino acid sequences are as follows:

```
Mouse
NCBI Reference Sequence: NT_033394.2
                                     (SEQ ID NO: 45)
aldtnycfrn leenccvrpl yidfrqdlgw kwvhepkgyy anfcsgpcpy lrsadtthst vlglyntlnp easaspccvp qdlepltily yvgrtpkveq lsnmvvksck cs Human
UniProtKB/Swiss-Prot: P10600.1
                                     (SEQ ID NO: 46)
aldtnycfrn leenccvrpl yidfrqdlgw kwvhepkgyy anfcsgpcpy lrsadtthst vlglyntlnp easaspccvp qdlepltily yvgrtpkveq lsnmvvksck cs
```

TGF-β3 antibodies were successfully generated using a procedure in mice we have termed 'auto-vaccination' (FIG. 1). Auto-vaccination was successfully utilized to generate antibodies in mice against several proteins involved in the control of immune and inflammatory responses. In this procedure, large OVA multimers were made by treating ovalbumin (OVA) with glutaraldehyde and, after purifying the polymerized products by size exclusion chromatography, these OVAglu multimers are reacted with the target cytokine (in this instance TGF-β3) before saturating remaining glutaraldehyde sites with PADRE peptide (CKXVAAWTLKAAZ) (SEQ ID NO:47) (x=cycloexylamine, included to prevent proteolysis) (Alexander, J. et al (1994) Immunity 1:751-761) and Tetanus toxin peptide (Tt 947-967 CFNNFTVSFWLRVPKVSASHLE (SEQ ID NO:48)) to maximize immunogenicity. The efficacy of OVAglu in breaking tolerance against self-antigens was demonstrated by detection of specific antibodies to TGF-β3 by ELISA at serum dilutions of $10^4$-$10^6$.

Antibodies to TGF-β3 were prepared by subcutaneous vaccination of C57BL/6 mice in the footpads with 2-5 ug of TGF-β3-OVA-PADRE-Tetanus toxin peptide complexes along with GERBU100 adjuvant (GERBU Biochemicals, Gaiberg, Germany) 5 times at 2 week intervals. Mice were bled two weeks after the last boost and sera found positive for anti-TGF-β3 antibodies by ELISA (not shown). After a 2 to 6 week rest, a combined intravenous and intraperitoneal booster with 2-5 μg complexes was given for mAb production.

Reagents and Mice

All vaccinations were performed in C57BL/6 mice maintained under specific pathogen-free conditions at The Ludwig Institute for Cancer Research, Brussels Branch, Brussels, Belgium. Mouse TGF-β3 was from Shenandoah Biotechnology Inc. (Catalog Number: 200-27 Accession Number: P04202).

Activated Carrier Production

OVA (Product A2512, Sigma-Aldrich, St. Louis, Mo., USA), at a concentration of 0.22 mM, was polymerized by overnight incubation with 20 mM glutaraldehyde in 50 mM potassium phosphate buffer, pH 6, at 4° C. After dialysis against the same buffer, the soluble product was fractionated on a SUPEROSE12 size exclusion chromatography column (GE Healthcare, Diegem, Belgium), equilibrated at pH 6 in 50 mM phosphate buffer. Large size products (>1000 kD), designated OVAglu, were collected and frozen at 80° C. in aliquots.

TGF-β3-OVA-PADRE-Tetanus toxin complexes were produced as follows: 128 μg HTGF-β3 in 950 μl acetic acid (50 mM) was mixed with 452 μg OVAglu J1307 (174 μl at 2.6 mg/ml) and 200 μl 1M carbonate buffer pH8.5. After 7 h incubation with gentle permanent mixing, the mixture was split in two equal parts. One was incubated with 58 μg (58 μl at 1 mg/ml) PADRE peptide CKXVAAWTLKAAZ (SEQ ID NO:47) (Alexander, J. et al 1994 Immunity 1:751-761) while the other was incubated with 130 μg Tetanus toxin peptide 947-967 (TT) CFNNFTVSFWLRVPKVSASHLE (SEQ ID NO:48)-(65 μl at 2 mg/ml). After 3 h, the same amount of peptides was added in reverse (TT to PADRE complexes and PADRE to TT complexes) and incubation was pursued overnight at 7° C. Complexes were dialyzed against 50 mM glycine buffer pH 4.5+Tween 20 (diluted $10^{-4}$). Both samples were concentrated by evaporation to a final volume of 500 μl. TT/PADRE (194 μg) and PADRE/TT (234 μg) conjugates were mixed and aliquots were frozen for immunization.

Immunizations

Immunizations were performed by four to five biweekly s.c. injections into the footpads of 2 μg complexes emulsified in GERBU100 adjuvant, according to the instructions of the supplier (GERBU Biochemicals, Gaiberg, Germany). Mice were bled 2 weeks after the last boost. After a 2-6 week rest, a combined i.v. and i.p. booster with 2 μg complexes was given for mAb production.

Antibody Isolation and Selection

A group of mouse anti-TGF-β3 antibodies were isolated: MTGF-β3-9/8 (also denoted as MTGF-β3-9), MTGF-β3-1203/11 (also denoted as MTGF-β3-12), MTGF-β3-1679/2 (also denoted as MTGF-β3-16), MTGF-β3-1719/13 (also denoted as MTGF-β3-17), MTGF-β3-1901/16 (also denoted as MTGF-β3-19).

The antibodies are all IgG class antibodies, and differ in subclass. MTGF-β3-19 antibody is an IgG1. Antibodies MTGF-β3-9, MTGF-β3-16 and MTGF-β3-17 are IgG2a. Antibody MTGF-β3-12 is an IgG2b. The antibodies were subsequently evaluated for TGF-β3 binding and TGF-β3 neutralization as described in the next Examples.

Example 2

Binding of Isolated TGF-β3 Antibody Clones to Recombinant TGF-β3

Figure 2:
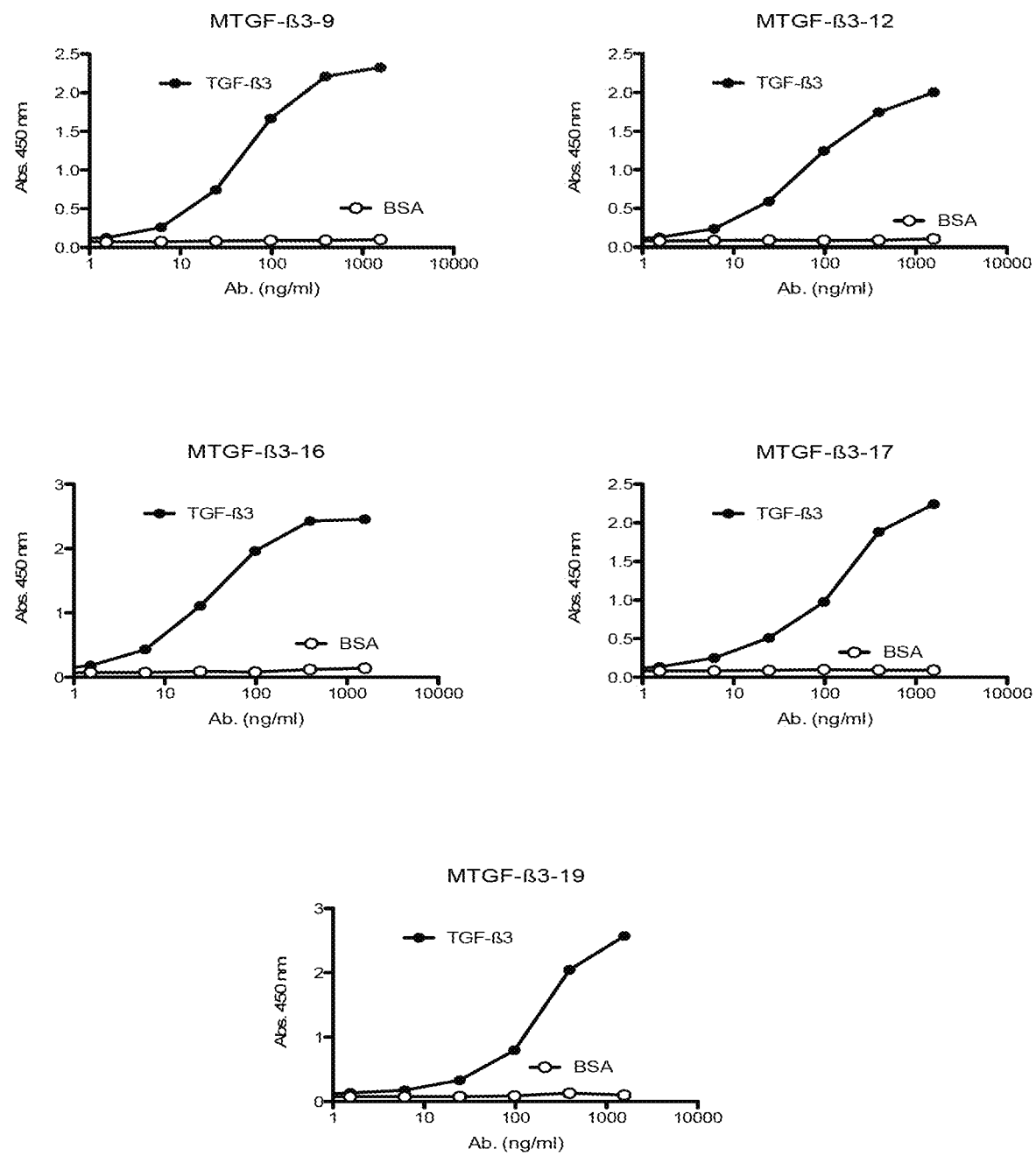
FIG. 2 depicts binding of the TGF-Beta3 antibodies to recombinant TGF-β3. BSA binding was also evaluated as a control and is shown. Binding of each of antibodies MTGF-β3-9, MTGF-β3-12, MTGF-β3-16, MTGF-β3-17 and MTGF-β3-19 is shown as indicated.
Figure 3:
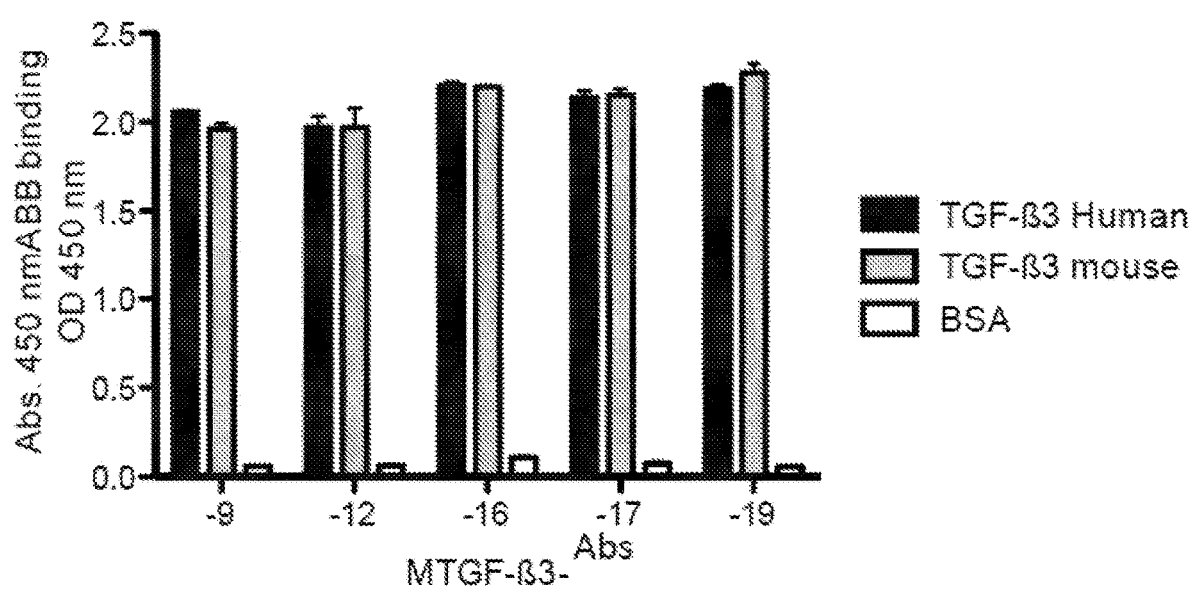
FIG. 3 depicts binding of the MTGF-β3 antibodies to human and mouse recombinant TGF-β3, with BSA binding as a control. Binding of each of antibodies MTGF-β3-9 (denoted—9), MTGF-β3-12 (denoted—12), MTGF-β3-16 (denoted—16), MTGF-β3-17 (denoted—17) and MTGF-β3-19 (denoted—19) is shown as indicated.
Figure 4A:
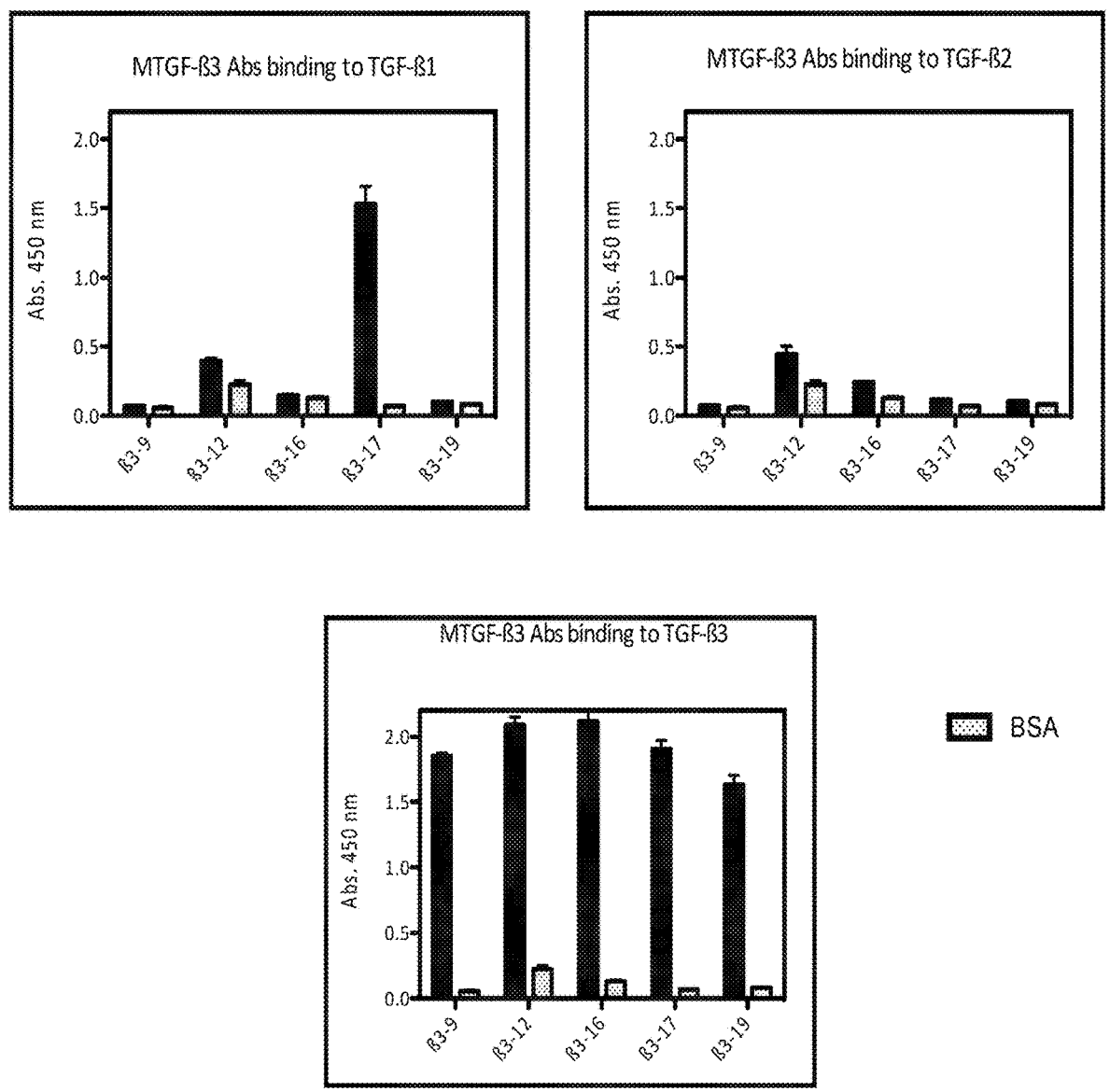
FIG. 4A depicts reactivity of the TGF-β3 antibodies with human TGF-β1, TGF-β2 and TGF-β3 isoforms. Binding was evaluated of antibodies at 3 µg/ml.
Figure 4B:
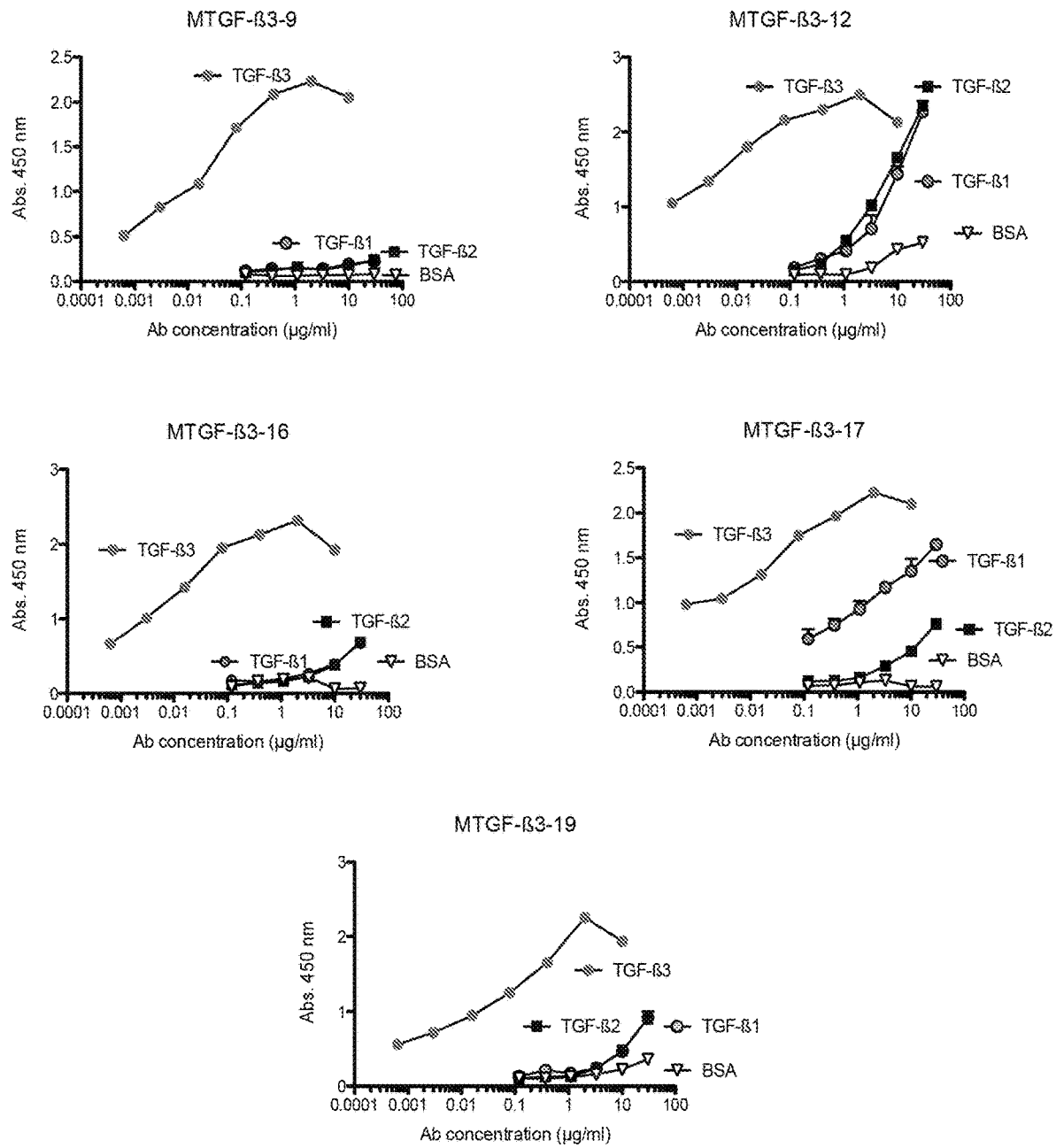
FIG. 4B depicts dose response reactivity of the TGF-β3 antibodies with human TGF-β1, TGF-β2 and TGF-β3 isoforms versus BSA control. Each antibody MTGF-β3-9, MTGF-β3-12, MTGF-β3-16, MTGF-β3-17 and MTGF-β3-19 reactivity is depicted separately as indicated.

Isolated anti-TGF-β3 clones generated by the protocol above were screened for binding ability to recombinant TGF-β3 (FIG. 2). All five mouse TGF-β3 clones bind to both human and mouse TGF-β3 recombinant protein (FIG. 3). MAXISORB immunoplates were coated overnight in 50 mM glycine buffer, pH 9 at 4° C. with 500 ng/ml human TGF-β1, TGF-β2 or TGF-β3 (Prospec-Tany Technogene Ltd, Israel). Contrary to 1D11 mouse monoclonal anti-TGF-β antibody, an established reference anti-TGF-β antibody which recognizes TGF-β1, TGF-β2 and TGF-β3 (Dasch J R et al (1989) J Immunol 142:1536-1541), monoclonal antibodies MTGF-β3-9 (IgG2a), MTGF-β3-12 (IgG2b), MTGF-β3-16 (IgG2a), and MTGF-β3-19 (IgG1) tested at 3 μg/ml bind only to TGF-β-3 while MTGF-β3-17 binds TGF-β1 and TGF-β3 (FIG. 4A). At higher concentrations MTGF-β3-12 also bound to TGF-β1 and TGF-β2 (FIG. 4B) suggesting that the five antibodies could be grouped in 3 categories, MTGF-β3-9, -16 and 19 very specific for TGF-l33, MTGF-β3-17 reacting with TGF-β1 and TGF-β3, and MTGF-β3-12 strongly reactive with TGF-β3 but also showing low affinity binding to TGF-β1 and TGF-β2. VL and VH sequence analysis revealed 3 subgroups of antibodies based on their sequence homology confirming the existence of these 3 distinct phenotypes defined by their antigenic specificity (FIG. 4C).

Figure 5:
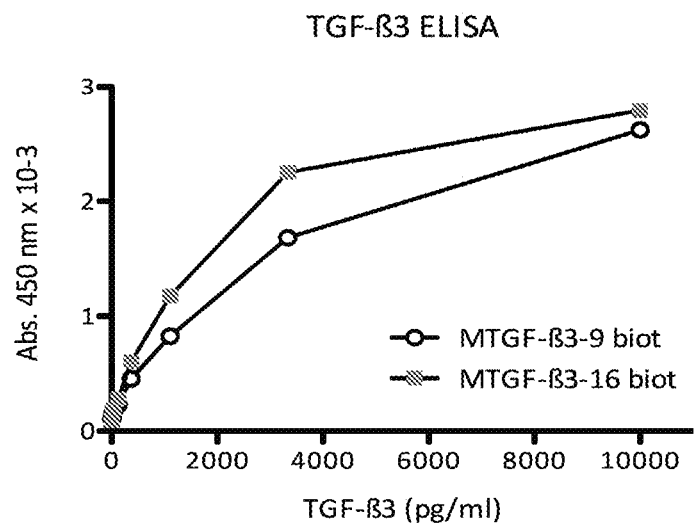
FIG. 5 provides sandwich antibody for detection of human TGF-β3. ELISA plates are coated with MTGF-β3-17 antibody at 4 µg/ml overnight saturated with 10% FCS. Human TGF-β3 samples are incubated for 2 hrs at 37° C. Biotinylated MTGF-β3-9 or MTGF-β3-16 are added, Avidin HRP is added for 1 hour, and detection is evaluated using TMB. Absorbance at 450 nm is graphed versus TGF-β3 concentration in pg/ml. The quantitative results are also tabulated.

These results indicated that MTGF-β3-17 differs in specificity with the other antibodies which suggested that they could form an analytical pair in sandwich ELISAs. Detection of human TGF-β3 by sandwich ELISA is achieved by using MTGF-β3-17 coated on an immunoabsorbent plate to capture TGF-β3. TGF-β3 detection antibody can be selected from any of the following anti-TGF-β3 specific antibodies: MTGF-β3-9 (IgG2a), MTGF-β3-12 (IgG2b), MTGF-β3-16 (IgG2a), and MTGF-β3-19 (IgG1) (FIG. 5) illustrates sandwich ELISA using MTGF-β3-17 to capture TGF-β3 and biotinylated MTGF-β3-9 or MTGF-β3-16 for detection. Detection of human TGF-β3 by sandwich ELISA can also be achieved by using MTGF-β3-12 coated on an immunoabsorbent plate to capture TGF-β3 and by using MTGF-β3-17 antibody for detection.

Example 3

Binding Characteristics of TGF-β3 Antibodies in Competition Assays

Figure 6:
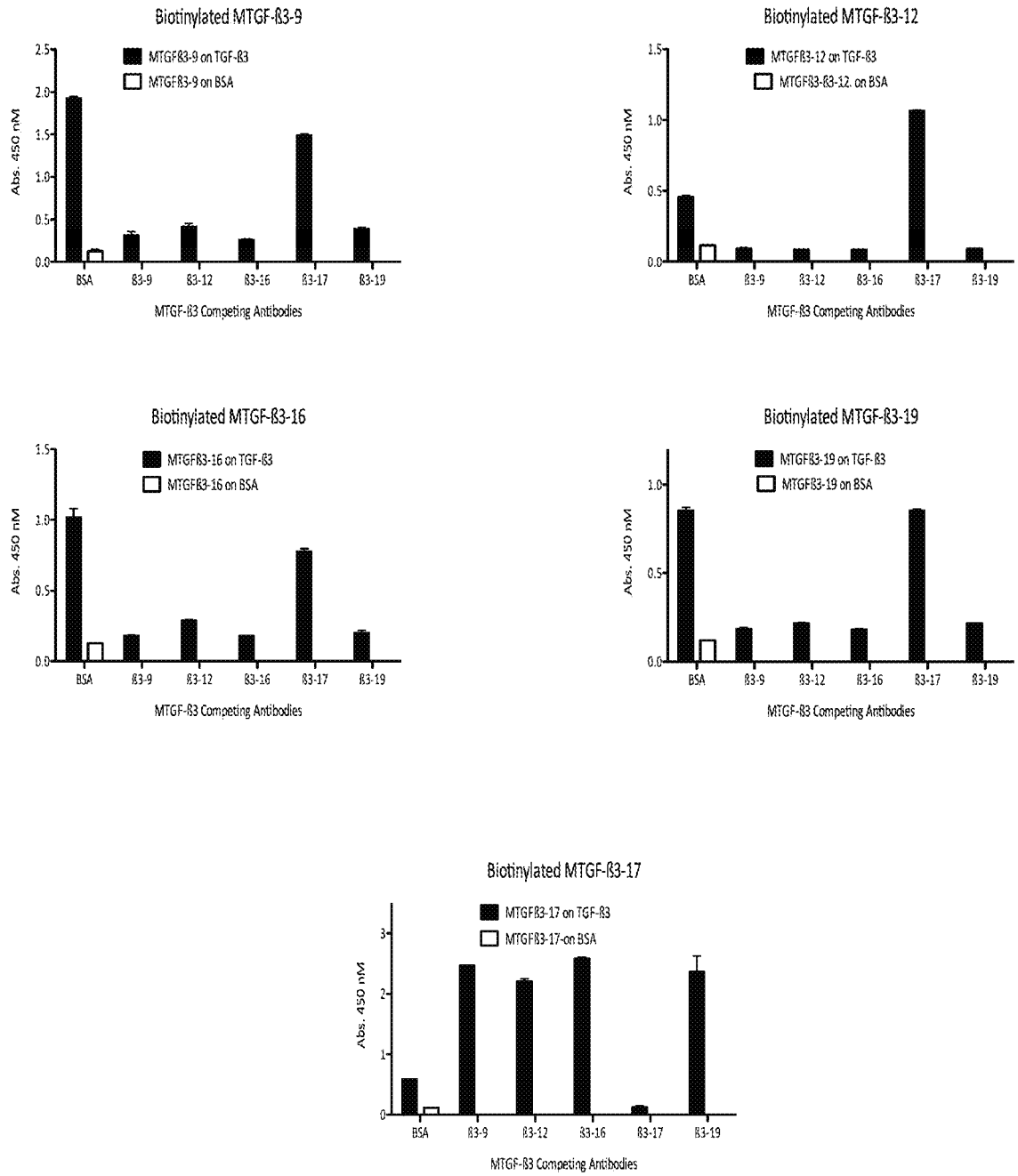
FIG. 6 shows competition of the different MTGF-β3 antibodies, MTGF-β3-9, MTGF-β3-12, MTGF-β3-16, MTGF-β3-19 and MTGF-β3-17, with one another. Maxisorb ELISA plates were coated with TGF-β3 (500 ng/ml in 40 mM glycine pH9) overnight. After 1 hour saturation with 10% FCS, the plates were incubated with each the different unlabeled antibodies as indicated at 10 μg/ml in PBS with 1% BSA for 1 hour. The biotinylated test antibody were then added at 100 ng/ml (25 ng/ml for MTGF-β3-16) without washing (the unlabeled antibodies remaining in the plate to ensure optimal competition). After a 2 hour incubation at 37° C. and washing, Avidine-HRP was added for 1 hour. Bound HRP was detected with a TMB substrate.

The relative binding characteristics of each isolated anti-TGF-β3 antibody, MTGF-β3-9 (IgG2a), MTGF-β3-12 (IgG2b), MTGF-β3-16 (IgG2a), MTGF-β3-17 (IgG2a) and MTGF-β3-19 (IgG1), were compared in competition binding experiments with each other: In each instance, MAX-ISORB ELISA plates were coated with 500 ng/ml TGF-β3 in 40 mM glycine pH9 overnight. 10% of fetal calf serum (FCS) in PBS was added for 1 hour to saturate the plate. After such period of incubation, unlabeled antibodies at 10 ug/ml in PBS with 1% BSA were added to the plate for 1 hour. After incubation period with unlabeled antibodies, biotin labeled antibodies (100 ng/ml) unless noted otherwise were added to the unlabelled antibodies. After 2 h incubation at 37° and followed by washing, streptavidin-HRP was added for 1 h. If non-biotinylated antibodies bind to TGF-β3 coated on the plate at epitopes similar to the ones recognized by the biotinylated antibody they will inhibit binding of the biotinylated Abs. The results are provided in (FIG. 6). TGF-β3 specific antibodies MTGF-β3-9 (IgG2a), MTGF-β3-12 (IgG2b), MTGF-β3-16 (IgG2a) and MTGF-β3-19 (IgG1) individually compete with the other for binding to TGF-β3. This data illustrates that binding of TGF-β3 by each of these TGF-β3 specific antibodies interferes with each other's binding to TGF-β3. The data provided in FIG. 6 demonstrate that MTGF-β3-9 (IgG2a), MTGF-β3-12 (IgG2b), MTGF-β3-16 (IgG2a) and MTGF-β3-19 (IgG1) bind to same site on TGF-β3.

Figure 7:
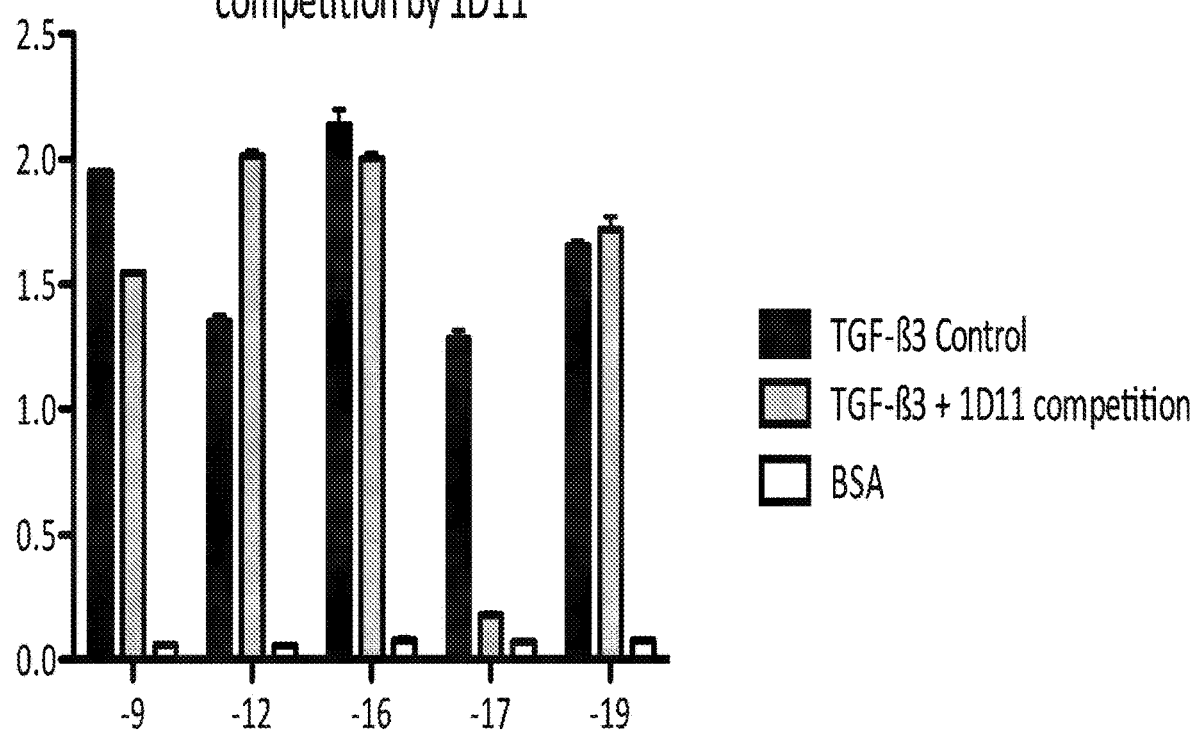
FIG. 7 shows competition by antibody 1D11 against the different MTGF-β3 antibodies for binding to TGF-β3. Binding of biotinylated MTGF-β3 antibodies was evaluated for competition by 1D11, which recognizes all of TGF-β1, TGF-β2 and TGF-β3 isoforms. ELISA plates were coated with human TGF-β3 (500 ng/ml) overnight. After 1 hour saturation with 10% FCS at 37° C., the plates were incubated or not with 50 μl 1D11.16 at 20 μg/ml in 1% BSA for 2 hours. Then, 5 μl of the biotinylated test MTGF-β3 antibody was added at 5 μg/ml. After a 2 hour incubation at 37° C. and washing, Avidine-HRP was added for 1 hour. Bound HRP was detected with a TMB substrate. Only antibody MTGF-β3-17 is inhibited by 1D11.
Figure 8:
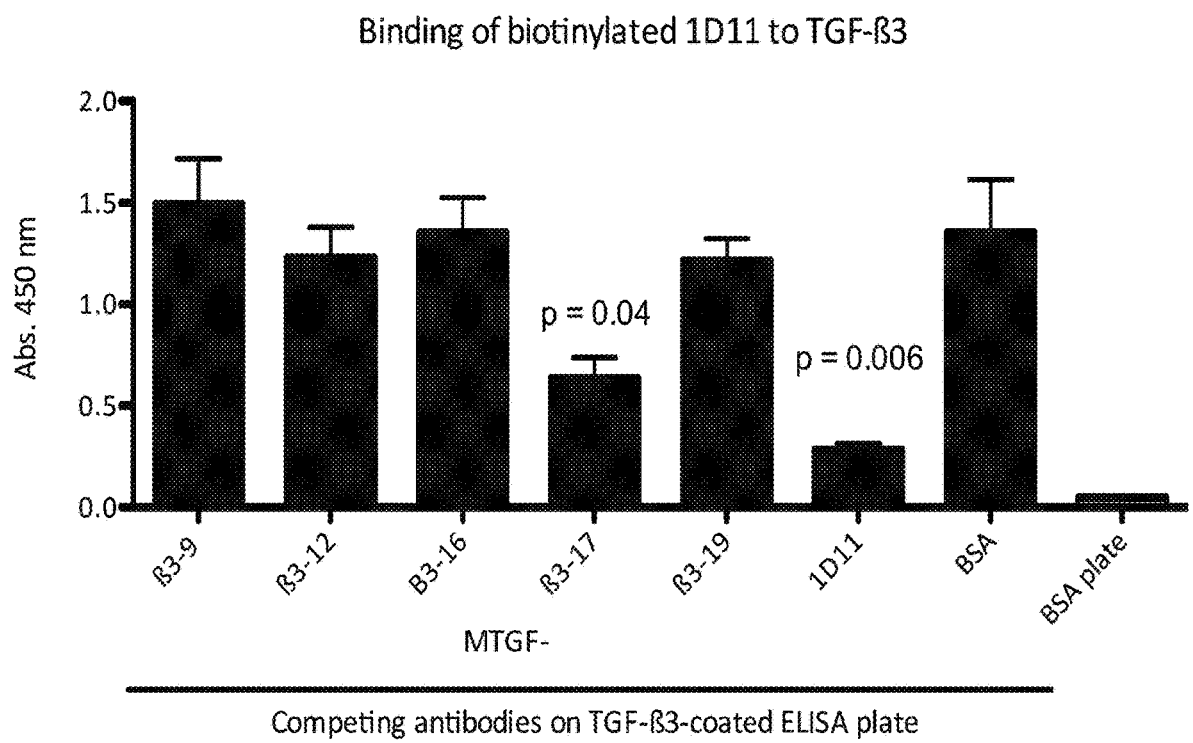
FIG. 8 shows competition by the different MTGF-β3 antibodies against antibody 1D11. Binding of antibody 1D11 on TGF-β3-coated ELISA plates was evaluated after incubation with unlabelled MTGF-β3 antibodies MTGF-β3-9 (denoted β3-9), MTGF-β3-12 (denoted β3-12), MTGF-β3-16 (denoted β3-16), MTGF-β3-17 (denoted β3-17), MTGF-β3-19 (denoted β3-19). Unlabelled 1D11 and BSA were used as controls. Maxisorb plates were coated with TGF-β3 or BSA overnight. After 1 hour saturation with 10% FCS, the plates were incubated for 1 hour with 50 μl of unlabelled antibodies (20 μg/ml). Then, 5 μl of biotinylated 1D11 antibody (4.7 μg/ml) final 0.43 μg/ml was added and incubated for 2 hours. The plates were washed and bound 1D11 was detected with Avidine-HRP for 1 hour. Bound HRP was detected with a DTT substrate. The Mean±SEM is graphed, N=4 in each instance. For P values, P versus BSA competition was calculated by unpaired T test (InStat). The results show that only antibody MTGF-β3-17 inhibits 1D11.

MTGF-β3-17 (IgG2a) antibody, which failed to inhibit binding of biotinylated MTGF-β3-9 (IgG2a), MTGF-β3-12 (IgG2b), MTGFβ3-16 (IgG2a) or MTGFβ3-19 (IgG1), to TGF-β3 was also not inhibited by the latter but inhibited itself (FIG. 6). This data illustrates TGF-β3-17 (IgG2a) binds to a different site on TGF-β3. We also compared the specificity of MTGF-β3 antibodies to that of 1D11 by competition assays using biotinylated MTGF-β3 antibodies and unlabelled 1D11 as competitor. As shown in FIG. 7, 1D11 inhibited MTGF-β3-17 but not the other MTGF-β3 antibodies. These results were confirmed in the opposite direction using biotinylated 1D11 (FIG. 8) and non-labeled MTGF-β3 antibodies as competitors. This indicates TGF-β3-17 and 1D11 bind to similar epitopes on TGF-β3, in agreement with the fact that, like 1D11, TGF-β3-17 also reacts with TGF-β1 and TGF-β2.

Example 4

Neutralizing Activity of TGF-β3 Antibodies In Vitro

The TGF-β3 antibodies were assayed for their neutralizing activity by evaluating TGF-β3 mediated induction of the downstream gene PAI-1 in a luciferase assay in cells. Neutralization of human TGF-β3 activity was demonstrated by evaluating loss of TGF-β-mediated induction of downstream genes using methods described by Abe M et al. (Anal Biochem 1994 Feb. 1; 216 (2):276-84). The expression of the PAI-1 gene was used to monitor TGF-β activity.

Mink lung epithelial cell line (TMLECs) were stably transfected with a truncated PAI-1 promoter fused to the firefly luciferase reporter gene. 500 pg/ml human TGF-β3 was incubated with serial dilutions of isolated TGF-β3 antibody for 4 h at 37° C. before transfer to an equal volume of culture medium (DMEM+10% FCS) where 50,000 TMLEC cells had been seeded 1-4 h earlier. After a further 24 h incubation, luciferase activity was measured with the BRITELITE kit from Perkin-Elmer and luminescence was measured in a TOPCOUNT NXT from Perkin Elmer.

Figure 9:
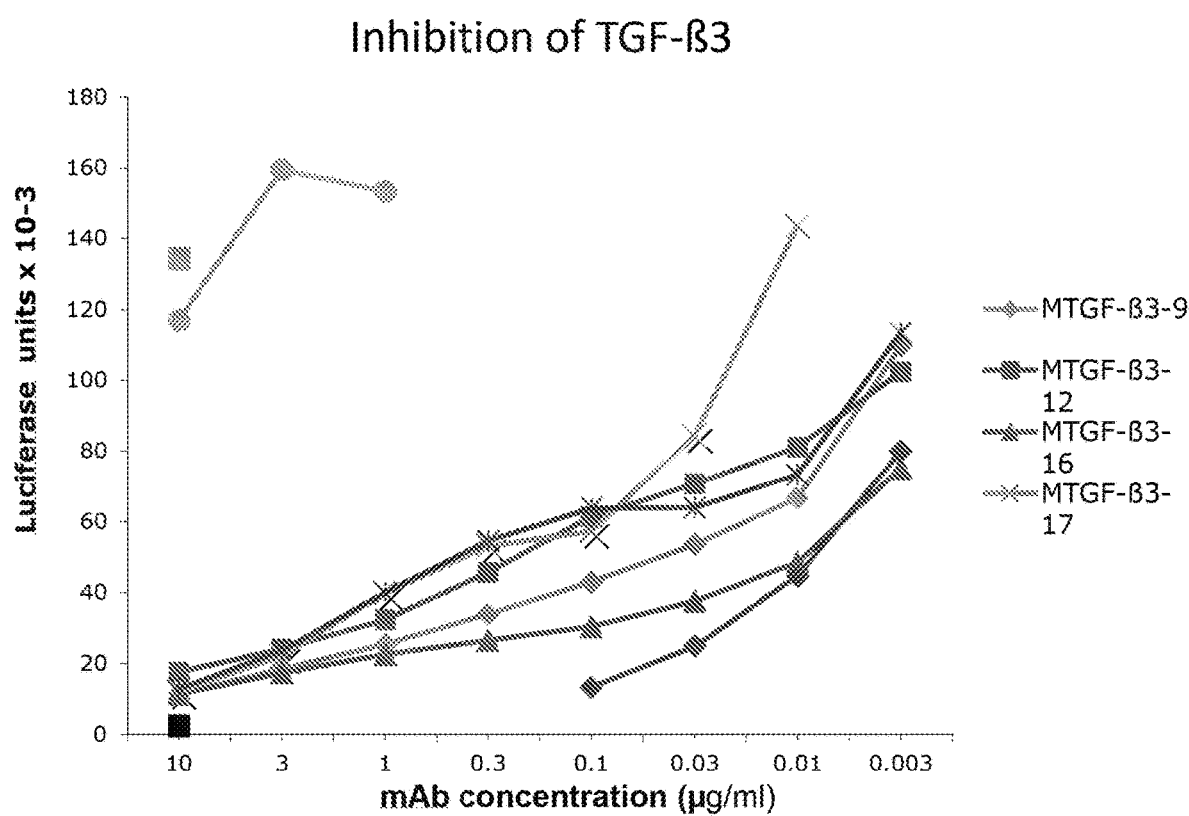
FIG. 9 depicts TGF-β3 inhibition by decreasing doses of the TGF-β3 antibodies. TMLEC cells were used in bioassays to detect TGF-β3. TMLEC sensitivity to the three different TGF-β isoforms is equivalent. Each of MTGF antibodies MTGF-β3-9, MTGF-β3-12, MTGF-β3-16, MTGF-β3-17, MTGF-β3-19, and TGF-β1 antibody MTGF-β1-13A1 were evaluated individually for inhibition of TGF-β3 at mAb concentrations 10 μg/ml to 0.003 μg/ml. Antibody 1D11, which recognizes all three TGF-β isoforms, was used as a control.
Figure 10:
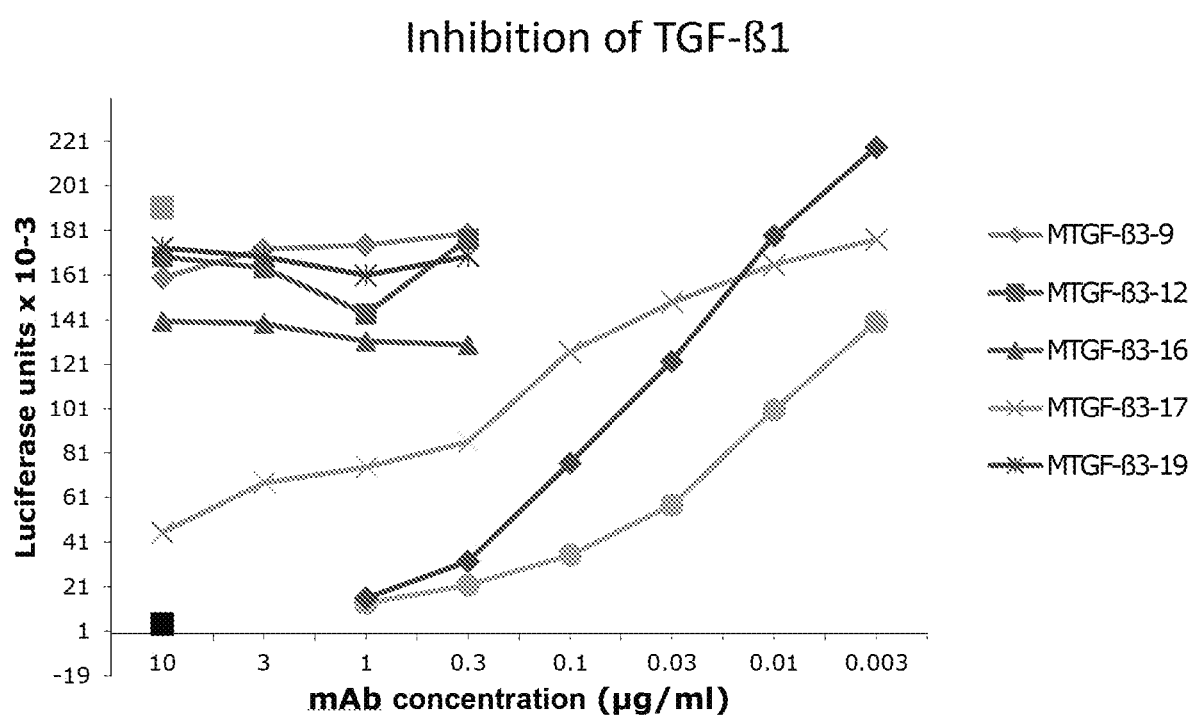
FIG. 10 depicts TGF-β1 inhibition by decreasing doses of the TGF-β3 antibodies. TMLEC cells were used in bioassays to detect TGF-β1. Each of MTGF antibodies MTGF-β3-9, MTGF-β3-12, MTGF-β3-16, MTGF-β3-17, MTGF-β3-19, and TGF-β1 antibody MTGF-β1-13A1 were evaluated individually for inhibition of TGF-β1 at mAb concentrations 10 μg/ml to 0.003 μg/ml. Antibody 1D11, which recognizes all three TGF-β isoforms, and TGF-β1 with no antibody were used as controls.
Figure 11:
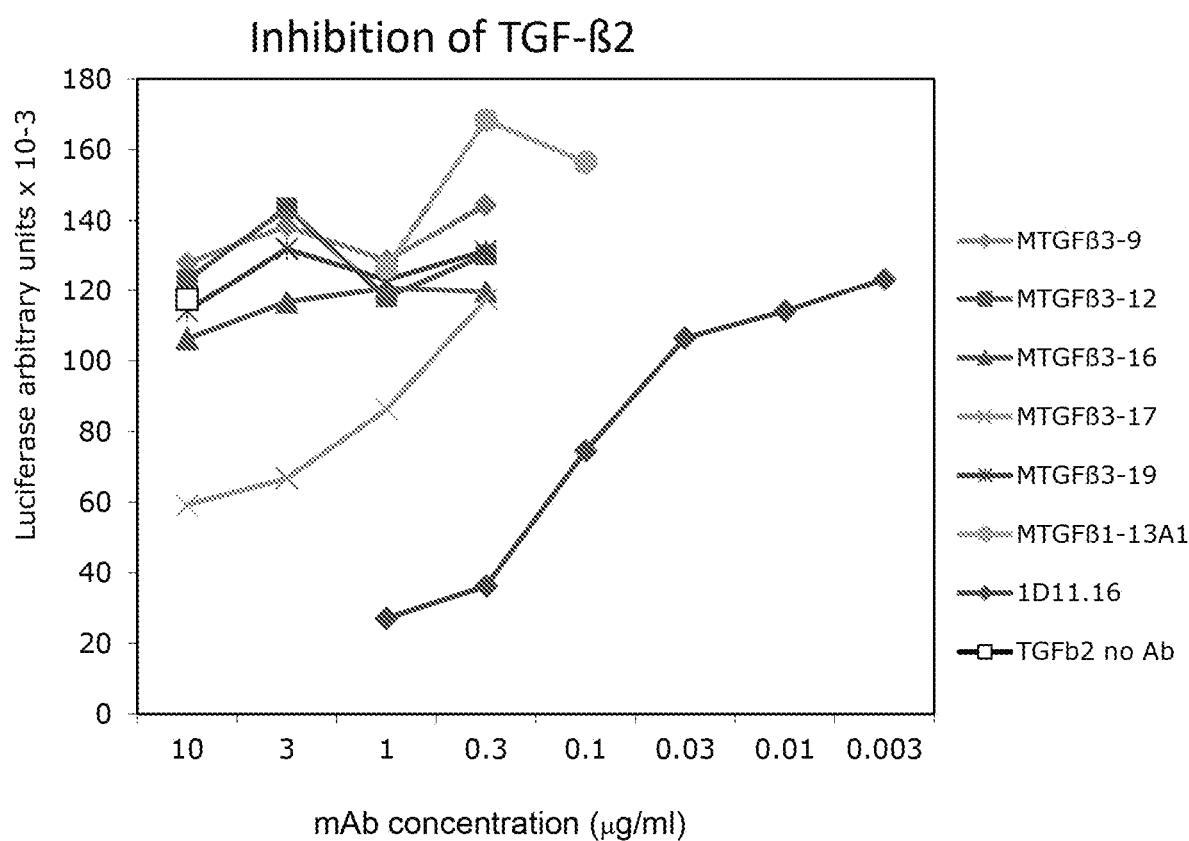
FIG. 11 depicts TGF-β2 inhibition by decreasing doses of the TGF-β3 antibodies. TMLEC cells were used in bioassays to detect TGF-β2. Each of MTGF antibodies MTGF-β3-9, MTGF-β3-12, MTGF-β3-16, MTGF-β3-17, MTGF-β3-19, and TGF-β1 antibody MTGF-β1-13A1 were evaluated individually for inhibition of TGF-β2 at mAb concentrations 10 μg/ml to 0.003 μg/ml. Antibody 1D11 and TGF-β2 with no antibody were used as controls.

In the presence of TGF-β3 antibodies, TGF-β3-mediated induction of the PAI-1 promoter is reduced in a dose dependent manner. In particular, antibody MTGFβ3-16 is very potent at inhibiting TGF-β3 bioactivity (FIG. 9). The data indicate that there appears to be a trend in selectivity of the clones tested for TGF-β3 over prior art antibody 1D11 in neutralizing TGF-β3. Except for clone MTGFβ3-17, the other clones inhibit only TGF-β3 (not TGF-β1 and TGF-β2) (FIGS. 10 and 11). MTGF-β1-13A1, a monoclonal TGF-β1 specific antibody that we previously described (Uyttenhove C et al (2011) Journal of Leukocyte biology 89(6):1001-1007) was included as a selective TGF-β1 inhibitor. The inhibitory titer (IC50), defined as the dilution giving 50% inhibition of cytokine biological activities for each human TGF-β isoform, are provided for each of the various antibodies in TABLE 1. The IC50 results clearly demonstrate that, while the four other MTGF-β3 antibodies are specific for TGF-β3 and do not inhibit the other isoforms TGF-β1 or TGF-β2, antibody MTGFβ3-17 (like 1D11) inhibits all TGF-β isoforms (although TGF-β2 very poorly). These data also show that the MTGF-β1-13A1 antibody is a very potent and specific TGF-β1 inhibitor.

TABLE 1

Summary of Specific Inhibitory Activities of Anti-TGF-β3 Antibodies

| ABs | Clone Name | IC 50 (ng/ml) | | |
|---|---|---|---|---|
| | | TGF-β1 | TGF-β2 | TGF-β3 |
| MTGF-β3-9 | TGF-β3-9/8 | No inhibition | No inhibition | 13 |
| MTGF-β3-12 | TGF-β3-1203/11 | No inhibition | No inhibition | 54 |
| MTGF-β3-16 | TGF-β3-1679/2 | No inhibition | No inhibition | 6 |
| MTGF-β3-917 | TGF-β3-1719/13 | 263 | No inhibition | 79 |
| MTGF-β3-19 | TGF-β3-1901/1 | No inhibition | No inhibition | 25 |
| MTGF-β1-13A1 | 13A1 | 14 | No inhibition | No inhibition |
| 1D11 | 1D11.6 | 72 | 53.7 | 6.5 |

For the above tabulated studies, the IC50 was calculated as the antibody concentration required for 50% inhibition in a TMLEC assay with 500 pg/ml of the different TGF-β isoforms. Antibody ranging from 10 to 0 µg/ml were incubated with 500 pg/ml of the different TGF-β isoforms and TMLEC cells for 24 hours. The concentration of antibody inhibiting 50% of the luciferase signal (IC50) were calculated by linear interpolation.

Example 5

Anti-TGF-β3 and Anti-TGF-β1 Efficacy in 4T1 Tumor Model in Naive BALB/C Mice

4T1 is a mammary carcinoma with high metastatic capacity when introduced orthotopically into BALB/c mice (Miller F R, Miller B E, Heppner G H: Characterization of metastatic heterogeneity among subpopulations of a single mouse mammary tumor: heterogeneity in phenotypic stability. Invasion Metastasis 1983, 3(1):22-31.). 4T1 cells were transfected with P1A, the major rejection antigen of the P815 mastocytoma, to provide a specific CTL target. BALB/c female mice were injected with $10^4$ 4T1-P1A cells sc into the mammary fatpad. They received 0.5 mg mAbs ip on d0, then 0.2 mg once a week till the end of the experiment.

4T1 cells were transfected with plasmid pEF4/V5-HisA Neo having sequences corresponding to the P1A 35-43 peptide (LPYLGWLVF (SEQ ID NO:49)) (Lethe B et al. 1991 J. Exp. Med 173:1373). Briefly, $5\times10^6$ cells resuspended in 0.8 ml RPMI culture medium containing 10% FCS were mixed with 50 ug plasmid DNA in a 4 mm electroporation cassette. Electric pulse (300V, 1500 uF, 100 ohms) was applied using a Bio-Rad Gene Pulser®. Cells were resuspended immediately in 25 ml culture medium. After 48 h, electroporated cells were diluted in culture medium containing 400 ug/ml G418 for selection of transfected cells. Transfectants were then cloned by single cell sorting using a BD FACSARIA III apparatus. Expression of P1A in several clones was checked by their ability to induce IFN-gamma production by transgenic CD8 T cells expressing a P1A specific TCR (Shanker A et al 2004 J. Immunol. 172: 5069-5077).

Single cell suspension of 10,000 4T1-P1A tumor cells were injected subcutaneously into right mammary fat pads of BALB/c recipients. Mice were treated intraperitoneally with 500 ug anti-TGF-β3 (clone MTGF-β3-19) starting day 0 and thereafter weekly until the experiments were completed. The amount of antibodies was reduced to 200 ug for the subsequent weekly treatment. No toxicity was observed with clone MTGF-β3-19.

Figure 12:
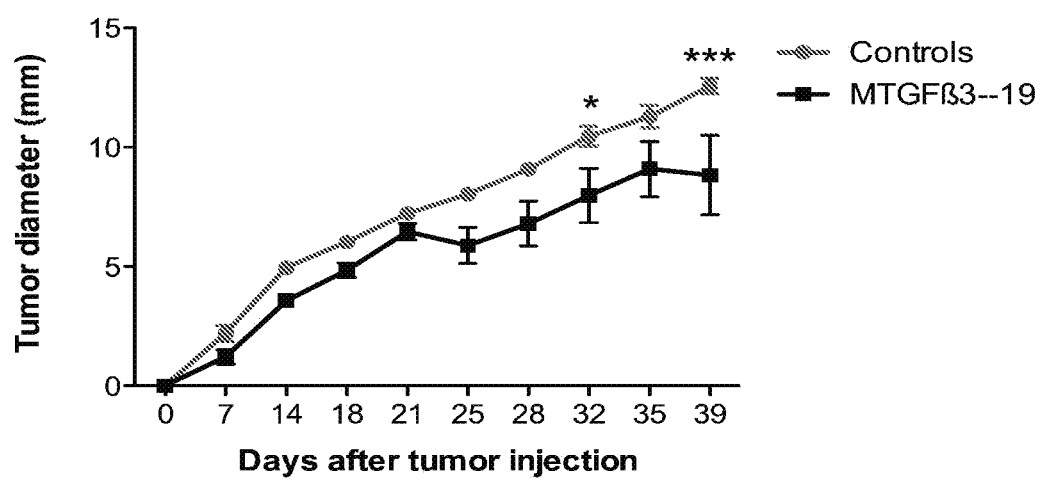
FIG. 12 depicts in vivo evaluation of mammary carcinoma tumor development in naive mice injected with antibody MTGF-β3-19. Female Balb/c mice (7-8 weeks) were injected with $10^4$ 4 T1-P1A cells implanted sc into the mammary fatpad. 4T1-P1A cells are 4T1 cells transfected with P1A, the major rejection antigen of P815 mastocytoma, to enhance their immunogenicity. 0.5 mg antibody MTGF-β3-19 (IgG1) was injected ip on day 0 and then mice received 0.2 mg of antibody once a week until the end of the experiment. The antibody MTGF-β3-19 did not show any sign of toxicity. (A) shows tumor diameter (mm) assessed up to 39 days after tumor injection. A two-way Anova analysis was preformed: $p<0.05^*$, $p<0.001^{***}$. (B) graphs the area under the curve calculated for tumor size from day 13 to day 39 for the MTGF-β3-19 antibody injected animals versus control. In T test vs control the antibody p value was p=0.015.
Figure 12:
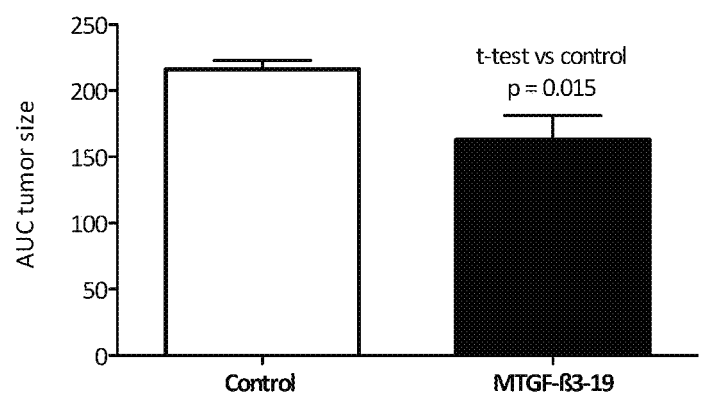

Tumor development was slower in naive mice injected with MTGF-β3-19 compared to controls (FIG. 12).

Example 6

Anti-TGF-β3 and Anti-TGF-β1 Efficacy in 4T1 Tumor Model in Vaccinated BALB/C Mice Recombinant viruses such as Semliki Forest virus (SFV-P1A) or adenovirus vectors expressing P1A (Adeno-P1A) induce T cell responses against the P1A tumor Ag (Naslund 2007 Journal of Immunology 178:6761-9). To elicit immunity against 4T1 P1A-expressing tumors (4T1-P1A), Balb/c mice received $10^8$ pfu Adeno-P1A on d0 and $10^7$ pfu SFV-P1A on d16 intradermally in the ear lobe. Fourteen days later, $10^4$ 4 T1-P1A cells were seeded in the mammary fat pad. Following inoculation of 4T1-P1A cells, Balb/c mice received 500 ug anti-TGF-β3 (clone MTGF-β3-19) ip on day 0 of the experiment and thereafter 200 ug weekly until the experiment was completed.

Figure 13:
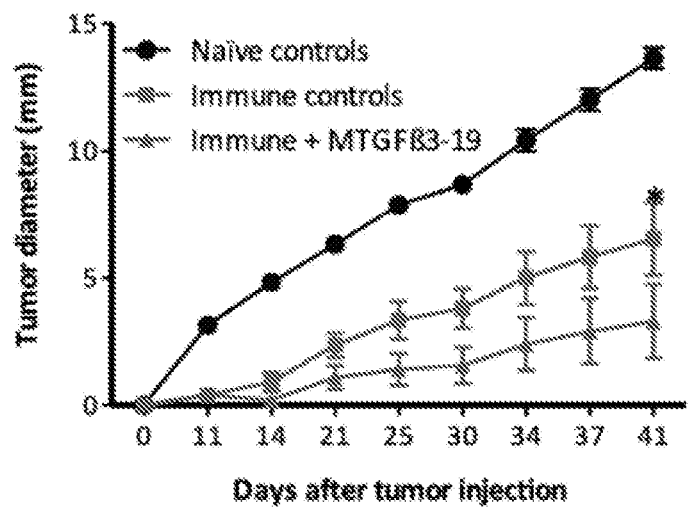
FIG. 13 depicts the effect of antibody MTGF-β3-19 on 4T1-P1A tumor growth in P1A-vaccinated Balb/c mice. Mice were immunized against P1A by a prime-boost regimen. Adenovirus vectors expressing P1A (Adeno-II-P1At) $10^8$ pfu (24/9) and Semliki Forest virus (SFV-P1A) $10^7$ IU (10/10) were administered id into the ears. Mice were injected 14 days later with $10^4$ 4 T1-P1A cells into the mammary fatpad (24/10). All immune mice were then pooled before antibody injection of 0.5 mg ip on day 0, then 0.2 mg antibody once a week. Two way Anova assessment of immune versus immune+MTGF-β3-19: * p<0.05. (A) graphs tumor diameter in mm vs days after tumor injection. (B) depicts area under the curve calculated from day 11 to day 41.
Figure 13:
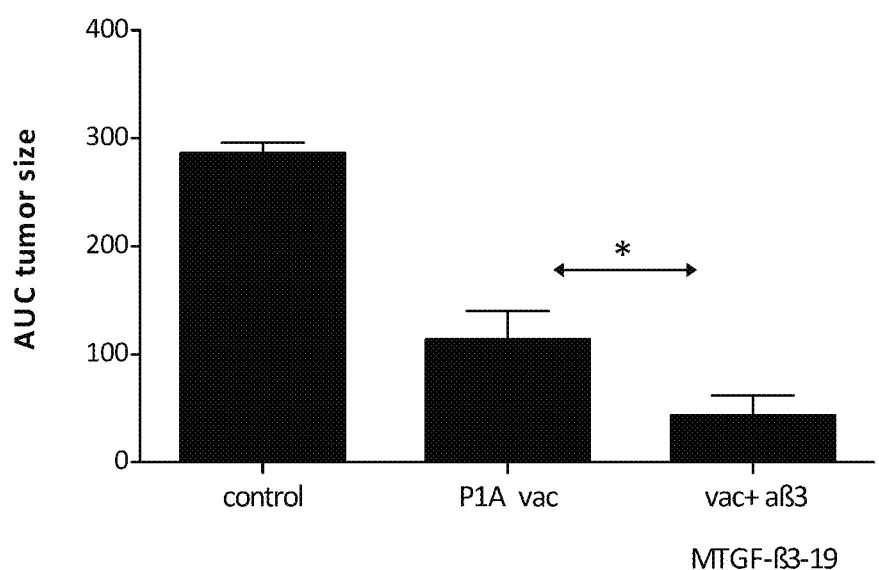
Figure 14:
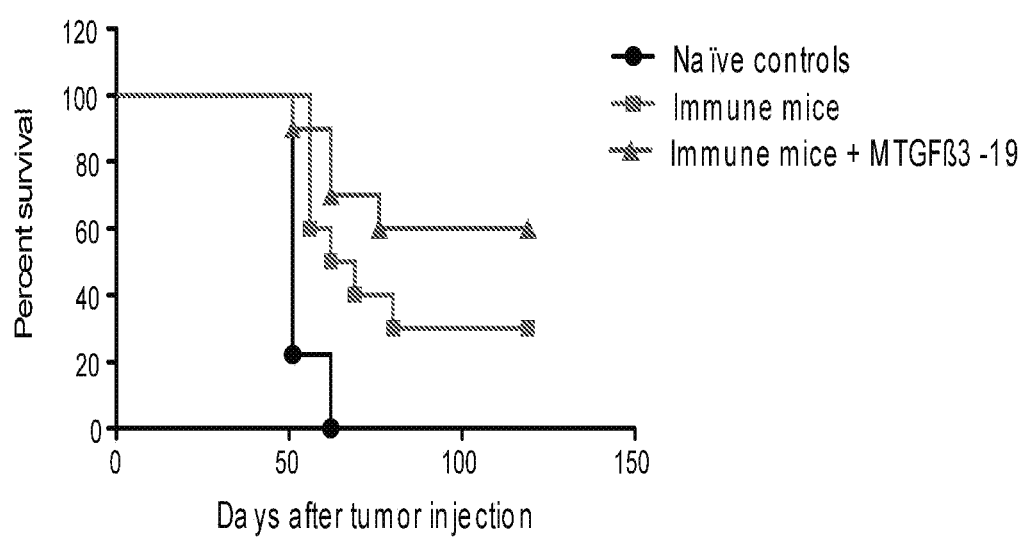
FIG. 14 shows the effect of antibody MTGF-β3-19 on the survival of immune Balb/c mice injected with 4T1-P1A cells. Mice were immunized against P1A by a prime-boost regimen of adenovirus vectors expressing P1A (Adeno-II-P1At) $10^8$ pfu and Semliki Forest virus (SFV-P1A) $10^7$ IU administered id into the ears. Fourteen days later mice were injected with $10^4$ 4 T1-P1A cells into the mammary fatpad. All immune mice were then pooled before MTGF-β3-19 antibody injection of 0.5 mg ip on day 0, then 0.2 mg antibody once a week. Log rank test: Naive versus immune: p=0.0013; Naive versus immune+MTGF-β3-19: p=0.0005*; Immune versus immune plus MTGF-β3-19: p=0.1947 ns.

MTGF-β3-19 treatment significantly decreased tumor growth compared to nave and immune controls (FIG. 13). Collectively the data demonstrated that in the context of an ongoing immune response or vaccination, the blockade of TGF-β3 with anti-TGF-β3 antibody can further refrain tumor development. There was also a strong trend towards enhanced survival (FIG. 14).

Based on these experiments, it is evident that blocking TGF-β3 decreases TGF-β receptor signaling sufficiently to increase immune protection against tumors.

This invention may be embodied in other forms or carried out in other ways without departing from the spirit or essential characteristics thereof. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. An isolated nucleic acid which comprises a sequence encoding an antibody molecule or antigen binding fragment thereof, which recognizes human and mouse transforming growth factor beta 3 (TGF-β3) and which neutralizes activity of the TGF-β3, and is an antibody or fragment comprising:
   (a) a light chain variable region comprising a CDR1 sequence KASQSVINDVA (SEQ ID NO:1) or KASQSVINAVA (SEQ ID NO:7), a CDR2 sequence YASNRYT (SEQ ID NO:2), and a CDR3 sequence QQDYSSPYT (SEQ ID NO:3), and a heavy chain variable region sequence comprising a CDR1 sequence SSWMH (SEQ ID NO:4) or SSWIH (SEQ ID NO:8), a CDR2 sequence RIFPGDGDTIYNGNFKG (SEQ ID NO:5) or RIYPGDGDTNYTGKFKG (SEQ ID NO:9), and a CDR3 sequence RMITTQAAMDY (SEQ ID NO:6);
   (b) a light chain variable region comprising a CDR1 sequence KSSQSLLNSGNQKNYLA (SEQ ID NO:10), a CDR2 sequence GASTRES (SEQ ID NO:11), and a CDR3 sequence QNDHGFPLT (SEQ ID NO:12), and a heavy chain variable region sequence comprising a CDR1 sequence DYYIN (SEQ ID NO:13), a CDR2 sequence KIGPGTGRTYYNEKFKG (SEQ ID NO:14), and a CDR3 sequence YYGWG-YAMDY (SEQ ID NO:15); or
   (c) a light chain variable region comprising a CDR1 sequence RSSQSLIHSHGNTYLH (SEQ ID NO:16), a CDR2 sequence KLSNRFS (SEQ ID NO:17), and a CDR3 sequence SQSTHVPFT (SEQ ID NO:18), and a heavy chain variable region sequence comprising a CDR1 sequence SYWIT (SEQ ID NO:19), a CDR2 sequence DIFPGTGSTNYNEKFKT (SEQ ID NO:20), and a CDR3 sequence KLGPNYAVDY (SEQ ID NO:21).

2. The nucleic acid of claim 1 wherein the encoded antibody or fragment does not react with TGF-β1 or TGF-β2.

3. The nucleic acid of claim 1 which encodes an antibody or fragment comprising:
   (a) a light chain variable region comprising a CDR1 sequence KASQSVINDVA (SEQ ID NO:1), a CDR2 sequence YASNRYT (SEQ ID NO:2), and a CDR3 sequence QQDYSSPYT (SEQ ID NO:3), and a heavy chain variable region sequence comprising a CDR1 sequence SSWMH (SEQ ID NO:4), a CDR2 sequence RIFPGDGDTIYNGNFKG (SEQ ID NO:5), and a CDR3 sequence RMITTQAAMDY (SEQ ID NO:6);
   (b) a light chain variable region comprising a CDR1 sequence KASQSVINAVA (SEQ ID NO:7), a CDR2 sequence YASNRYT (SEQ ID NO:2), and a CDR3 sequence QQDYSSPYT (SEQ ID NO:3), and a heavy chain variable region sequence comprising a CDR1 sequence SSWIH (SEQ ID NO:8), a CDR2 sequence RIYPGDGDTNYTGKFKG (SEQ ID NO:9), and a CDR3 sequence RMITTQAAMDY (SEQ ID NO:6); or
   (c) a light chain variable region comprising a CDR1 sequence KSSQSLLNSGNQKNYLA (SEQ ID NO:10), a CDR2 sequence GASTRES (SEQ ID NO:11), and a CDR3 sequence QNDHGFPLT (SEQ ID NO:12), and a heavy chain variable region sequence comprising a CDR1 sequence DYYIN (SEQ ID NO:13), a CDR2 sequence KIGPGTGRTYYNEKFKG (SEQ ID NO:14), and a CDR3 sequence YYGWG-YAMDY (SEQ ID NO:15).

4. The nucleic acid of claim 1 which encodes an antibody or fragment comprising heavy chain variable region CDRs wherein the CDR1 domain comprises a sequence SSWXH wherein X is either M or I (SEQ ID NO:42), the CDR2 domain comprises a sequence RIFPGDGDTIYNGNFKG (SEQ ID NO:5) or RIYPGDGDTNYTGKFKG (SEQ ID NO:9) and the CDR3 domain comprises a sequence RMITTQAAMDY (SEQ ID NO:6).

5. The nucleic acid of claim 4 which encodes an antibody or fragment further comprising light chain variable region CDRs wherein the CDR1 domain comprises a sequence KASQSVINXVA wherein X is either D or A (SEQ ID NO:44), the CDR2 domain comprises a sequence YASNRYT (SEQ ID NO:2), and the CDR3 domain comprises a sequence QQDYSSPYT (SEQ ID NO:3).

6. The nucleic acid of claim 1 which encodes an antibody or fragment comprising a heavy chain variable region amino acid sequence selected from the amino acid sequence set out in SEQ ID NO: 23, 27, 31, 35 or 39, or variants thereof having at least 90% amino acid identity to the heavy chain variable region sequence set out in SEQ ID NO: 23, 27, 31, 35 or 39, wherein said variants retain TGF-β3 reactivity and neutralization.

7. The nucleic acid of claim 6 which encodes an antibody or fragment further comprising a light chain variable region comprising an amino acid sequence selected from the amino acid sequence as set out in SEQ ID NO: 25, 29, 33, 37 or 41, or variants thereof having at least 90% amino acid identity to the light chain variable region sequence set out in SEQ ID NO: 25, 29, 33, 37 or 41, wherein said variants retain TGF-β3 reactivity and neutralization.

8. The nucleic acid of claim 7 which encodes an antibody which comprises a heavy chain having a variable region amino sequence comprising the amino acid sequence as set out in SEQ ID NO: 23, 31 or 39 or comprising the CDR domain sequences CDR1 sequence SSWMH (SEQ ID NO:4) or SSWIH (SEQ ID NO:8), CDR2 sequence RIFPGDGDTIYNGNFKG (SEQ ID NO:5) or RIYPGDGDTNYTGKFKG (SEQ ID NO:9), and CDR3 sequence RMITTQAAMDY (SEQ ID NO:6).

9. The nucleic acid of claim 7 which encodes an antibody which comprises a light chain having a variable region amino sequence comprising the amino acid sequence as set out in SEQ ID NO: 25, 33 or 41 or comprising the CDR region sequences CDR domain sequences CDR1 sequence KASQSVINDVA (SEQ ID NO:1) or KASQSVINAVA (SEQ ID NO:7), CDR2 sequence YASNRYT (SEQ ID NO:2), and CDR3 sequence QQDYSSPYT (SEQ ID NO:3).

10. The nucleic acid of claim 1 which comprises DNA.

11. A recombinant DNA molecule comprising the sequence of claim 1.

12. The recombinant DNA molecule of claim 11, wherein said sequence is operatively linked to an expression control sequence.

13. A unicellular host transformed with a recombinant DNA molecule of claim 11 or 12.

14. A vector which comprises the recombinant DNA molecule of claim 11 or 12.

15. An isolated host vector system for the production of an antibody or fragment thereof which comprises the vector of claim 14 in a suitable host cell.

16. A method of preparing an antibody or antigen binding fragment thereof which recognizes human and mouse transforming growth factor beta 3 (TGF-β3) and which neutralizes activity of the TGF-β3 which comprises expressing the nucleic acid of any of claims 1-9 under conditions to bring about the expression of said antibody or fragment, and recovering the antibody or fragment.

\* \* \* \* \*

SEQUENCE LISTING

```
<160> NUMBER OF SEQ ID NOS: 49

<210> SEQ ID NO 1
<211> LENGTH: 11
<212> TYPE: PRT
<213> ORGANISM: Mus musculus

<400> SEQUENCE: 1

Lys Ala Ser Gln Ser Val Ile Asn Asp Val Ala
1               5                   10

<210> SEQ ID NO 2
<211> LENGTH: 7
<212> TYPE: PRT
<213> ORGANISM: Mus Musculus

<400> SEQUENCE: 2

Tyr Ala Ser Asn Arg Tyr Thr
1               5
```

<210> SEQ ID NO 3
<211> LENGTH: 9
<212> TYPE: PRT
<213> ORGANISM: Mus musculus

<400> SEQUENCE: 3

Gln Gln Asp Tyr Ser Ser Pro Tyr Thr
1               5

<210> SEQ ID NO 4
<211> LENGTH: 5
<212> TYPE: PRT
<213> ORGANISM: Mus musculus

<400> SEQUENCE: 4

Ser Ser Trp Met His
1               5

<210> SEQ ID NO 5
<211> LENGTH: 17
<212> TYPE: PRT
<213> ORGANISM: Mus musculus

<400> SEQUENCE: 5

Arg Ile Phe Pro Gly Asp Gly Asp Thr Ile Tyr Asn Gly Asn Phe Lys
1               5                   10                  15

Gly

<210> SEQ ID NO 6
<211> LENGTH: 11
<212> TYPE: PRT
<213> ORGANISM: Mus musculus

<400> SEQUENCE: 6

Arg Met Ile Thr Thr Gln Ala Ala Met Asp Tyr
1               5                   10

<210> SEQ ID NO 7
<211> LENGTH: 11
<212> TYPE: PRT
<213> ORGANISM: Mus musculus

<400> SEQUENCE: 7

Lys Ala Ser Gln Ser Val Ile Asn Ala Val Ala
1               5                   10

<210> SEQ ID NO 8
<211> LENGTH: 5
<212> TYPE: PRT
<213> ORGANISM: Mus musculus

<400> SEQUENCE: 8

Ser Ser Trp Ile His
1               5

<210> SEQ ID NO 9
<211> LENGTH: 17
<212> TYPE: PRT
<213> ORGANISM: Mus musculus

<400> SEQUENCE: 9

Arg Ile Tyr Pro Gly Asp Gly Asp Thr Asn Tyr Thr Gly Lys Phe Lys
1               5                   10                  15

Gly

<210> SEQ ID NO 10
<211> LENGTH: 17
<212> TYPE: PRT
<213> ORGANISM: Mus musculus

<400> SEQUENCE: 10

```
Lys Ser Ser Gln Ser Leu Leu Asn Ser Gly Asn Gln Lys Asn Tyr Leu
1               5                   10                  15
Ala
```

<210> SEQ ID NO 11
<211> LENGTH: 7
<212> TYPE: PRT
<213> ORGANISM: Mus musculus

<400> SEQUENCE: 11

```
Gly Ala Ser Thr Arg Glu Ser
1               5
```

<210> SEQ ID NO 12
<211> LENGTH: 9
<212> TYPE: PRT
<213> ORGANISM: Mus musculus

<400> SEQUENCE: 12

```
Gln Asn Asp His Gly Phe Pro Leu Thr
1               5
```

<210> SEQ ID NO 13
<211> LENGTH: 5
<212> TYPE: PRT
<213> ORGANISM: Mus musculus

<400> SEQUENCE: 13

```
Asp Tyr Tyr Ile Asn
1               5
```

<210> SEQ ID NO 14
<211> LENGTH: 17
<212> TYPE: PRT
<213> ORGANISM: Mus musculus

<400> SEQUENCE: 14

```
Lys Ile Gly Pro Gly Thr Gly Arg Thr Tyr Tyr Asn Glu Lys Phe Lys
1               5                   10                  15
Gly
```

<210> SEQ ID NO 15
<211> LENGTH: 10
<212> TYPE: PRT
<213> ORGANISM: Mus musculus

<400> SEQUENCE: 15

```
Tyr Tyr Gly Trp Gly Tyr Ala Met Asp Tyr
1               5                   10
```

<210> SEQ ID NO 16
<211> LENGTH: 16
<212> TYPE: PRT
<213> ORGANISM: Mus musculus -continued

<400> SEQUENCE: 16

Arg Ser Ser Gln Ser Leu Ile His Ser His Gly Asn Thr Tyr Leu His
1               5                   10                  15

<210> SEQ ID NO 17
<211> LENGTH: 7
<212> TYPE: PRT
<213> ORGANISM: Mus musculus

<400> SEQUENCE: 17

Lys Leu Ser Asn Arg Phe Ser
1               5

<210> SEQ ID NO 18
<211> LENGTH: 9
<212> TYPE: PRT
<213> ORGANISM: Mus musculus

<400> SEQUENCE: 18

Ser Gln Ser Thr His Val Pro Phe Thr
1               5

<210> SEQ ID NO 19
<211> LENGTH: 5
<212> TYPE: PRT
<213> ORGANISM: Mus musculus

<400> SEQUENCE: 19

Ser Tyr Trp Ile Thr
1               5

<210> SEQ ID NO 20
<211> LENGTH: 17
<212> TYPE: PRT
<213> ORGANISM: Mus musculus

<400> SEQUENCE: 20

Asp Ile Phe Pro Gly Thr Gly Ser Thr Asn Tyr Asn Glu Lys Phe Lys
1               5                   10                  15

Thr

<210> SEQ ID NO 21
<211> LENGTH: 10
<212> TYPE: PRT
<213> ORGANISM: Mus musculus

<400> SEQUENCE: 21

Lys Leu Gly Pro Asn Tyr Ala Val Asp Tyr
1               5                   10

<210> SEQ ID NO 22
<211> LENGTH: 417
<212> TYPE: DNA
<213> ORGANISM: Mus musculus

<400> SEQUENCE: 22
atggaatggc cttgtatctt tctcttcctc ctgtcagtaa ctgaaggtgt ccactcccag      60
gttctgctgc agcagtctgg acctgagctg gtgaagcctg ggccctcagt gaagatttcc    120
tgcaaggctt ctggctacgc attcagtagc tcctggatgc actgggtgaa gcagaggcct    180 ggaaaggtc ttgagtggat tgacggatt tttcctggag atgagatac tatctacaat      240 gggaatttca aggcaaggc cacacttact gcagacaaat cctccagcac agcctacatg    300

```
caactcagca gcctgacatc tgaggactct gcggtctact tctgtgcaag aaggatgatt    360
acgactcagg cggctatgga ctactggggt caaggaacct cagtcaccgt ctcctca      417
```

<210> SEQ ID NO 23
<211> LENGTH: 139
<212> TYPE: PRT
<213> ORGANISM: Mus musculus

<400> SEQUENCE: 23

```
Met Glu Trp Pro Cys Ile Phe Leu Phe Leu Leu Ser Val Thr Glu Gly
1               5                   10                  15

Val His Ser Gln Val Leu Leu Gln Gln Ser Gly Pro Glu Leu Val Lys
            20                  25                  30

Pro Gly Ala Ser Val Lys Ile Ser Cys Lys Ala Ser Gly Tyr Ala Phe
        35                  40                  45

Ser Ser Ser Trp Met His Trp Val Lys Gln Arg Pro Gly Lys Gly Leu
    50                  55                  60

Glu Trp Ile Gly Arg Ile Phe Pro Gly Asp Gly Asp Thr Ile Tyr Asn
65                  70                  75                  80

Gly Asn Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Arg Met Ile Thr Thr Gln Ala Ala Met Asp Tyr
        115                 120                 125

Trp Gly Gln Gly Thr Ser Val Thr Val Ser Ser
    130                 135
```

<210> SEQ ID NO 24
<211> LENGTH: 381
<212> TYPE: DNA
<213> ORGANISM: Mus musculus

<400> SEQUENCE: 24

```
atgaagtcac agacccaggt cttcgtattt ctactgctct gtgtgtctgg tgctcatggg    60
agtattgtga tgacccagac tcccaaattc ctgcttgtat cagcaggaga cagggttacc   120
ataacctgca aggccagtca gagtgtgatt aatgatgtag cttggtacca acagaagcca   180
gggcagtctc ctaaactgct gatatactat gcatccaatc ggtacactgg agtccctgat   240
cgcttcactg gcaatggata tgggacggat ttcactttca ccatcagcac tgtgcaggct   300
gaagacctgg cagtttattt ctgtcagcag gattatagct ctccgtacac gttcggaggg   360
gggaccaagc tggaaataaa a                                              381
```

<210> SEQ ID NO 25
<211> LENGTH: 127
<212> TYPE: PRT
<213> ORGANISM: Mus musculus

<400> SEQUENCE: 25

```
Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45
```

Val Ile Asn Asp Val Ala Trp Tyr Gln Gln Lys Pro Gly Gln Ser Pro
 50                  55                  60

Lys Leu Leu Ile Tyr Tyr Ala Ser Asn Arg Tyr Thr Gly Val Pro Asp
 65                  70                  75                  80

Arg Phe Thr Gly Asn Gly Tyr Gly Thr Asp Phe Thr Phe Thr Ile Ser
                 85                  90                  95

Thr Val Gln Ala Glu Asp Leu Ala Val Tyr Phe Cys Gln Gln Asp Tyr
            100                 105                 110

Ser Ser Pro Tyr Thr Phe Gly Gly Thr Lys Leu Glu Ile Lys
        115                 120                 125

<210> SEQ ID NO 26
<211> LENGTH: 414
<212> TYPE: DNA
<213> ORGANISM: Mus musculus

<400> SEQUENCE: 26
atggaatgga gctgggtctt tctcttcctc ctgtcagtaa ctgcaggtgt ccactgccag     60
gtccagctga agcagtctgg agctgagctg gtgaagcctg ggcttcagt gaagatatcc    120 tgcaaggctt ctggctacac cttcactgac tactatataa actgggtgaa gcagaggcct    180
ggacagggcc ttgagtggat tgggaagatt ggtcctggaa ctggtcgtac ttactacaat    240
gagaagttca aggcaaggc cacactgact gcagacaaat cctccagcac agcctacatg    300
cagctcagca gcctgacatc tgaggactct gcagtctatt tctgtgcaat ctactatggt    360
tggggctatg ctatggacta ctgggtcaa ggaacctcag tcaccgtctc ctca    414

<210> SEQ ID NO 27
<211> LENGTH: 138
<212> TYPE: PRT
<213> ORGANISM: Mus musculus

<400> SEQUENCE: 27

Met Glu Trp Ser Trp Val Phe Leu Phe Leu Leu Ser Val Thr Ala Gly
 1               5                  10                  15

Val His Cys Gln Val Gln Leu Lys Gln Ser Gly Ala Glu Leu Val Lys
            20                  25                  30

Pro Gly Ala Ser Val Lys Ile Ser Cys Lys Ala Ser Gly Tyr Thr Phe
         35                  40                  45

Thr Asp Tyr Tyr Ile Asn Trp Val Lys Gln Arg Pro Gly Gln Gly Leu
 50                  55                  60

Glu Trp Ile Gly Lys Ile Gly Pro Gly Thr Gly Arg Thr Tyr Tyr Asn
 65                  70                  75                  80

Glu Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Glu Asp Ser Ala Val
            100                 105                 110

Tyr Phe Cys Ala Ile Tyr Tyr Gly Trp Gly Tyr Ala Met Asp Tyr Trp
        115                 120                 125

Gly Gln Gly Thr Ser Val Thr Val Ser Ser
        130                 135

<210> SEQ ID NO 28
<211> LENGTH: 399
<212> TYPE: DNA
<213> ORGANISM: Mus musculus

<400> SEQUENCE: 28

```
atggaatcac agactcaggt cctcatctcc ttgctgttct gggtatctgg tacctgtggg      60
gacattgtga tgacacagtc tccatcctcc ctgagtgtgt cagcaggaga gaaggtcact     120
atgagctgca agtccagtca gagtctgtta aacagtggaa atcaaaagaa ctacttggcc     180
tggtaccagc agaaatcagg gcagcctcct aaactgttga tctatggggc atccactagg     240
gaatctgggg tccctgatcg cttcacaggc agtggatctg gaaccgattt cactcttacc     300
atcagcagtg tgcaggctga agacctggca gtttattact gtcagaatga tcatggtttt     360
ccgctcacgt tcggtgctgg gaccaagctg gagctgaaa                           399
```

<210> SEQ ID NO 29
<211> LENGTH: 133
<212> TYPE: PRT
<213> ORGANISM: Mus musculus

<400> SEQUENCE: 29

Met Glu Ser Gln Thr Gln Val Leu Ile Ser Leu Leu Phe Trp Val Ser
1               5                   10                  15

Gly Thr Cys Gly Asp Ile Val Met Thr Gln Ser Pro Ser Ser Leu Ser
            20                  25                  30

Val Ser Ala Gly Glu Lys Val Thr Met Ser Cys Lys Ser Ser Gln Ser
        35                  40                  45

Leu Leu Asn Ser Gly Asn Gln Lys Asn Tyr Leu Ala Trp Tyr Gln Gln
    50                  55                  60

Lys Ser Gly Gln Pro Pro Lys Leu Leu Ile Tyr Gly Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp His Gly Phe Pro Leu Thr Phe Gly Ala Gly Thr
        115                 120                 125

Lys Leu Glu Leu Lys
    130

<210> SEQ ID NO 30
<211> LENGTH: 417
<212> TYPE: DNA
<213> ORGANISM: Mus musculus

<400> SEQUENCE: 30

```
atggaatggc cttgtatctt tctcttcctc ctgtcagtaa ctgaaggtgt ccactcccag      60
gttctcctgc agcagtctgg acctgagctg gtgaagcctg gggcctcagt gaagatttcc     120
tgcaaggctt ctggctacgc attcagtagc tcctggatac actgggtgaa gcagaggcct     180
ggaaagggtc ttgagtggat tggacggatt tatccgggag atggagatac taactatact     240
gggaagttca aggcaaggc acacttact gcagacaaat cctccagcac agcctacatg       300
caactcagca gcctgacatc tgaggactct gcggtctact tctgtgcaag aaggatgatt     360
acgactcagg cggctatgga ctactgggggt caaggaacct cagtcaccgt ctcctca       417
```

<210> SEQ ID NO 31
<211> LENGTH: 139
<212> TYPE: PRT
<213> ORGANISM: Mus musculus

<400> SEQUENCE: 31

```
Met Glu Trp Pro Cys Ile Phe Leu Phe Leu Leu Ser Val Thr Glu Gly
1               5                   10                  15

Val His Ser Gln Val Leu Leu Gln Gln Ser Gly Pro Glu Leu Val Lys
                20                  25                  30

Pro Gly Ala Ser Val Lys Ile Ser Cys Lys Ala Ser Gly Tyr Ala Phe
            35                  40                  45

Ser Ser Ser Trp Ile His Trp Val Lys Gln Arg Pro Gly Lys Gly Leu
        50                  55                  60

Glu Trp Ile Gly Arg Ile Tyr Pro Gly Asp Gly Asp Thr Asn Tyr Thr
65              70                  75                  80

Gly Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Arg Met Ile Thr Thr Gln Ala Ala Met Asp Tyr
        115                 120                 125

Trp Gly Gln Gly Thr Ser Val Thr Val Ser Ser
        130                 135
```

<210> SEQ ID NO 32
<211> LENGTH: 381
<212> TYPE: DNA
<213> ORGANISM: Mus musculus

<400> SEQUENCE: 32

```
atgaagtcac agacccaggt cttcgtattt ctactgctct gtgtgtctgg tgctcatggg    60
agttttgtga tgacccagac tcccaaattc ctgcttgtat cagcaggaga cagggttacc   120
ataacctgca aggccagtca gagtgtgatt aatgctgtag cttggtacca acagaagcca   180
gggcagtctc ctaaactgct gatatactat gcatccaatc gctacactgg agtccctgat   240
cgcttcactg gcaatggata tgggacggat ttcactttca ccatcagcac tgtgcaggct   300
gaagacctgg cagtttattt ctgtcagcag gattatagct ctccgtacac gttcggaggg   360
gggaccaagc tggaaataaa a                                              381
```

<210> SEQ ID NO 33
<211> LENGTH: 127
<212> TYPE: PRT
<213> ORGANISM: Mus musculus

<400> SEQUENCE: 33

```
Met Lys Ser Gln Thr Gln Val Phe Val Phe Leu Leu Leu Cys Val Ser
1               5                   10                  15

Gly Ala His Gly Ser Phe Val Met Thr Gln Thr Pro Lys Phe Leu Leu
                20                  25                  30

Val Ser Ala Gly Asp Arg Val Thr Ile Thr Cys Lys Ala Ser Gln Ser
            35                  40                  45

Val Ile Asn Ala Val Ala Trp Tyr Gln Gln Lys Pro Gly Gln Ser Pro
        50                  55                  60

Lys Leu Leu Ile Tyr Tyr Ala Ser Asn Arg Tyr Thr Gly Val Pro Asp
65              70                  75                  80

Arg Phe Thr Gly Asn Gly Tyr Gly Thr Asp Phe Thr Phe Thr Ile Ser
                85                  90                  95

Thr Val Gln Ala Glu Asp Leu Ala Val Tyr Phe Cys Gln Gln Asp Tyr
            100                 105                 110
```

```
Ser Ser Pro Tyr Thr Phe Gly Gly Thr Lys Leu Glu Ile Lys
        115                 120                 125
```

<210> SEQ ID NO 34
<211> LENGTH: 414
<212> TYPE: DNA
<213> ORGANISM: Mus musculus

<400> SEQUENCE: 34

```
atgggatgga gctgtatcat cctcattttg gtagcagcag ctacaggtgt ccactcccag      60
gtccaactgc agcagcctgg ggctgagctt gtgaagcctg ggcttcagt gaagatgtcc      120
tgcaaggctt ctggctacat tttcaccagc tactggataa cctgggtgaa gcagaggcct      180
ggacaaggcc ttgagtggat tggagatatt ttcctggga ctggtagtac taactacaat      240
gagaagttca agaccaaggc ctcactgact gtagacacat cctccagcac agccaacatg      300
cagctcagca gcctgacatc tgaggactca gcggtctatt cctgtgcaag aaaactgggc      360
cctaactatg ctgtggacta ctggggtcaa ggaacctcag tcaccgtctc ctca            414
```

<210> SEQ ID NO 35
<211> LENGTH: 138
<212> TYPE: PRT
<213> ORGANISM: Mus musculus

<400> SEQUENCE: 35

```
Met Gly Trp Ser Cys Ile Ile Leu Ile Leu Val Ala Ala Ala Thr Gly
1               5                   10                  15
Val His Ser Gln Val Gln Leu Gln Gln Pro Gly Ala Glu Leu Val Lys
            20                  25                  30
Pro Gly Ala Ser Val Lys Met Ser Cys Lys Ala Ser Gly Tyr Ile Phe
        35                  40                  45
Thr Ser Tyr Trp Ile Thr Trp Val Lys Gln Arg Pro Gly Gln Gly Leu
    50                  55                  60
Glu Trp Ile Gly Asp Ile Phe Pro Gly Thr Gly Ser Thr Asn Tyr Asn
65                  70                  75                  80
Glu Lys Phe Lys Thr Lys Ala Ser Leu Thr Val Asp Thr Ser Ser Ser
                85                  90                  95
Thr Ala Asn Met Gln Leu Ser Ser Leu Thr Ser Glu Asp Ser Ala Val
            100                 105                 110
Tyr Ser Cys Ala Arg Lys Leu Gly Pro Asn Tyr Ala Val Asp Tyr Trp
        115                 120                 125
Gly Gln Gly Thr Ser Val Thr Val Ser Ser
    130                 135
```

<210> SEQ ID NO 36
<211> LENGTH: 393
<212> TYPE: DNA
<213> ORGANISM: Mus musculus

<400> SEQUENCE: 36

```
atgaagttgc ctgttaggct gttggtgctg atgttctgga ttcctgcttc cagcagtgat      60
gttgtgatga cccaaactcc actctccctg cctgtcagtc ttggagatca agcctccatc      120
tcttgcagat ctagtcagag ccttatacac agtcatggaa acacctattt acattggtac      180
ctgcagaagc caggccagtc tccaaagctc ctgatctaca aactttccaa ccgattttct      240
ggggtcccag acaggttcag tggcagtgga tcagggacaa ttttcacact caagatcagc      300
agagtggagg ctgaggatct gggagtttat ttctgctctc aaagtacaca tgttccattc      360
```
acgttcggct cgggggacaaa gttggaaata aaa          393

<210> SEQ ID NO 37
<211> LENGTH: 131
<212> TYPE: PRT
<213> ORGANISM: Mus musculus

<400> SEQUENCE: 37

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser His Gly Asn Thr Tyr Leu His Trp Tyr Leu Gln Lys Pro
    50                  55                  60

Gly Gln Ser Pro Lys Leu Leu Ile Tyr Lys Leu Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Phe Thr Phe Gly Ser Gly Thr Lys Leu
        115                 120                 125

Glu Ile Lys
    130

<210> SEQ ID NO 38
<211> LENGTH: 417
<212> TYPE: DNA
<213> ORGANISM: Mus musculus

<400> SEQUENCE: 38
atggaatggc cttgtatctt tctcttcctc ctgtcagtaa ctgaaggtgt ccactcccag      60
gttctcctgc agcagtctgg acctgagctg gtgaagcctg ggcctcagt gaagatttcc     120 tgcaaggctt ctggctacgc attcagtagc tcctggatac actgggtgaa gcagaggcct     180
ggaaagggtc ttgagtggat tggacggatt tatccgggag atggagatac taactatact     240
gggaagttca gggcaaggc cacacttact gcagacaaat cctccagcac agcctacatg     300
caactcagca gcctgacatc tgaggactct gcggtctact tctgtgcaag aaggatgatt     360
acgactcagg cggctatgga ctactggggt caaggaacct cagtcaccgt ctcctca       417

<210> SEQ ID NO 39
<211> LENGTH: 139
<212> TYPE: PRT
<213> ORGANISM: Mus musculus

<400> SEQUENCE: 39

Met Glu Trp Pro Cys Ile Phe Leu Phe Leu Leu Ser Val Thr Glu Gly
1               5                   10                  15

Val His Ser Gln Val Leu Leu Gln Gln Ser Gly Pro Glu Leu Val Lys
            20                  25                  30

Pro Gly Ala Ser Val Lys Ile Ser Cys Lys Ala Ser Gly Tyr Ala Phe
        35                  40                  45

Ser Ser Ser Trp Ile His Trp Val Lys Gln Arg Pro Gly Lys Gly Leu
    50                  55                  60

```
Glu Trp Ile Gly Arg Ile Tyr Pro Gly Asp Gly Asp Thr Asn Tyr Thr
 65                  70                  75                  80

Gly Lys Phe Lys Gly Lys Ala Thr Leu Thr Ala Asp Lys Ser Ser Ser
             85                  90                  95

Thr Ala Tyr Met Gln Leu Ser Ser Leu Thr Ser Glu Asp Ser Ala Val
            100                 105                 110

Tyr Phe Cys Ala Arg Arg Met Ile Thr Thr Gln Ala Ala Met Asp Tyr
        115                 120                 125

Trp Gly Gln Gly Thr Ser Val Thr Val Ser Ser
    130                 135
```

```
<210> SEQ ID NO 40
<211> LENGTH: 381
<212> TYPE: DNA
<213> ORGANISM: Mus musculus

<400> SEQUENCE: 40
atgaagtcac agacccaggt cttcgtattt ctactgctct gtgtgtctgg tgctcatggg    60
agttttgtga tgacccagac tcccaaattc ctgcttgtat cagcaggaga cagggttacc   120
ataacctgca aggccagtca gagtgtgatt aatgctgtag cttggtacca acagaagcca   180
gggcagtctc ctaaactgct gatatactat gcatccaatc gctacactgg agtccctgat   240
cgcttcactg gcaatggata tgggacggat ttcactttca ccatcagcac tgtgcaggct   300
gaagacctgg cagtttattt ctgtcagcag gattatagct ctccgtacac gttcggaggg   360
gggaccaagc tggaaataaa a                                             381

<210> SEQ ID NO 41
<211> LENGTH: 127
<212> TYPE: PRT
<213> ORGANISM: Mus musculus

<400> SEQUENCE: 41

Met Lys Ser Gln Thr Gln Val Phe Val Phe Leu Leu Leu Cys Val Ser
1               5                  10                  15

Gly Ala His Gly Ser Phe Val Met Thr Gln Thr Pro Lys Phe Leu Leu
             20                  25                  30

Val Ser Ala Gly Asp Arg Val Thr Ile Thr Cys Lys Ala Ser Gln Ser
         35                  40                  45

Val Ile Asn Ala Val Ala Trp Tyr Gln Gln Lys Pro Gly Gln Ser Pro
     50                  55                  60

Lys Leu Leu Ile Tyr Tyr Ala Ser Asn Arg Tyr Thr Gly Val Pro Asp
 65                  70                  75                  80

Arg Phe Thr Gly Asn Gly Tyr Gly Thr Asp Phe Thr Phe Thr Ile Ser
             85                  90                  95

Thr Val Gln Ala Glu Asp Leu Ala Val Tyr Phe Cys Gln Gln Asp Tyr
            100                 105                 110

Ser Ser Pro Tyr Thr Phe Gly Gly Gly Thr Lys Leu Glu Ile Lys
        115                 120                 125

<210> SEQ ID NO 42
<211> LENGTH: 5
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
```

```
<222> LOCATION: (4)..(4)
<223> OTHER INFORMATION: X can be M or I

<400> SEQUENCE: 42

Ser Ser Trp Xaa His
1               5

<210> SEQ ID NO 43
<211> LENGTH: 17
<212> TYPE: PRT
<213> ORGANISM: Artificial sequence
<220> FEATURE:
<223> OTHER INFORMATION: consensus sequence
<220> FEATURE:
<221> NAME/KEY: Variant
<222> LOCATION: (3)..(3)
<223> OTHER INFORMATION: X can be F or Y
<220> FEATURE:
<221> NAME/KEY: Variant
<222> LOCATION: (10)..(10)
<223> OTHER INFORMATION: X can be I or N
<220> FEATURE:
<221> NAME/KEY: Variant
<222> LOCATION: (12)..(12)
<223> OTHER INFORMATION: X can be N or T
<220> FEATURE:
<221> NAME/KEY: Variant
<222> LOCATION: (14)..(14)
<223> OTHER INFORMATION: X can be N or K

<400> SEQUENCE: 43

Arg Ile Xaa Pro Gly Asp Gly Asp Thr Xaa Tyr Xaa Gly Xaa Phe Lys
1               5                   10                  15

Gly

<210> SEQ ID NO 44
<211> LENGTH: 11
<212> TYPE: PRT
<213> ORGANISM: Artificial sequence
<220> FEATURE:
<223> OTHER INFORMATION: consensus sequence
<220> FEATURE:
<221> NAME/KEY: variant
<222> LOCATION: (9)..(9)
<223> OTHER INFORMATION: X can be D or A

<400> SEQUENCE: 44

Lys Ala Ser Gln Ser Val Ile Asn Xaa Val Ala
1               5                   10

<210> SEQ ID NO 45
<211> LENGTH: 112
<212> TYPE: PRT
<213> ORGANISM: Mus musculus

<400> SEQUENCE: 45

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80
```

```
Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 46
<211> LENGTH: 112
<212> TYPE: PRT
<213> ORGANISM: Homo sapiens

<400> SEQUENCE: 46

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 47
<211> LENGTH: 13
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: X is cycloexylamine

<400> SEQUENCE: 47

Cys Lys Xaa Val Ala Ala Trp Thr Leu Lys Ala Ala Glx
1               5                   10

<210> SEQ ID NO 48
<211> LENGTH: 22
<212> TYPE: PRT
<213> ORGANISM: Artificial sequence
<220> FEATURE:
<223> OTHER INFORMATION: synthetic peptide

<400> SEQUENCE: 48

Cys Phe Asn Asn Phe Thr Val Ser Phe Trp Leu Arg Val Pro Lys Val
1               5                   10                  15

Ser Ala Ser His Leu Glu
            20

<210> SEQ ID NO 49
<211> LENGTH: 9
<212> TYPE: PRT
<213> ORGANISM: Artificial sequence
<220> FEATURE:
<223> OTHER INFORMATION: synthetic peptide
```

```
<400> SEQUENCE: 49

Leu Pro Tyr Leu Gly Trp Leu Val Phe
1               5
```